US008921552B2

(12) United States Patent
Kamal et al.

(10) Patent No.: US 8,921,552 B2
(45) Date of Patent: Dec. 30, 2014

(54) BENZOTHIAZOLE HYBRIDS USEFUL AS ANTICANCER AGENTS AND PROCESS FOR THE PREPARATION THEREOF

(71) Applicants: Ahmed Kamal, Hyderabad (IN); Adla Mallareddy, Hyderabad (IN); Paidakula Suresh, Hyderabad (IN); Rajesh V. C. R. N. C. Shetti, Hyderabad (IN); Harish Chandra Pal, Hyderabad (IN); Ajit Kumar Saxena, Hyderabad (IN)

(72) Inventors: Ahmed Kamal, Hyderabad (IN); Adla Mallareddy, Hyderabad (IN); Paidakula Suresh, Hyderabad (IN); Rajesh V. C. R. N. C. Shetti, Hyderabad (IN); Harish Chandra Pal, Hyderabad (IN); Ajit Kumar Saxena, Hyderabad (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 13/958,147

(22) Filed: Aug. 2, 2013

(65) Prior Publication Data
US 2014/0039190 A1    Feb. 6, 2014

Related U.S. Application Data

(63) Continuation of application No. PCT/IN2012/000081, filed on Feb. 3, 2012.

(30) Foreign Application Priority Data

Feb. 4, 2011    (IN) .............................. 270/DEL/2011

(51) Int. Cl.
C07D 277/66    (2006.01)
C07D 277/62    (2006.01)
C07D 417/12    (2006.01)

(52) U.S. Cl.
CPC ............ *C07D 277/66* (2013.01); *C07D 417/12* (2013.01)
USPC .......................................... 544/368; 548/180

(58) Field of Classification Search
CPC .................................................... C07D 277/66
See application file for complete search history.

(56) References Cited

FOREIGN PATENT DOCUMENTS

WO    2008099416 A2    8/2008
WO    2011117882 A1    9/2011

OTHER PUBLICATIONS

Wells, et al.; "Antitumor benzothiazoles. 13. (Diacetoxy)iodobenzene (DAIB) oxidation of 2-(4-hydroxy-3-methoxyphenyl)benzothiazole and related compounds in the presence of dienophiles"; ARKIVOC 2000 (v) 779-797.
Hutchinson, et al.; "Antitumor Benzothiazoles. 14.1 Synthesis and in Vitro Biological Properties of Fluorinated 2-(4-Aminophenyl)benzothiazoles"; J. Med. Chem. 2001, 44, 1446-1455.
Mortimer, et al.; "Antitumor Benzothiazoles. 26.1 2-(3,4-Dimethoxyphenyl)-5-fluorobenzothiazole (GW 610, NSC 721648), a Simple Fluorinated 2-Arylbenzothiazole, Shows Potent and Selective Inhibitory Activity against Lung, Colon, and Breast Cancer Cell Lines"; J. Med. Chem. 2006, 49, 179-185.
Shi, D, et al.: "Antitumor Benzothiazoles. 3.1 Synthesis of 2-(4-Aminophenyl)benzothiazoles and Evaluation of Their Activities against Breast Cancer Cell Lines in Vitro and in Vivo"; J. Med. Chem. 1996, 39, 3375-3384.
Kashiyama, et al.; "Antitumor Benzothiazoles. 8.1 Synthesis, Metabolic Formation, and Biological Properties of the C-and N-Oxidation Products of Antitumor 2-(4-Aminophenyl)- benzothiazoles"; J. Med. Chem. 1999, 42, 4172-4184.
Ducki, et al.; "Combretastatin-like chalcones as inhibitors of microtubule polymerization. Part 1: Synthesis and biological evaluation of antivascular activity"; Bioorganic & Medicinal Chemistry 17 (2009) 7698-7710.
Johnson, et al.; "Design, synthesis, and biological testing of pyrazoline derivatives of combretastatin-A4"; Bioorganic & Medicinal Chemistry Letters 17 (2007) 5897-5901.
Simoni, et al.; "Heterocyclic and Phenyl Double-Bond-Locked Combretastatin Analogues Possessing Potent Apoptosis-Inducing Activity in HL60 and in MDR Cell Lines"; J. Med. Chem. 2005, 48, 723-736.
Kaffy, et al.; "Isoxazole-type derivatives related to combretastatin A-4, synthesis and biological evaluation"; Bioorganic & Medicinal Chemistry 14 (2006) 4067-4077.
Tron, et al.; "Medicinal Chemistry of Combretastatin A4: Present and Future Directions"; © Copyright 2006 by the American Chemical Society; pp. 3033-3044.
Ben-Alloum, et al.; "Nouvelle Voie de Synth2se des 2-Arylbenzothiazoles Transfert d•Electrons Activ6 par Microondes"; (c) 1997 Elsevier Science Ltd; pp. 1490-1491.
Bhat, et al.; "Synthesis and biological evaluation of chalcones and their derived pyrazoles as potential cytotoxic agents"; Bioorganic & Medicinal Chemistry Letters 15 (2005) 3177-3180.
Pirali, et al.; "Synthesis and Cytotoxic Evaluation of Combretafurans, Potential Scaffolds for Dual-Action Antitumoral Agents"; J. Med. Chem. 2006, 49, 5372-5376.
LeBlanc, et al.; "Synthesis and cytotoxicity of epoxide and pyrazole analogs of the combretastatins"; Bioorganic & Medicinal Chemistry 13 (2005) 6025-6034.
International Search Report and Written Opinion of the International Searching Authority Application No. PCT/IN2012/000081, Completed: Apr. 3, 2012; Mailing Date: Apr. 12, 2012, 12 pages.
Balasubramanian Srinivasan, et al.; "Structure-Activity Relationship Studies of Chalcone Leading to 3-Hydroxy-4,3',4',5'-tetrannethoxychalcone and Its Analogues as Potent Nuclear Factor [kappa]B Inhibitors and Their Anticancer Activities"; Journal of Medicinal Chemistry; Nov. 26, 2009; vol. 52, Nr:22, pp. 7228-7235 (1 page abstract only).

*Primary Examiner* — Noble Jarrell
*Assistant Examiner* — John S Kenyon
(74) *Attorney, Agent, or Firm* — St. Onge Steward Johnston & Reens LLC

(57) ABSTRACT

Compounds of general formula A useful as potential anticancer agents against human cancer cell lines and a process for the preparation thereof.

Formula A
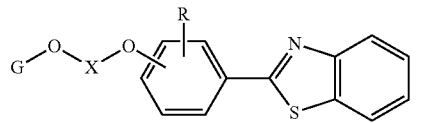
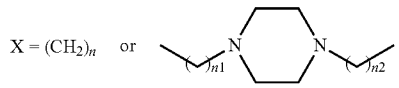
$n = 2\text{-}6; n1 \ \& \ n2 = 2\text{-}6$
Where in R = H or methoxy and
G =
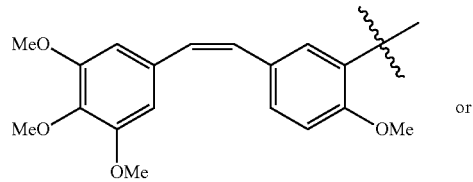
or
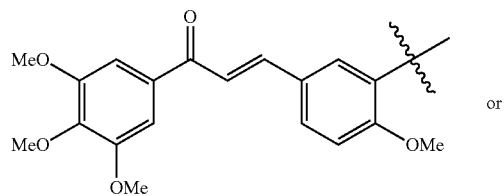
or
-continued
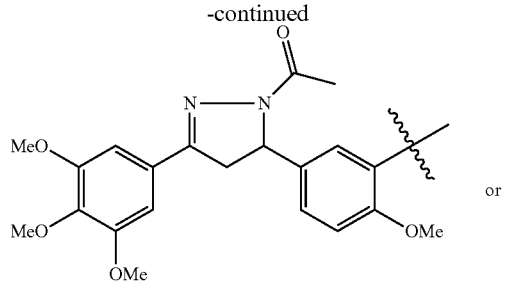
or
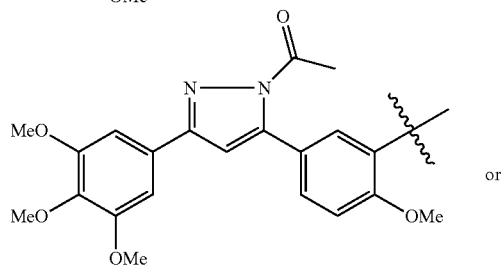
or
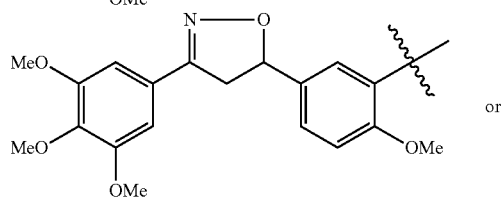
or
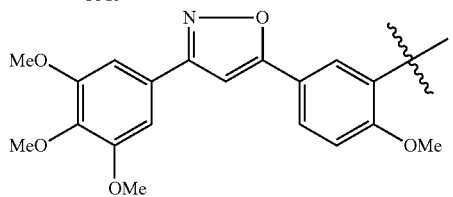
8 Claims, 5 Drawing Sheets

Reagents and conditions i) TBDMS-Cl, TEA, DMF; ii) NaBH₄, MeOH ; iii) LiBr, THF ; iv) PPh₃, toluene ; v) n-BuLi, THF, -20 °C, trimethoxy benzaldehyde; vi) TBAF, THF., TBDMS- tertiary butyl dimethyl silyl chloride Reagents and conditions i) NH$_2$OH.HCl, NaHCO$_3$, CH$_3$OH, H$_2$O; ii) CH$_3$P(Ph)$_3$$^+$Br$^-$, KOtBu, THF; iii) NaOCl, Et$_3$N, DCM; iv) TBAF, THF.

Reagents and conditions i) NH$_2$OH.HCl, NaHCO$_3$, CH$_3$OH, H$_2$O; ii) (a) CBr$_4$, PPh3, DCM; (b) n-BuLi, THF, -78 °C iii) NaOCl, Et$_3$N, DCM; iv) TBAF, THF.

Reagents and conditions; i) N-Boc piperazine, DMF, $K_2CO_3$; ii) Trifluoroacetic acid, DCM;
iii) dibromoalkane, DMF, $K_2CO_3$ ;

BENZOTHIAZOLE HYBRIDS USEFUL AS ANTICANCER AGENTS AND PROCESS FOR THE PREPARATION THEREOF

FIELD OF THE INVENTION

The present invention relates to benzothiazole hybrids useful as anticancer agents and process for the preparation thereof. Particularly, the present invention relates to benzothiazole hybrids of general formula A.

Formula A

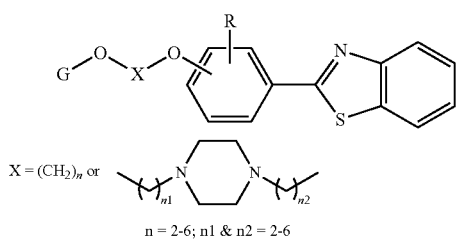

X = (CH$_2$)$_n$ or 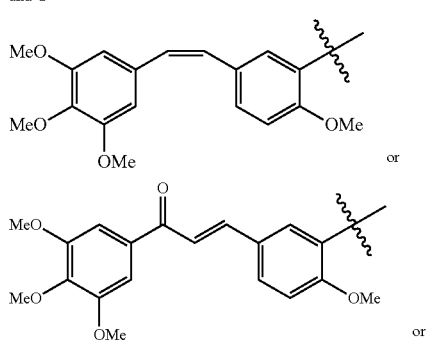

n = 2-6; n1 & n2 = 2-6

Where in R = H or methoxy
and G =

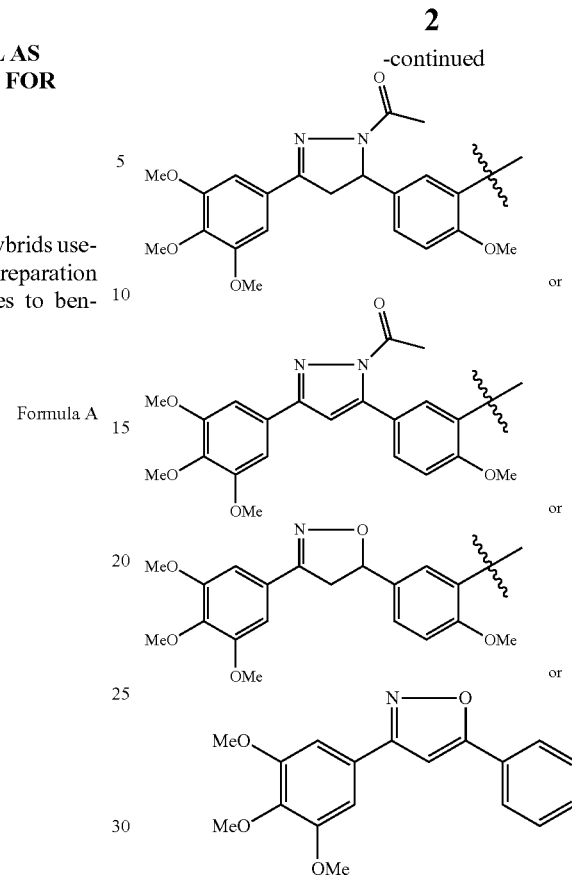

More particularly the present invention relates to olefine, chalcone, pyrazoline, pyrazole, isoxazoline and isoxazoles linked to 2-phenyl benzothiazoles with aliphatic chain length variations without piperazine and with piperazine useful as anticancer agents. The structural formulae of these benzothiazole hybrids are given below.

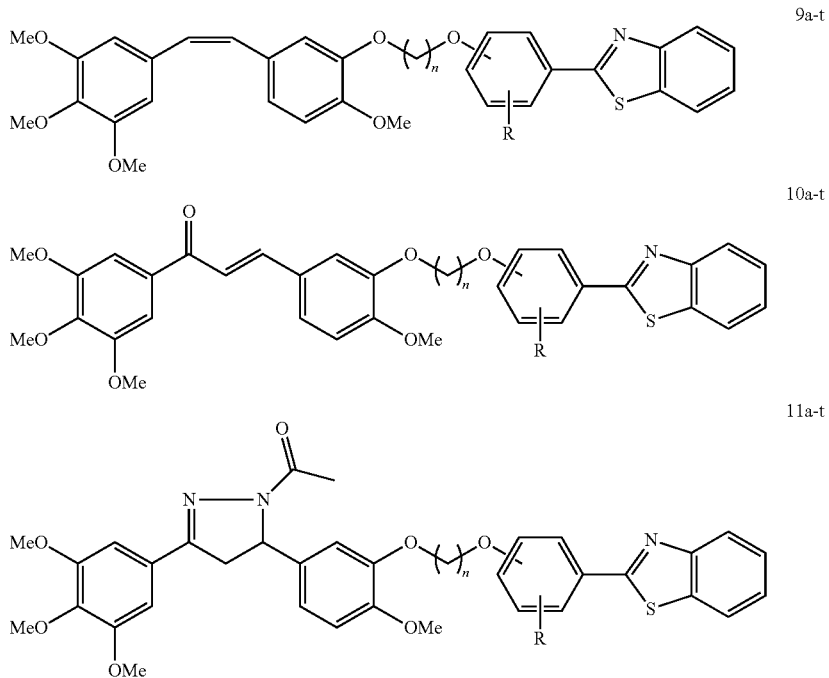

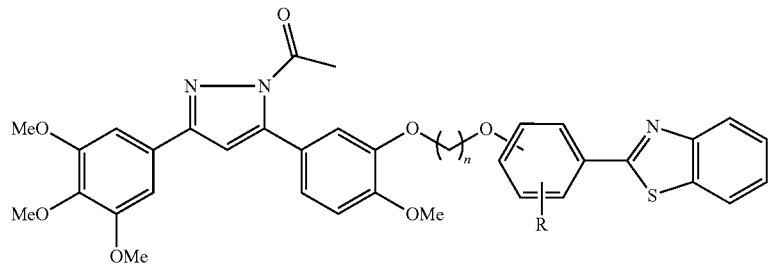
12a-t
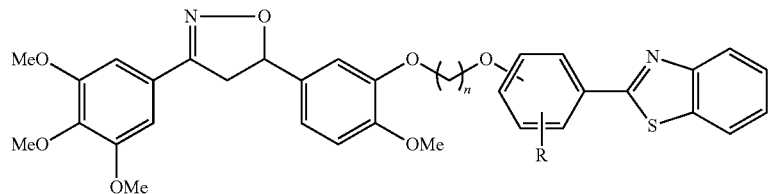
13a-t
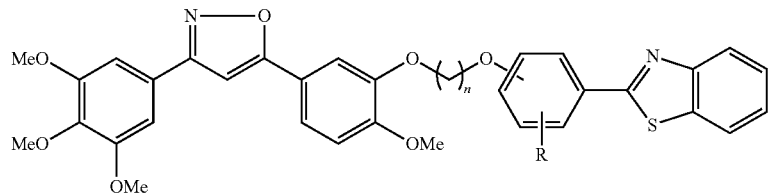
14a-t
where in n = 2-6
R = H, methoxy
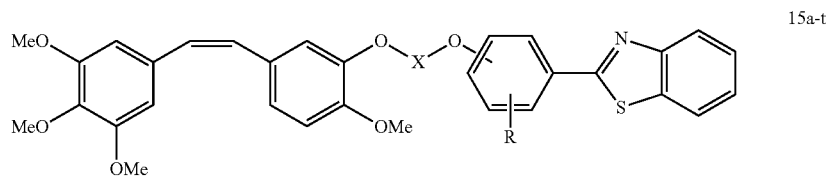
15a-t
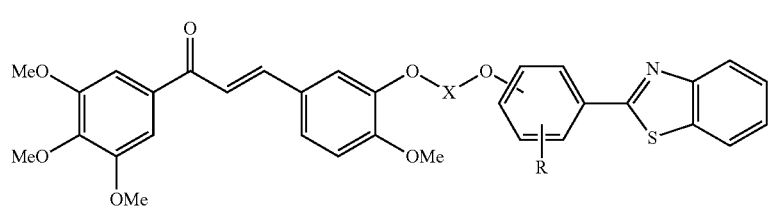
16a-t
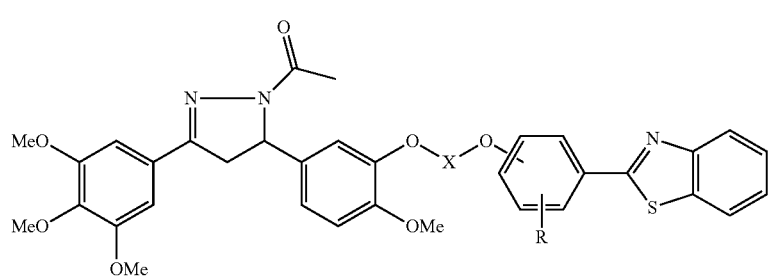
17a-t
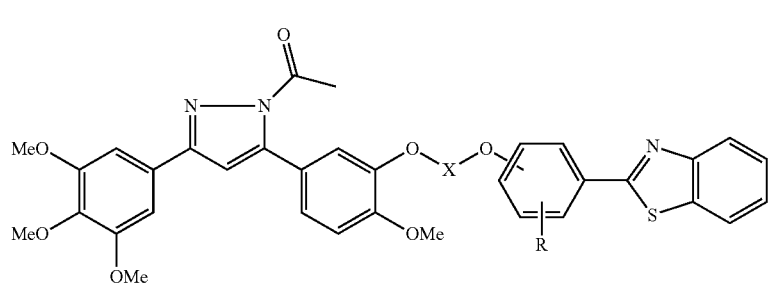
18a-t

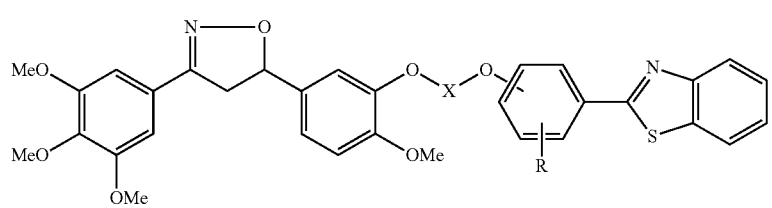

19a-t

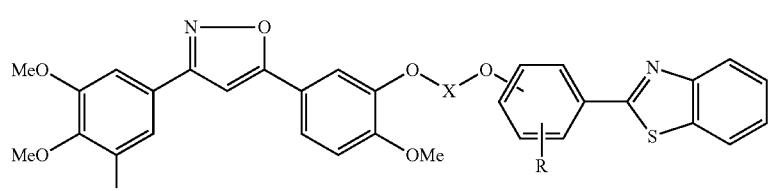

20a-t where in

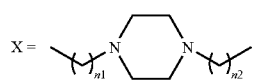

n1 and n2 = 2-6
R = H, methoxy

BACKGROUND OF THE INVENTION

Inhibition of tubulin polymerization is the target of many antitumoural agents known as antimitotic agents or spindle poisons colchicines, podophyllotoxins and combretastatins are representative examples of compounds that inhibit microtubule assembly by binding to tubulin. Benzothiazoles are small synthetic molecules that contain a benzene ring fused to a thiazole ring. These simple molecules have shown remarkable antitumour properties and some of them are undergoing evaluation in clinical trials (Shi, D.-F.; Bradshaw, T. D.; Wrigley, S.; McCall, C. J.; Lelieveld, P.; Fichtner, I.; Stevens, M. F. G. J. Med. Chem. 1996, 39, 3375; Kashiyama, E.; Hutchinson, I.; Chua, M.-S.; Stinson, S. F.; Phillips, L. R.; Kaur, G.; Sausville, E. A.; Bradshaw, T. D.; Westwell, A. D.; Stevens, M. F. G. J. Med. Chem. 1999, 42, 4172; Hutchinson, I.; Chua, M.-S.; Browne, H. L.; Trapani, V.; Bradshaw, T. D.; Westwell, A. D.; Stevens, M. F. G. J. Med. Chem. 2001, 44, 1446). Recently Westwell and coworkers have prepared a series of benzothiazole derivatives and evaluated for anticancer activity, One of these analogues has shown excellent anticancer activity (Mortimer, C. G.; Wells, G.; Crochard, J.-P.; Stone, E. L.; Bradshaw, T. D.; Stevens, M. F. G.; Westwell, A. D. J. Med. Chem. 2006, 49, 179). Many chalcone, pyrazoline pyrazoline, isoxazole and isoxazoline type moieties related to combretastain A-4 showed potential biological properties particularly anticancer activity (Sylvie Ducki, David Rennison, Meiko Woo, Alexander Kendall, Jérémie Fournier Dit Chabert, Alan T. McGown, Nicholas J. Lawrence. Bioorg. Med. Chem, 17, 2009, 7698-7710; Regan LeBlanc, John Dickson, Toni Brown, Michelle Stewart, Hari N. Pati, Don VanDerveer, Hadi Arman, Jeff Harris, William Pennington, Herman L. Holt Jr., Moses Lee. Bioorg. Med. Chem, 13, 2005, 6025-6034; Marlie Johnson, Brent Younglove, Lauren Lee, Regan LeBlanc, Herman Holt Jr., Patrice Hills, Hilary Mackay, Toni Brown, Susan L. Mooberry, Moses Lee. Bioorg. Med. Chem. Lett, 17, 2007, 5897-5901; B. A. Bhat, K. L. Dhar, S. C. Puri, A. K. Saxena, M. Shanmugavel, G. N. Qazi. Bioorg. Med. Chem. Lett, 15, 2005, 3177-3180; Simoni, D.; Grisolia, G.; Giannini, G.; Roberti, M.; Rondanin, R.; Piccagli, L.; Baruchello, R.; Rossi, M.; Romagnoli, R.; Invidiata, F. P.; Grimaudo, S.; Jung, M. K.; Hamel, E.; Gebbia, N.; Crosta, L.; Abbadessa, V.; DiCristina, A.; Dusonchet, L.; Meli, M.; Tolomeo, M. J. Med. Chem. 2005, 48, 723, Julia Kaffy, Rene'e Pontikis, a, Danie'le Carrez, b Alain Croisy, Claude Monnereta, Jean-Claude Florent. Bioorg. Med. Chem. 2006, 14, 4067-4077, Gian Ceasure Tron, Tracy Pirali, Giovanni sorba, Francesca pagliai, Sara Buasacca, Armado A. Genazzani. J. Med. Chem. 2006, 49, 3033-3044. Tracey Pirali, Sara buasacca, Lorena Beltrami, Daniela Imovilli, Francesca Paliai, Gianluca Migilio, Alberto Massrotti, Luisella Verotta, Gian Cesare Tron, Givanni Sorba, Armado A. Genazzani. J. Med. Chem. 2006, 49, 5372-5376). Some of the heterocyclic bridged Combretastains showed an attractive profile of cytotoxicity and were able to induce apoptosis at lower concentrations.

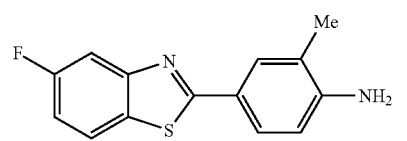

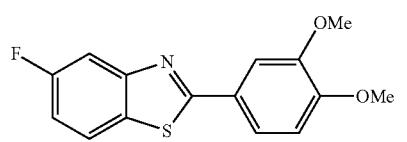

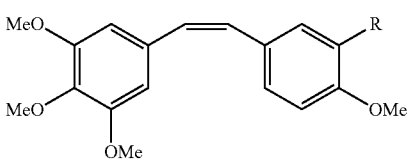

R = OH (CA4)
R = OPO₃Na₂ (CA4P)
R = NHSer, HCl(AVE8062)

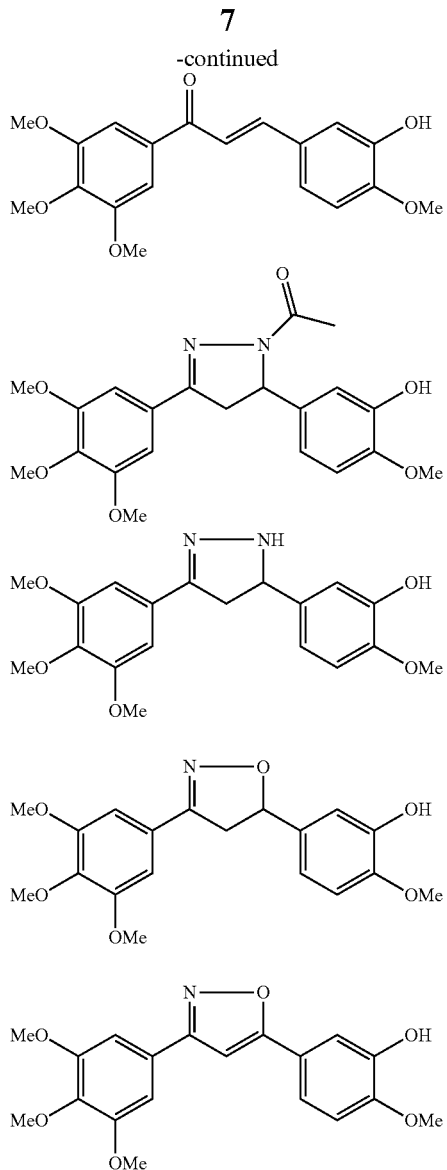

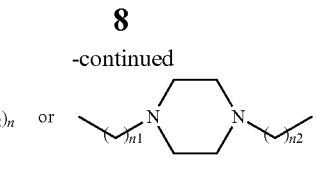

$n = 2\text{-}6; n1 \text{ \& } n2 = 2\text{-}6$

Where in R = H or methoxy and
G =

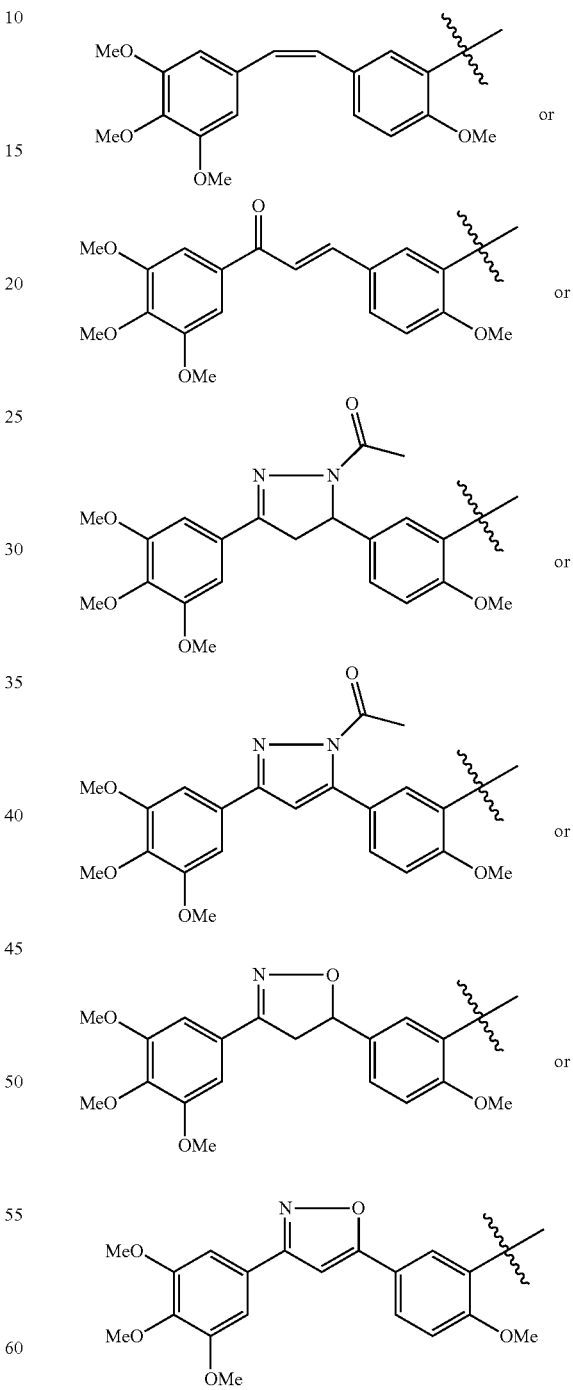

OBJECTIVES OF THE INVENTION

The main objective of the present invention is to provide novel benzothiazole hybrids useful as antitumour agents.

Yet another object of this invention is to provide a process for the preparation of novel benzothiazole hybrids.

SUMMARY OF THE INVENTION

Accordingly, the present invention provides benzothiazole hybrids of general formulae A Formula A

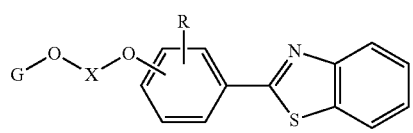

In an embodiment of the present invention Benzothiazole hybrids of formula A is represented by the following compounds of general formulae 9a-t, 10a-t, 11a-t, 12a-t, 13a-t, 14a-t, 15a-t, 16a-t, 17a-t, 18a-t, 19a-t and 20a-t.

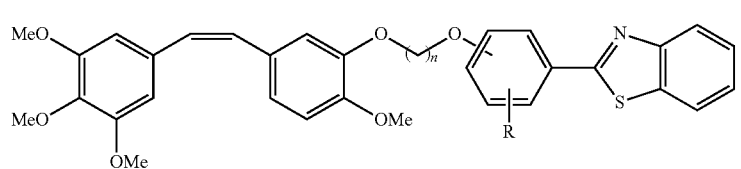
9a-t
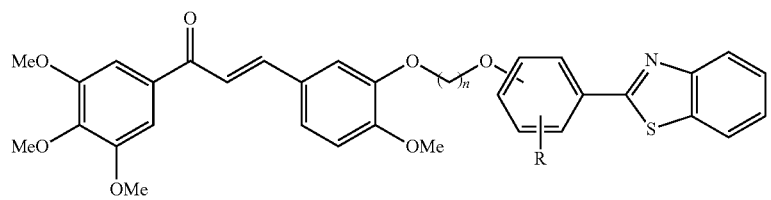
10a-t
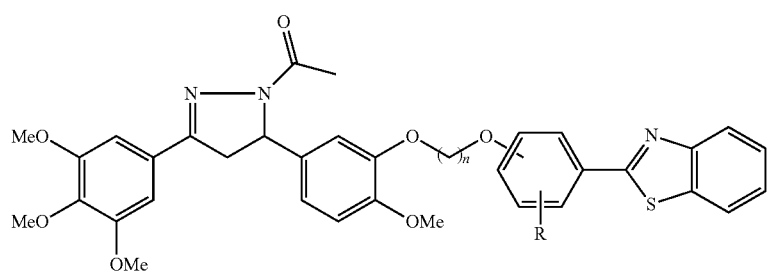
11a-t
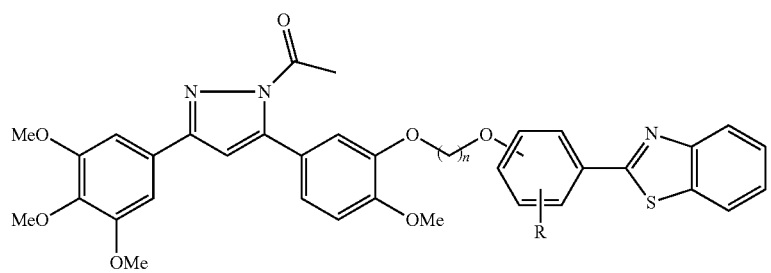
12a-t
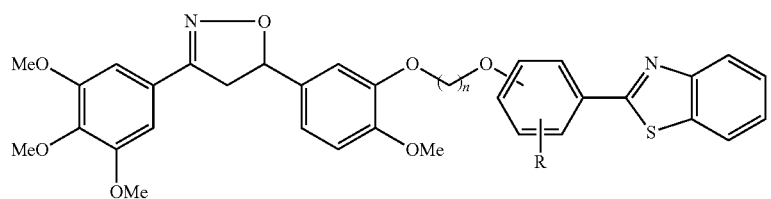
13a-t
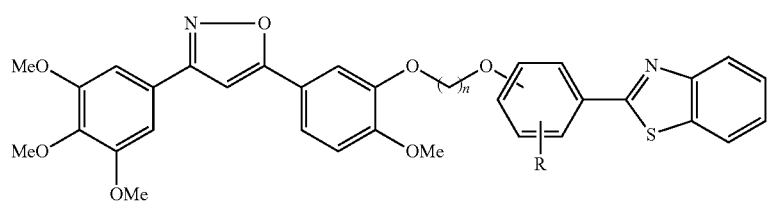
14a-t
where in n = 2-6
R = H, methoxy
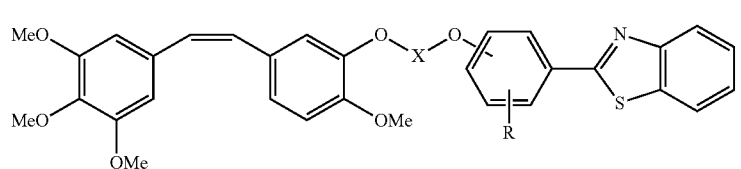
15a-t -continued
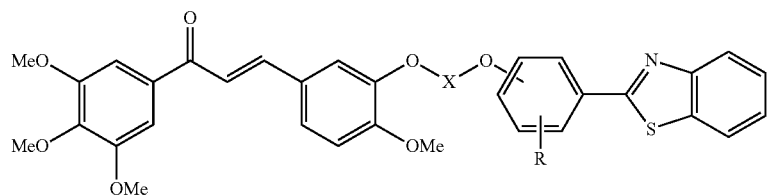
16a-t
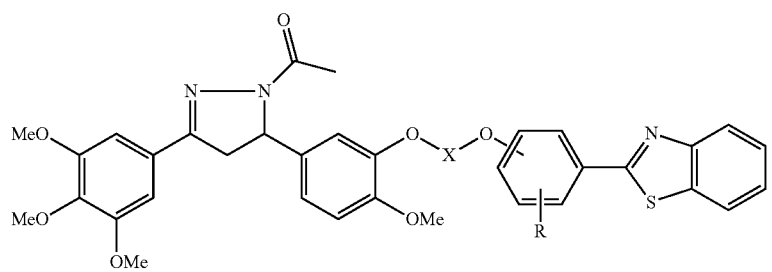
17a-t
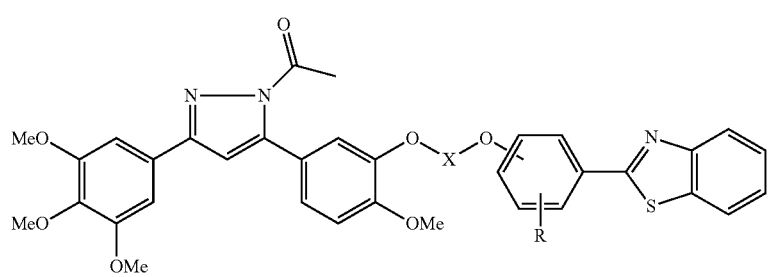
18a-t
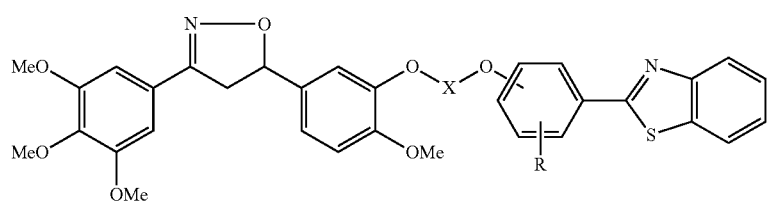
19a-t
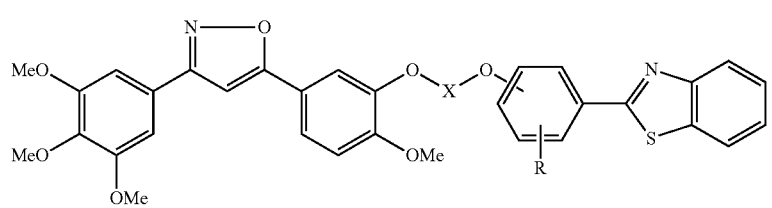
20a-t
where in X =
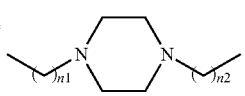
n1 and n2 = 2-6
R = H, methoxy
In another embodiment of the present invention the structural formulae of the representative compounds are:
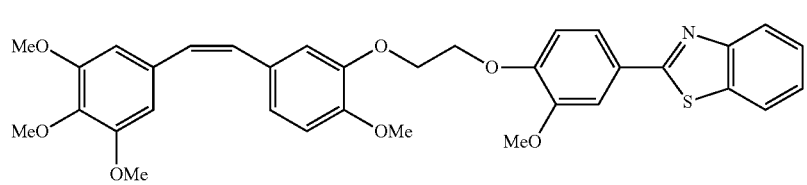
9a -continued
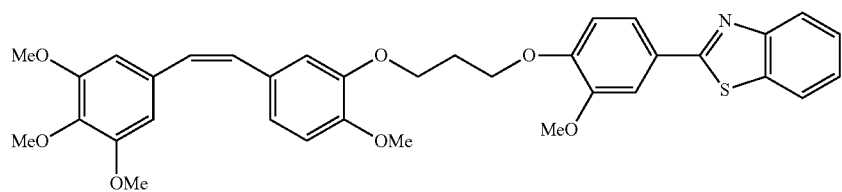
9b
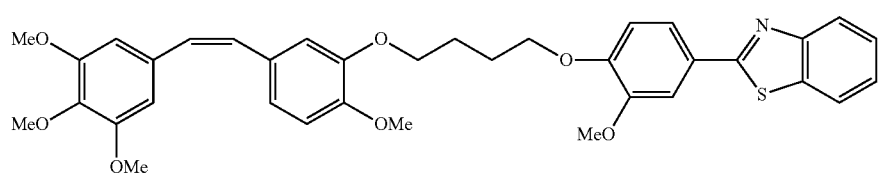
9c
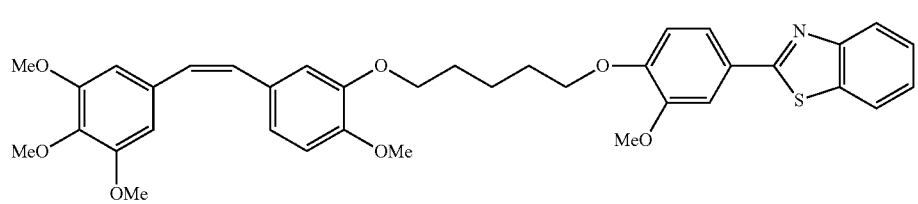
9d
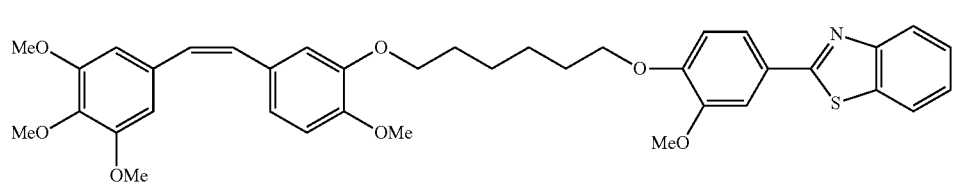
9e
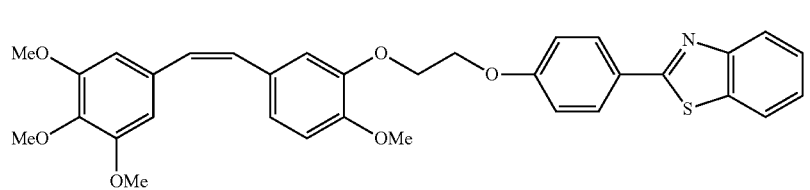
9f
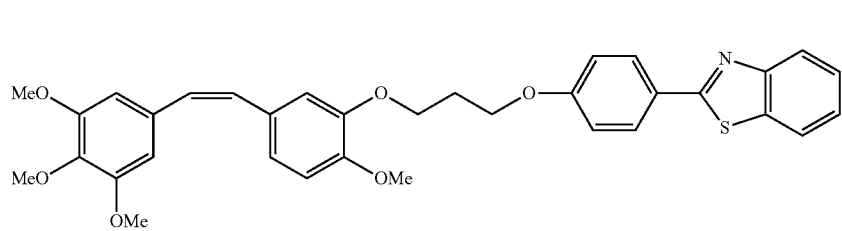
9g
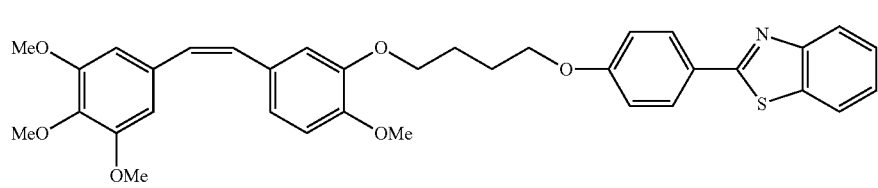
9h
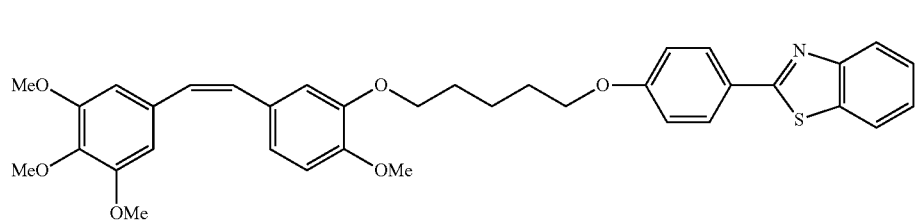
9i -continued
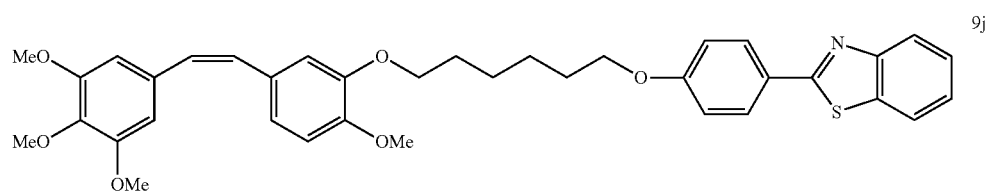
9j
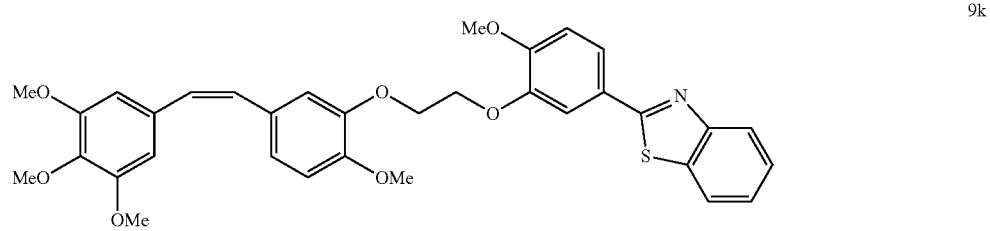
9k
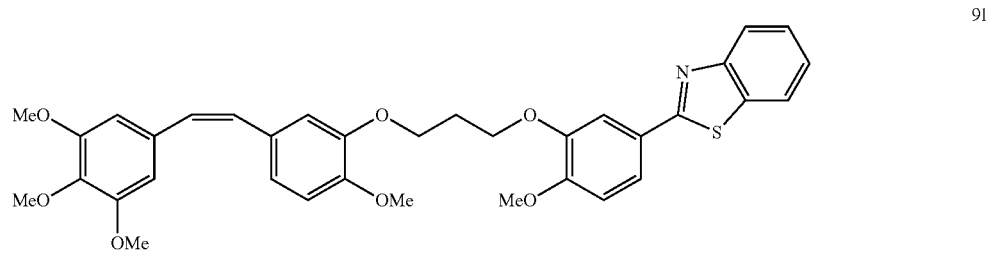
9l
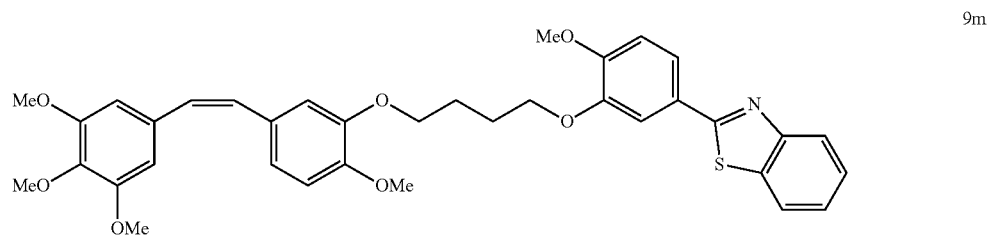
9m
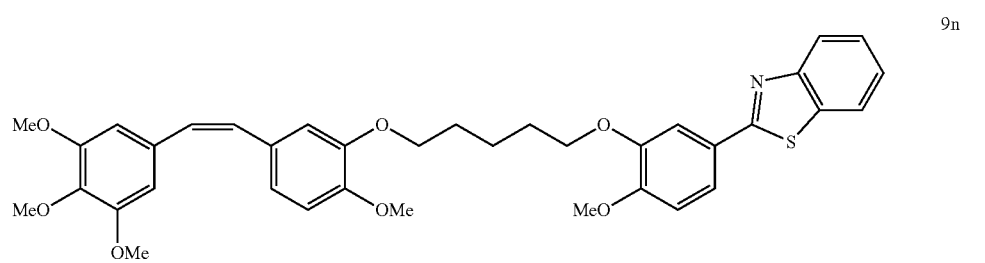
9n
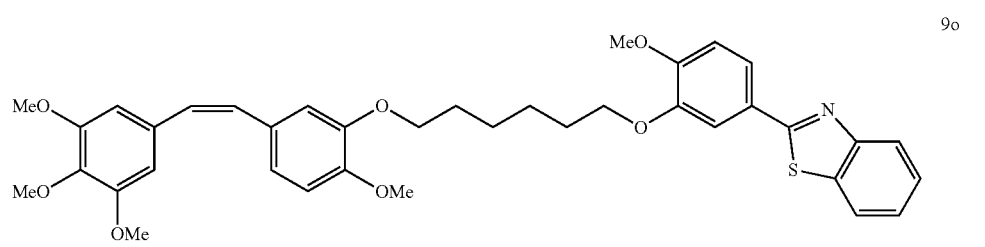
9o
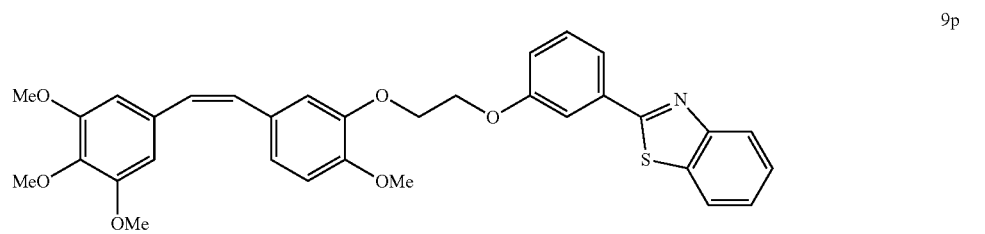
9p -continued
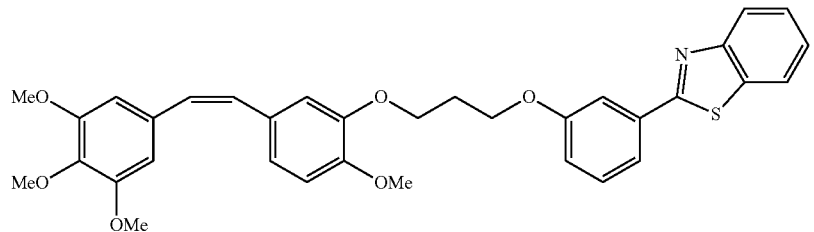
9q
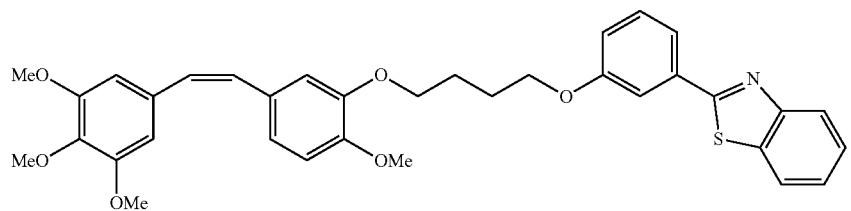
9r
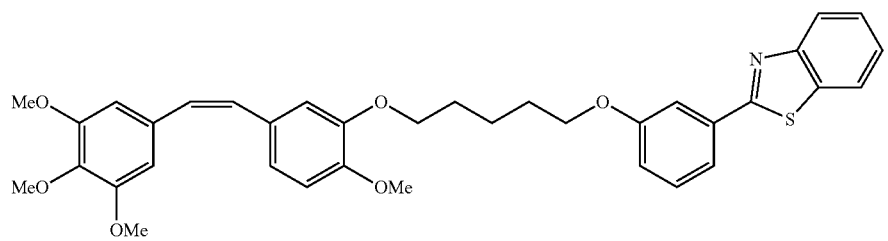
9s
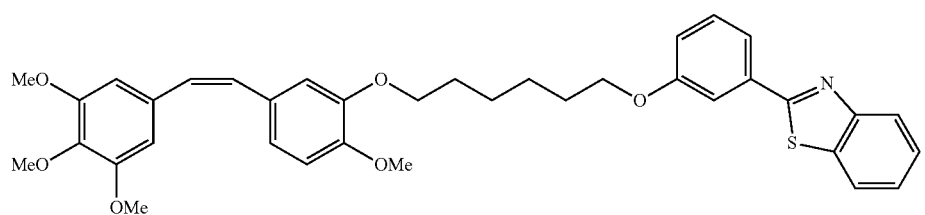
9t
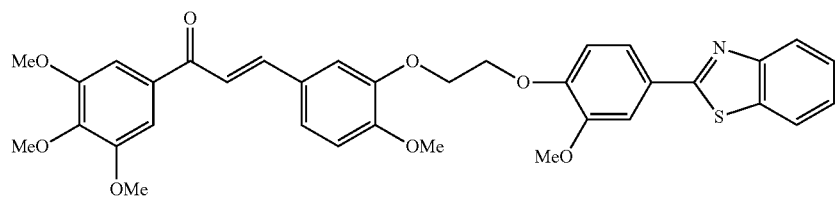
10a
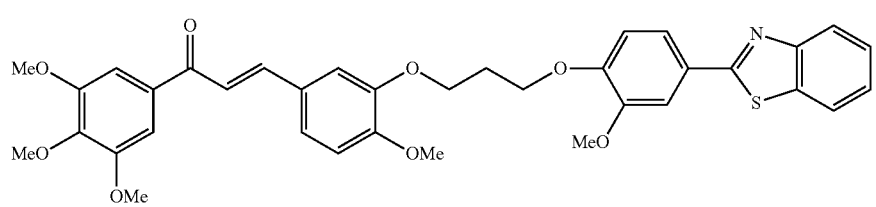
10b
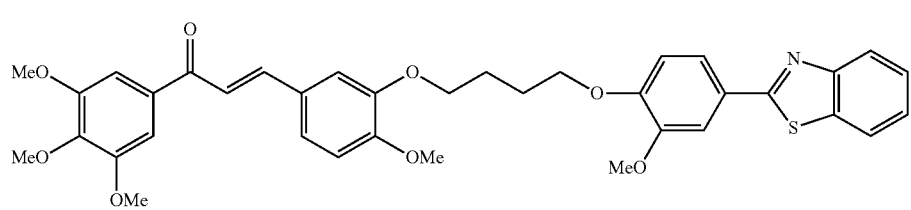
10c -continued
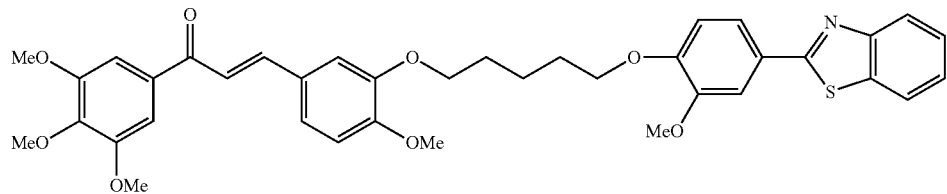
10d
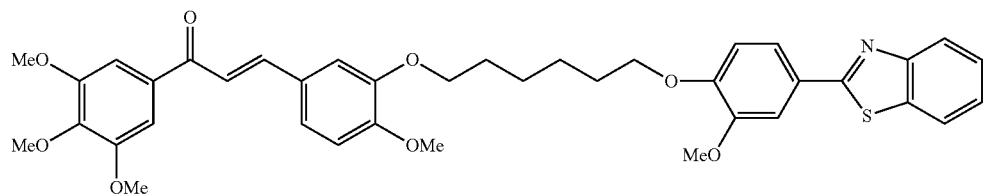
10e
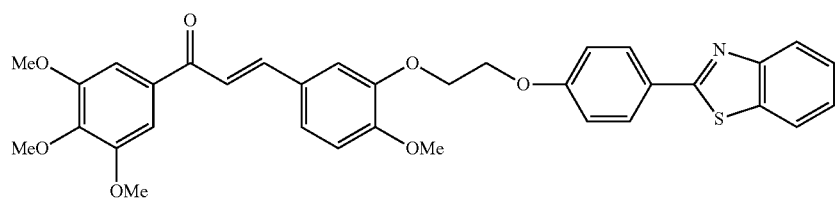
10f
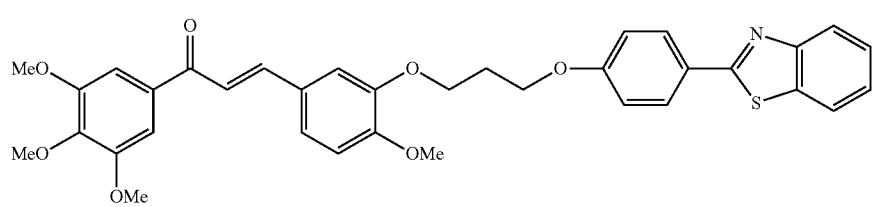
10g
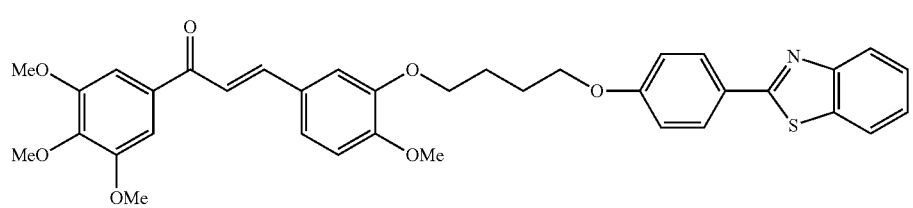
10h
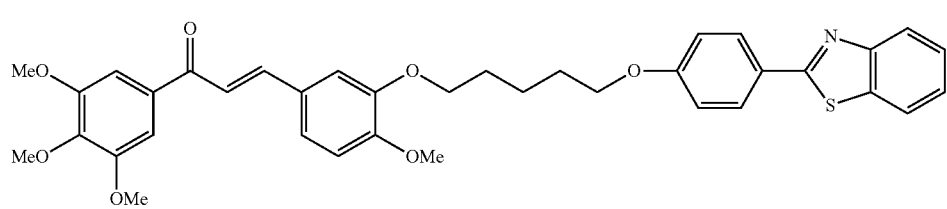
10i
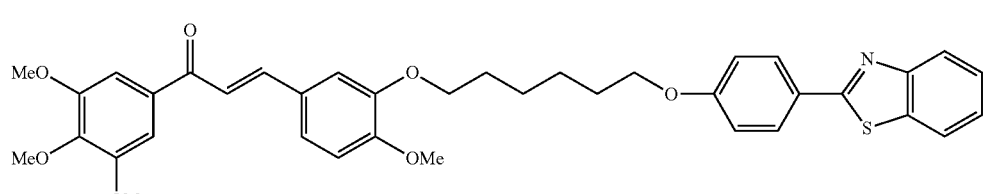
10j
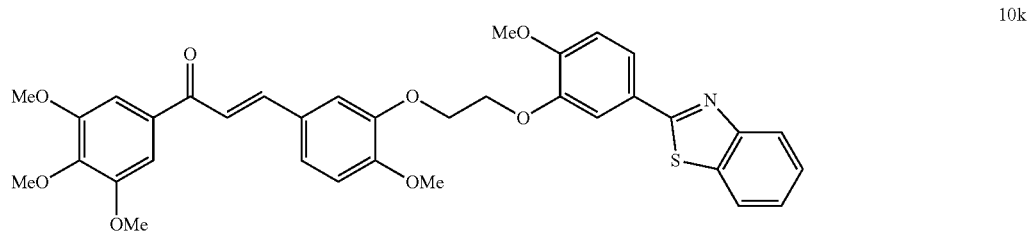
10k -continued
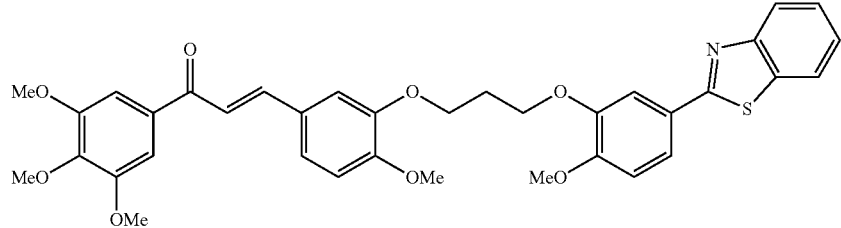
10l
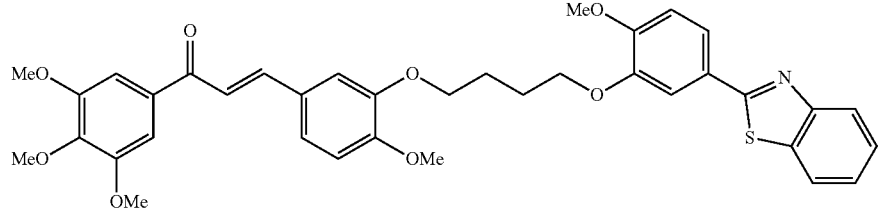
10m
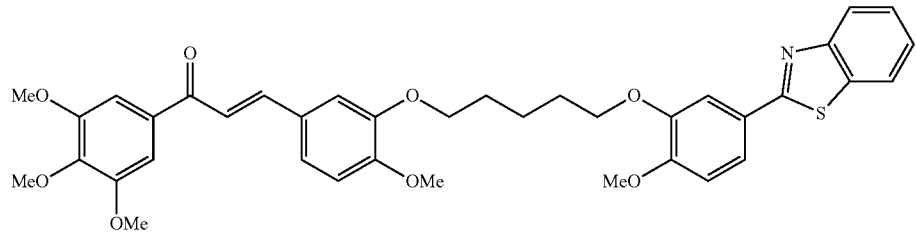
10n
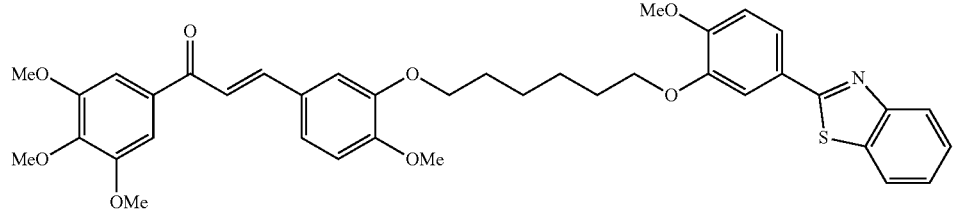
10o
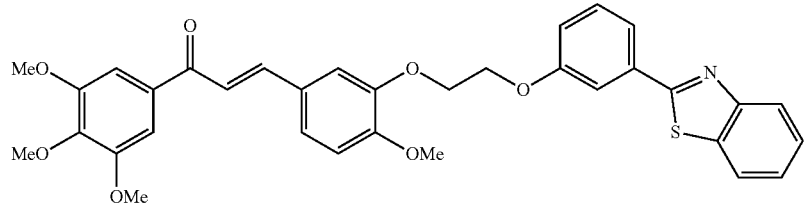
10p
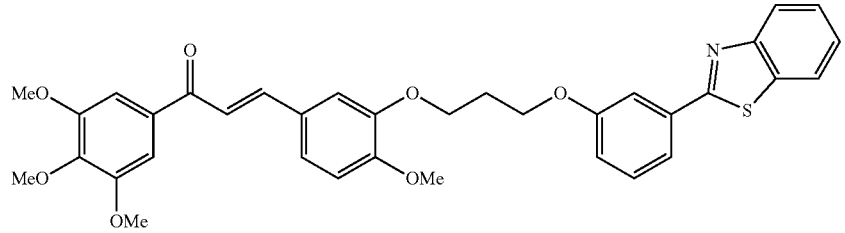
10q
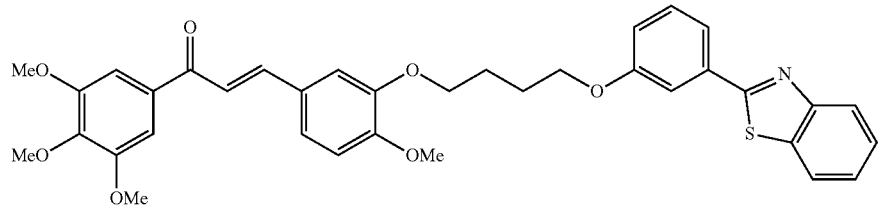
10r

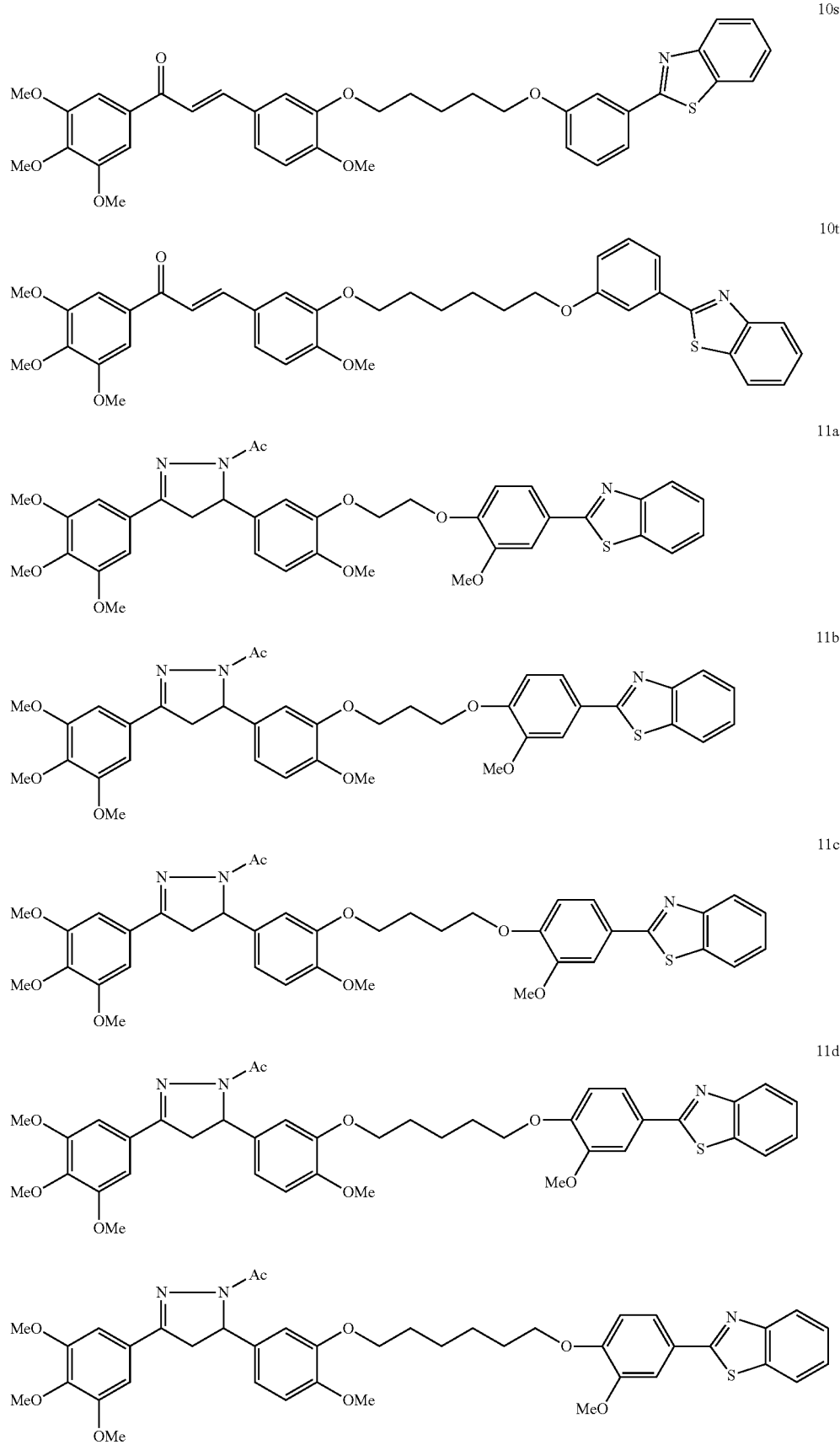

-continued
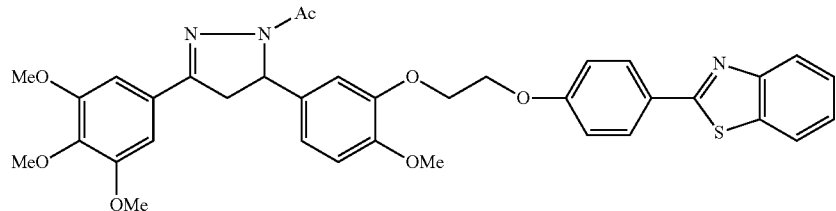
11f
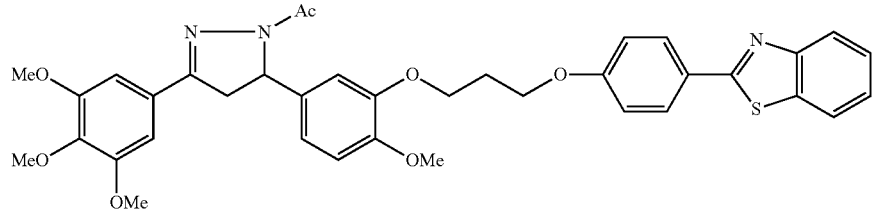
11g
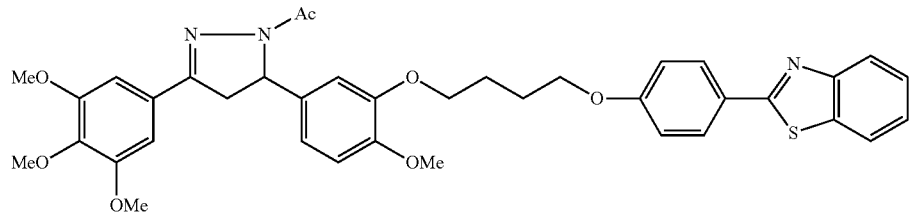
11h
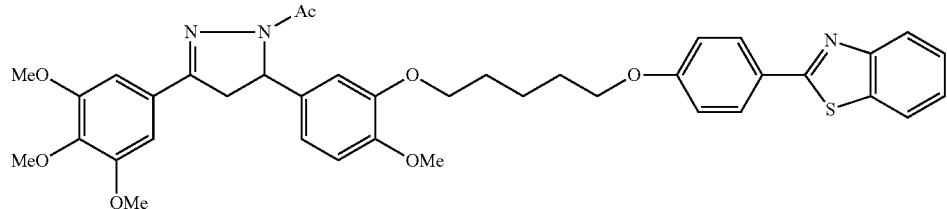
11i
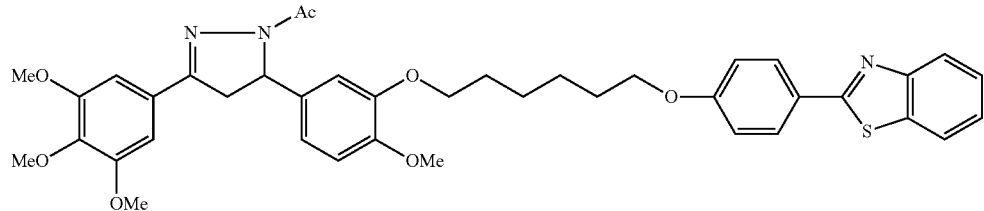
11j
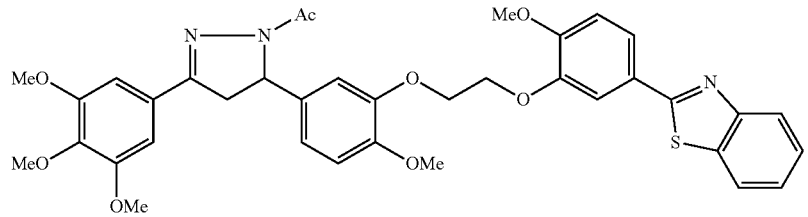
11k
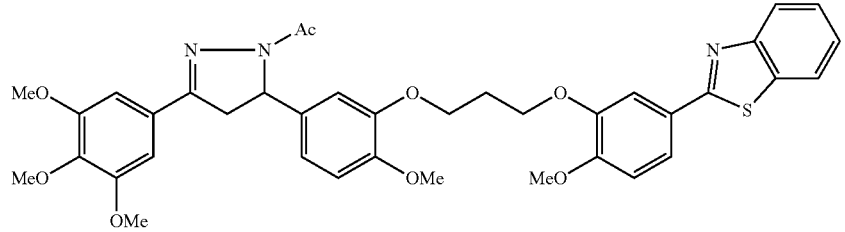
11l

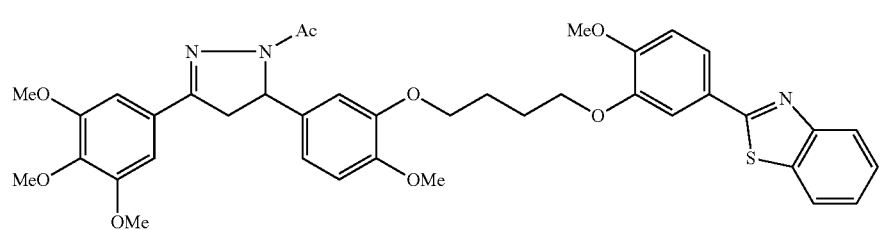
11m
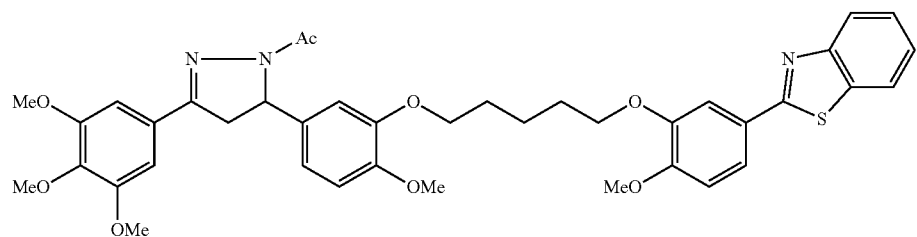
11n
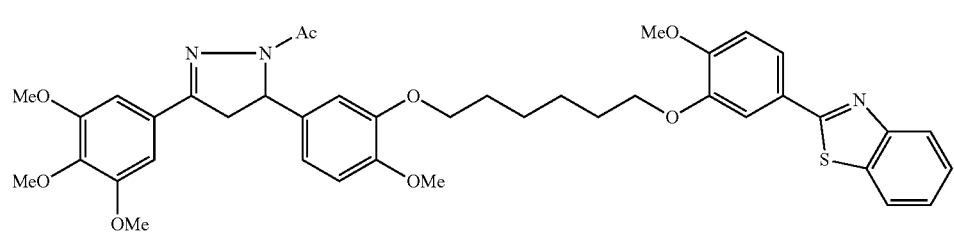
11o
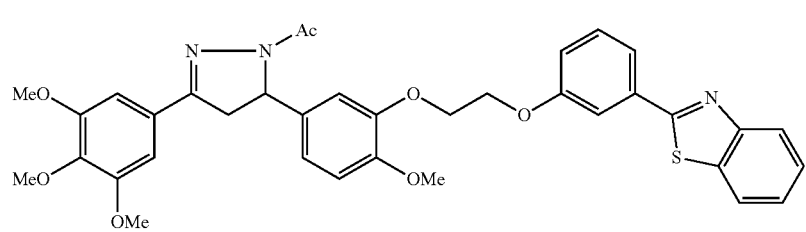
11p
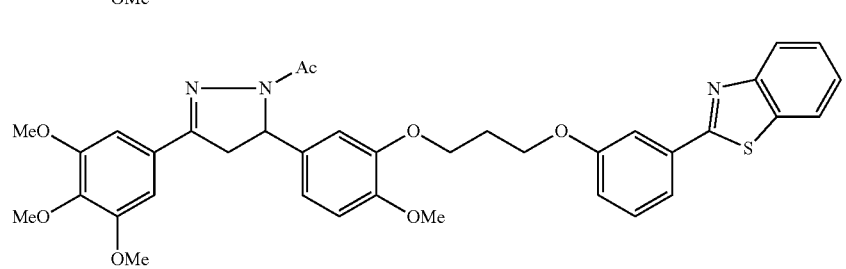
11q
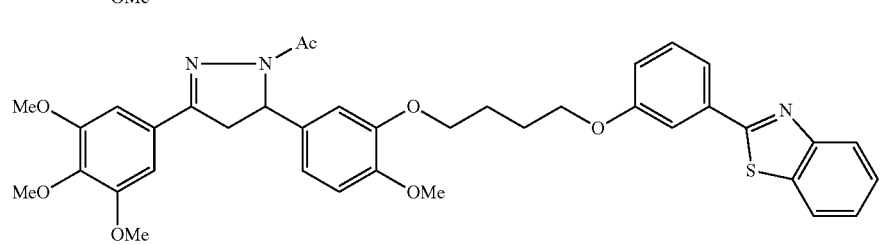
11r
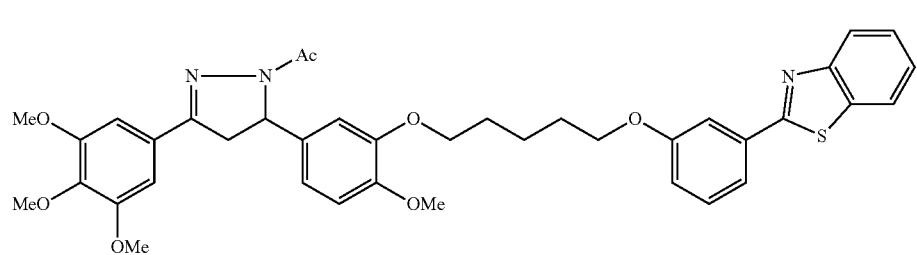
11s -continued
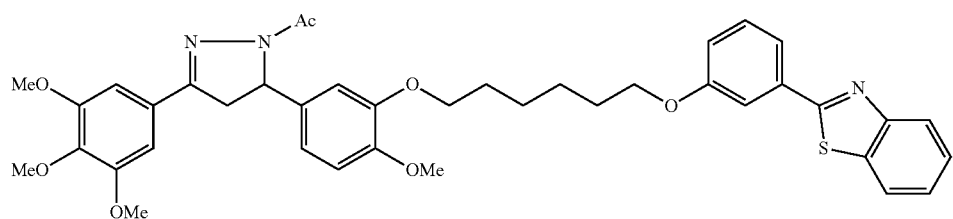
11t
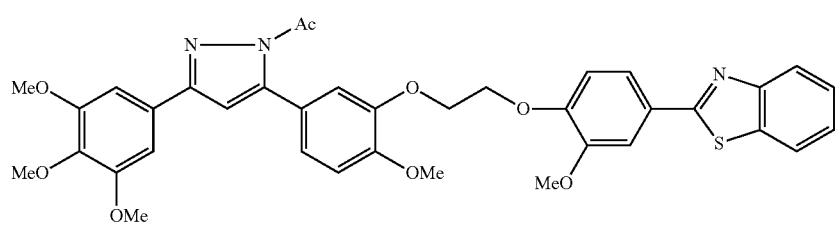
12a
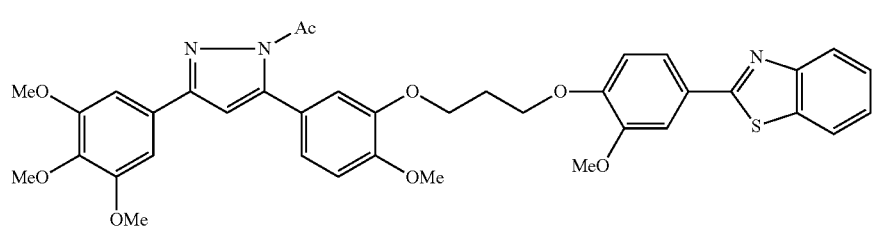
12b
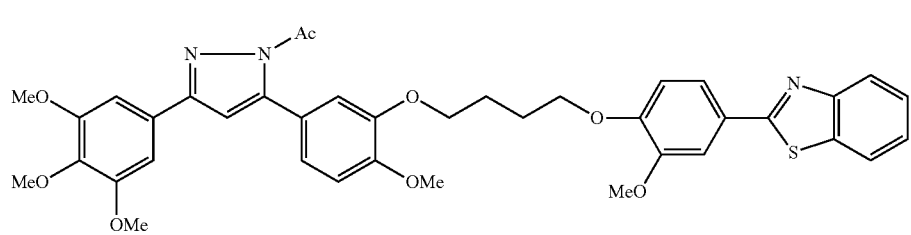
12c
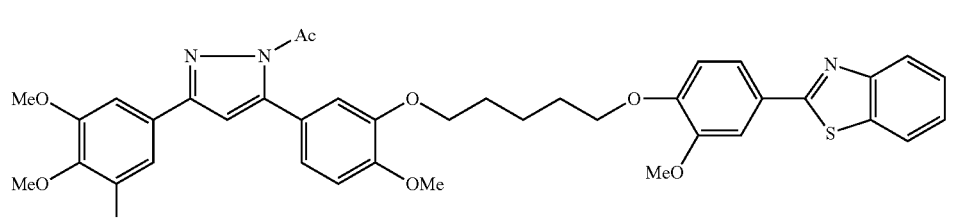
12d
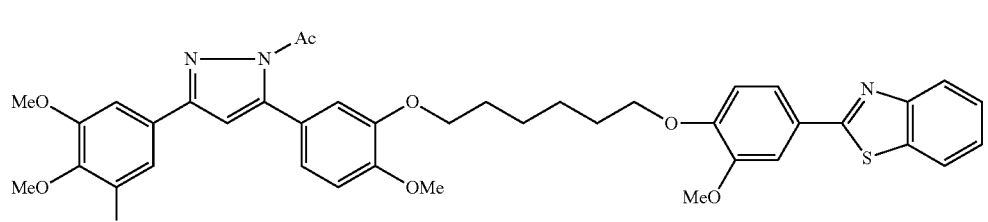
12e
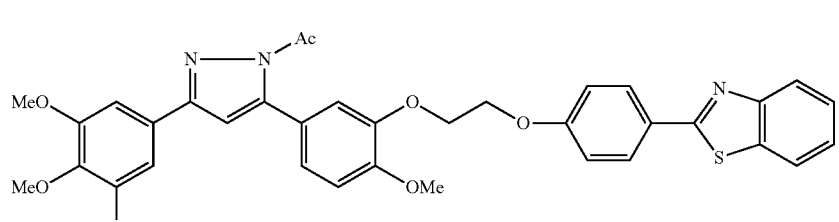
12f -continued
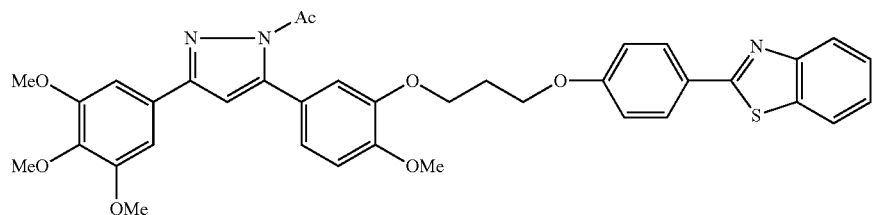
12g
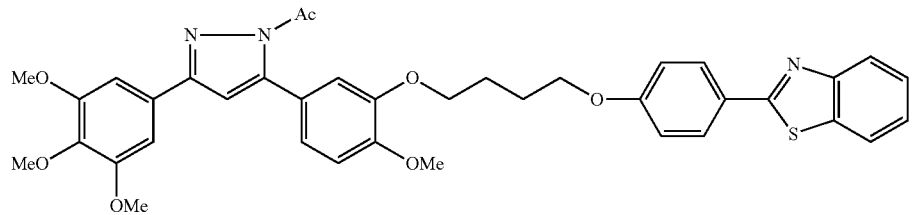
12h
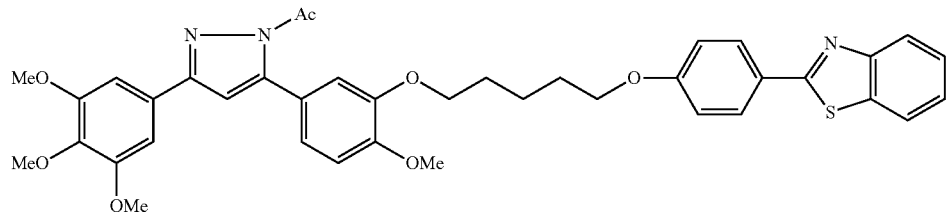
12i
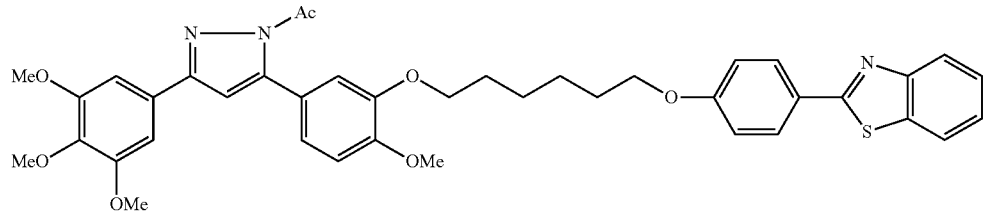
12j
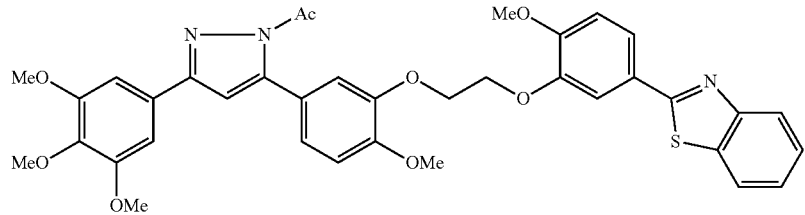
12k
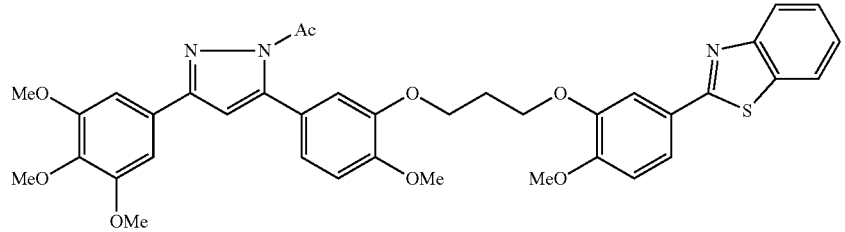
12l
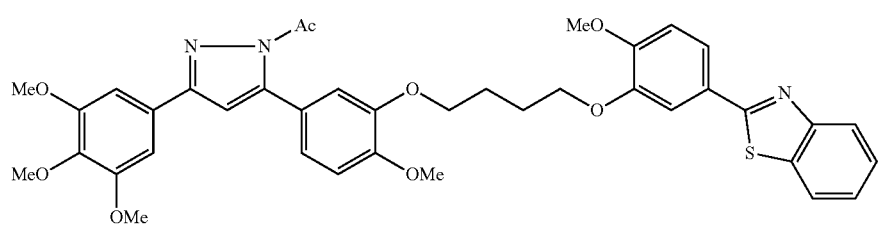
12m -continued
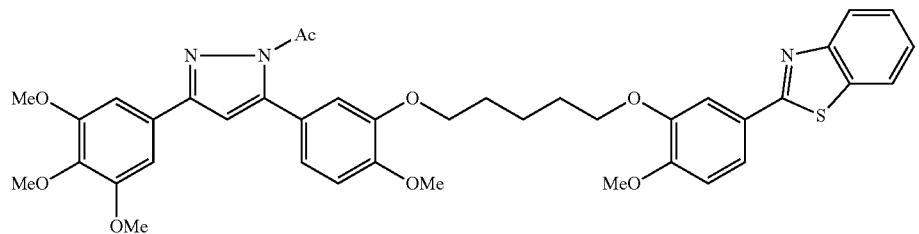
12n
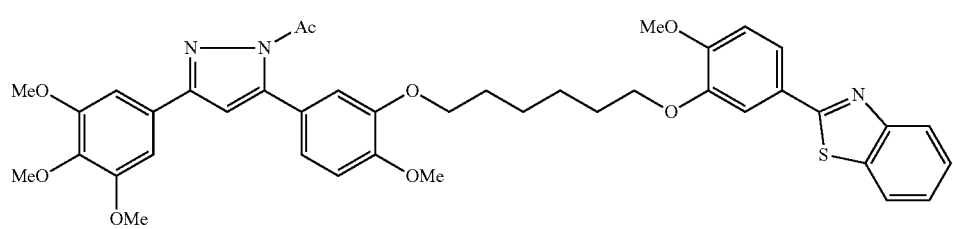
12o
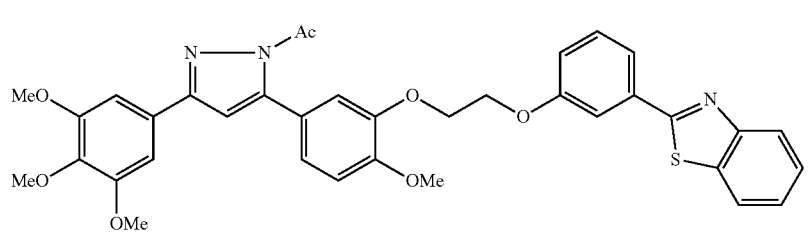
12p
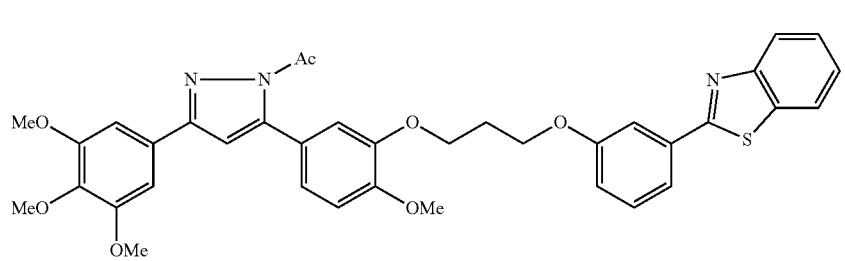
12q
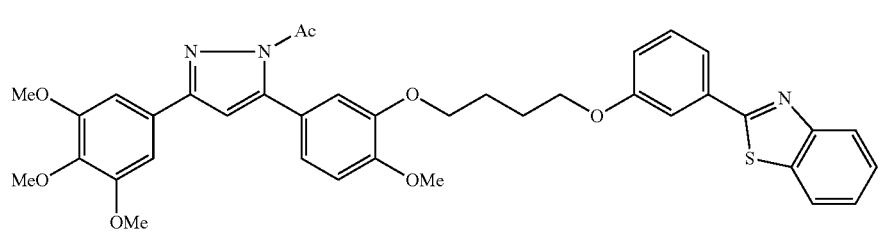
12r
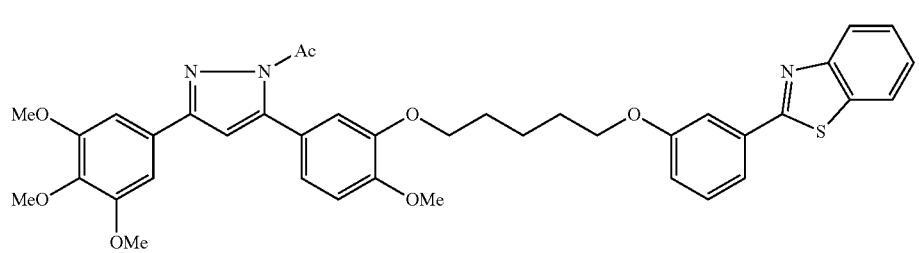
12s
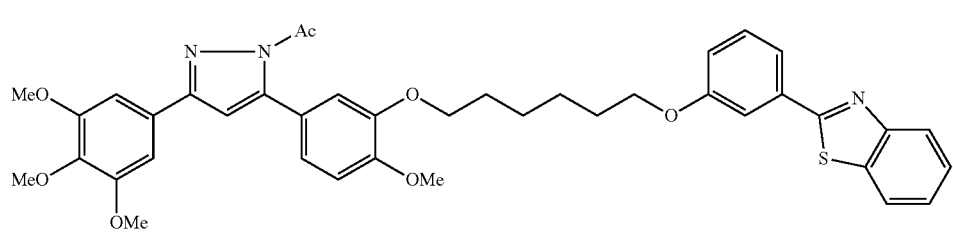
12t -continued
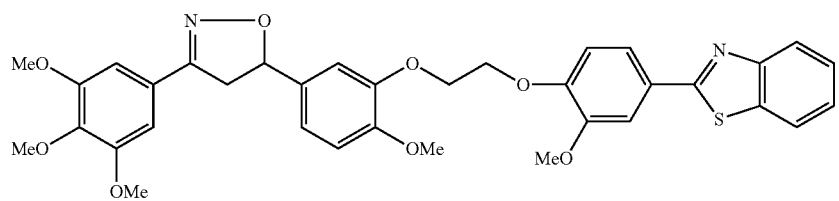
13a
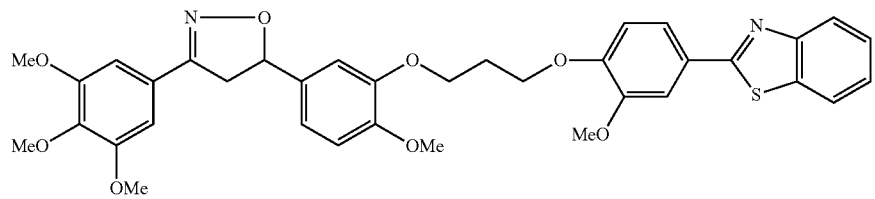
13b
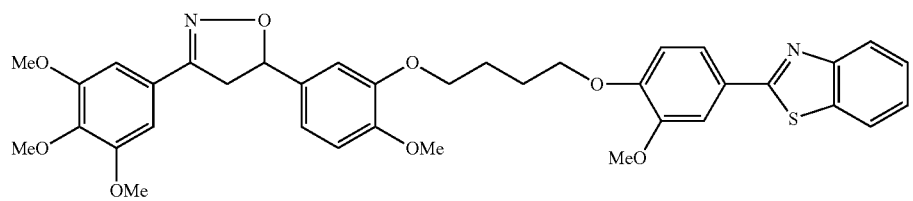
13c
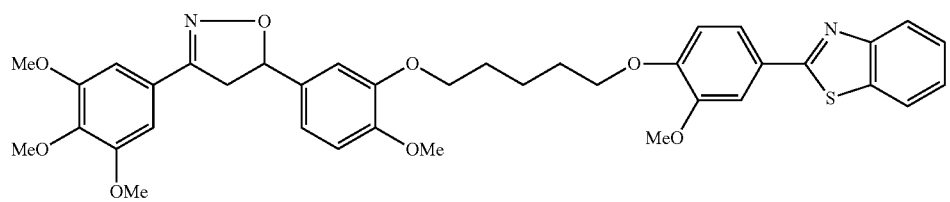
13d
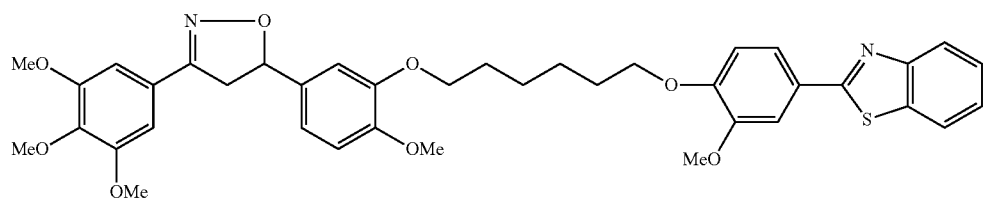
13e
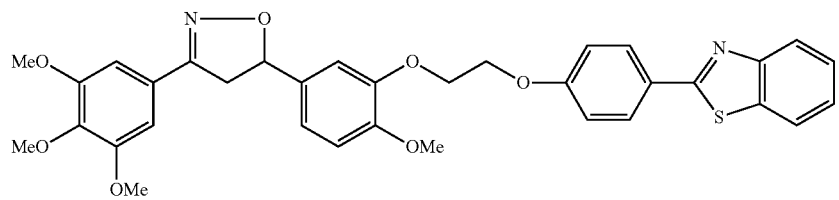
13f
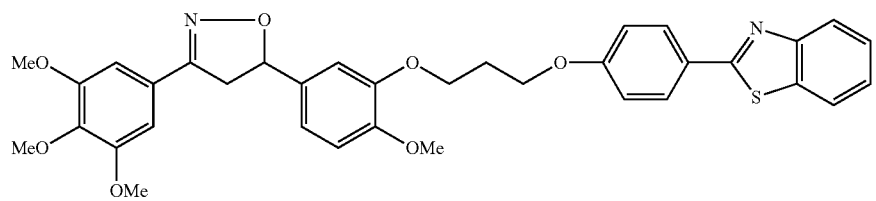
13g
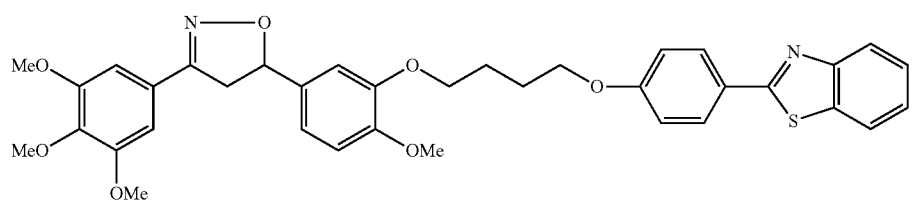
13h -continued
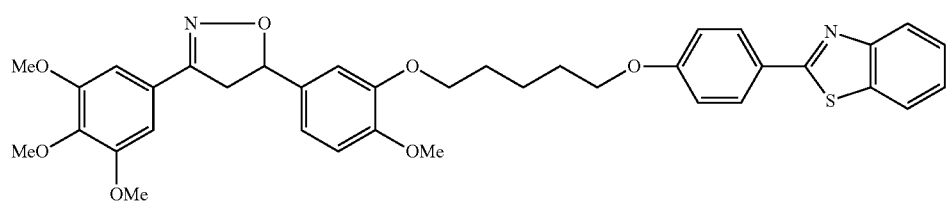
13i
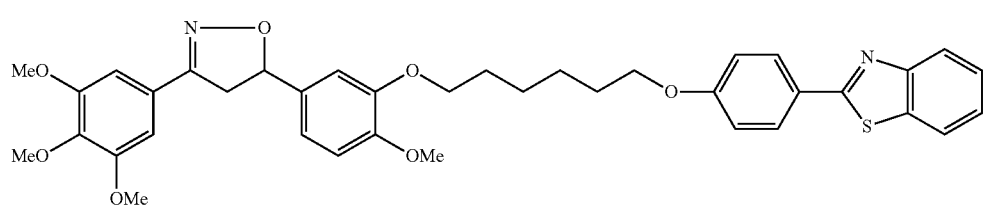
13j
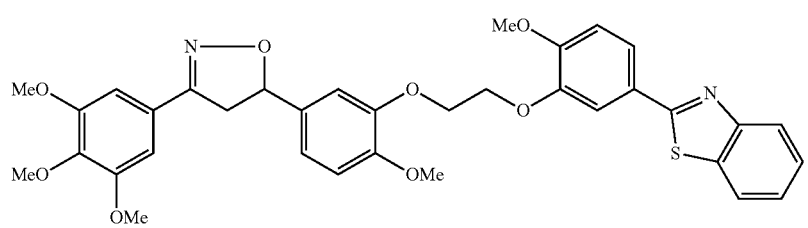
13k
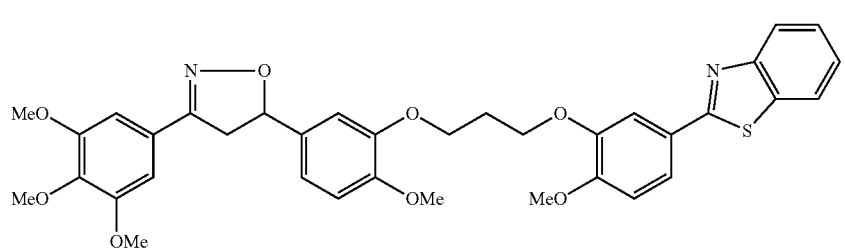
13l
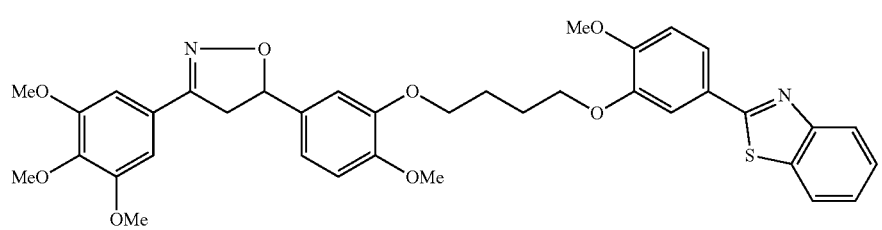
13m
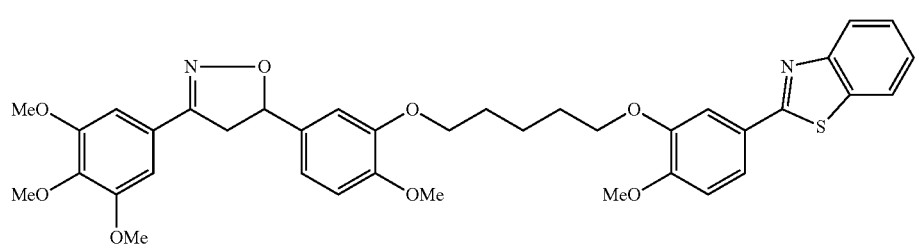
13n
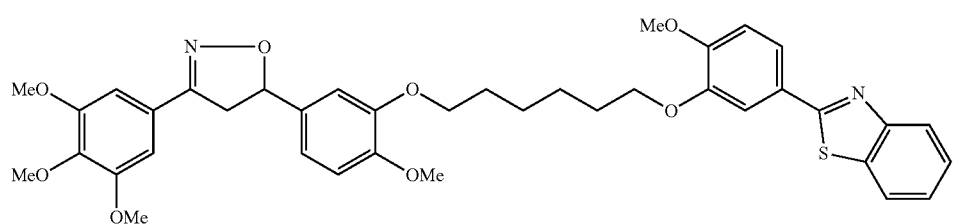
13o -continued
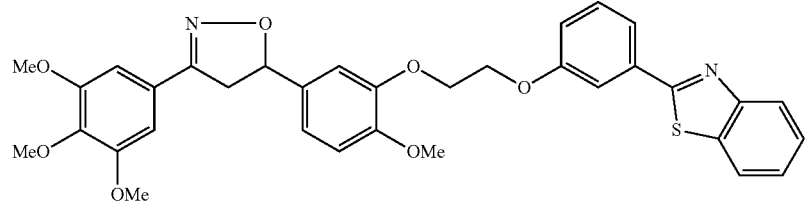
13p
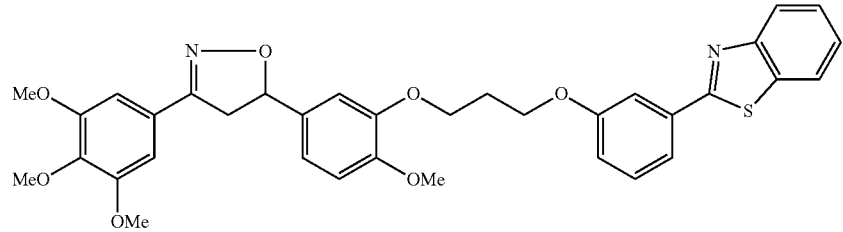
13q
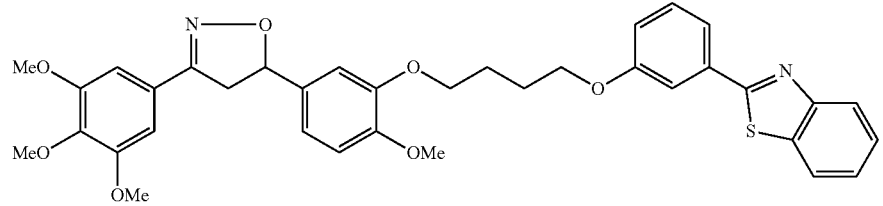
13r
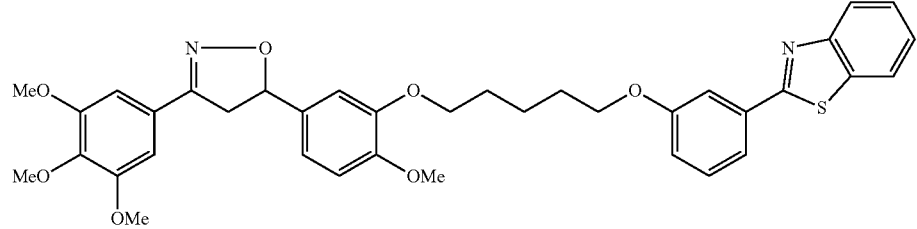
13s
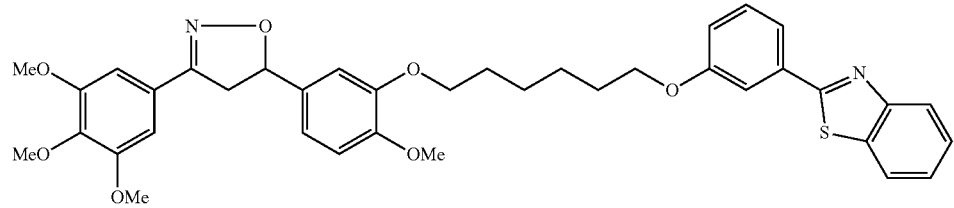
13t
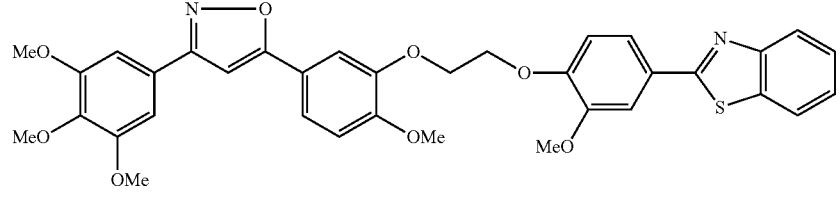
14a
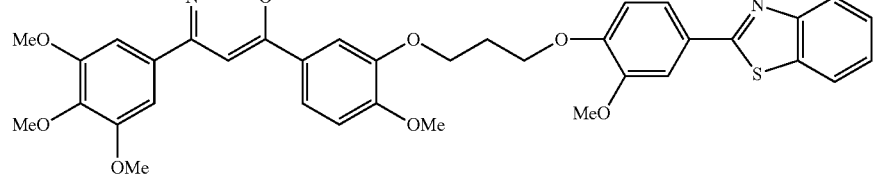
14b -continued
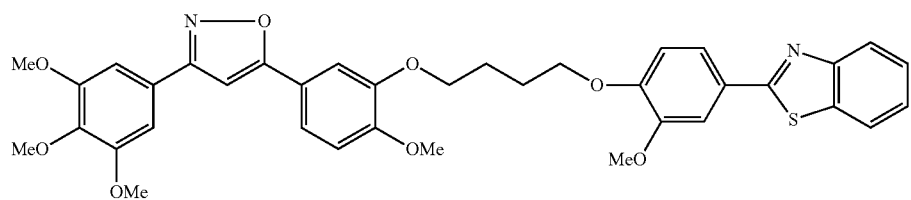
14c
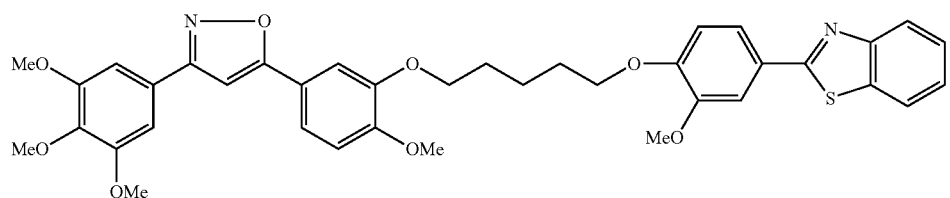
14d
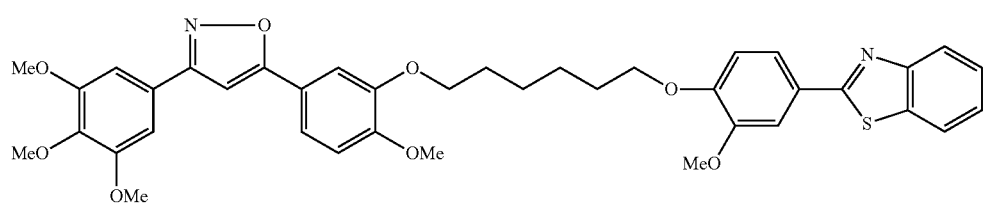
14e
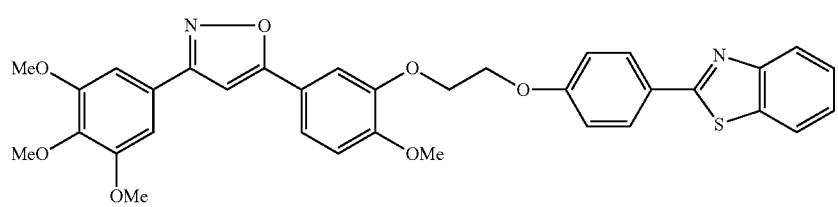
14f
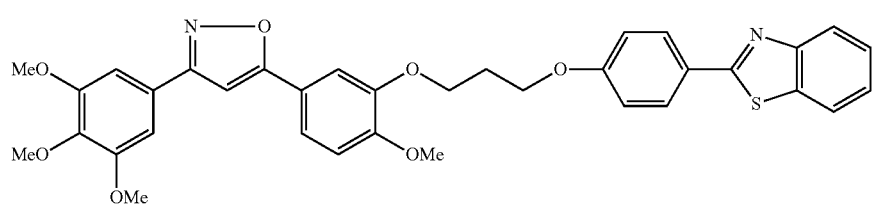
14g
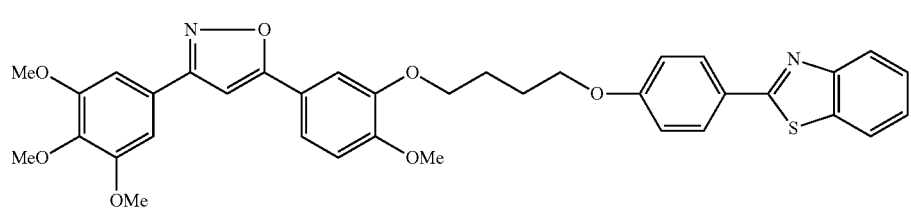
14h
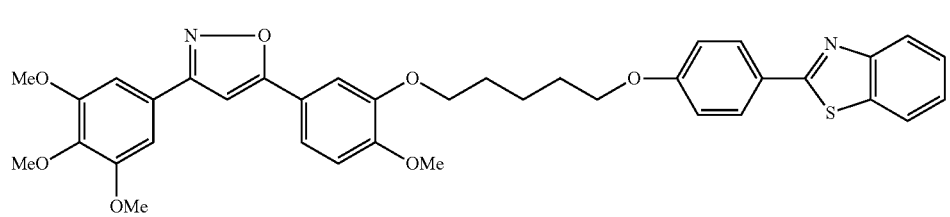
14i
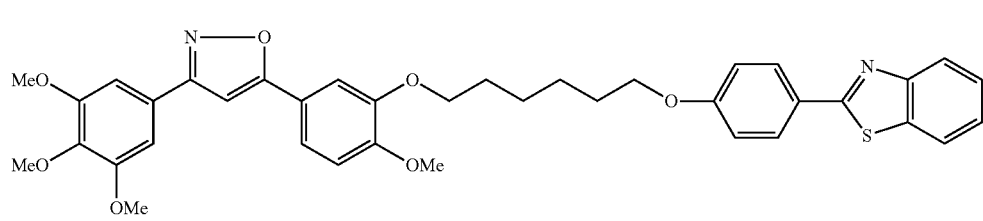
14j

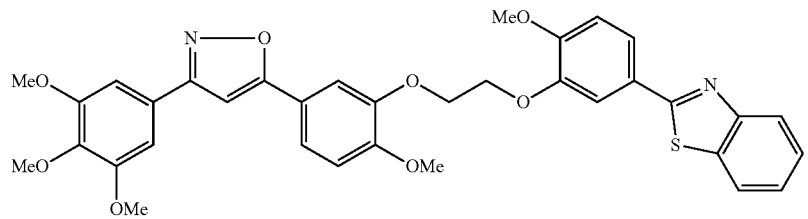
14k
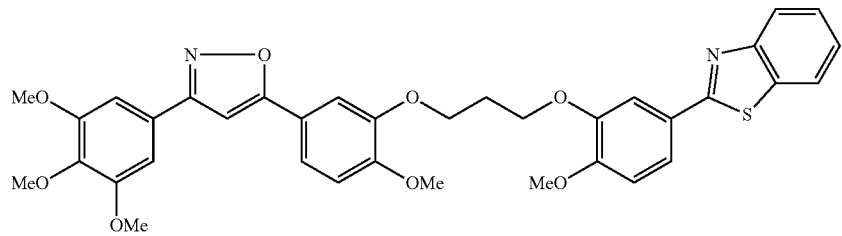
14l
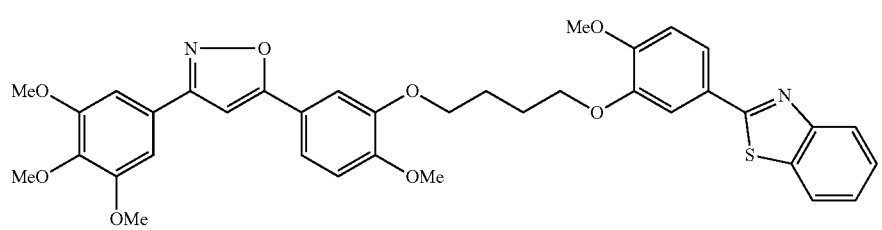
14m
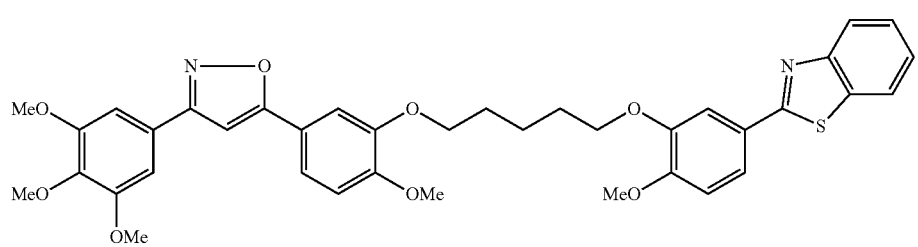
14n
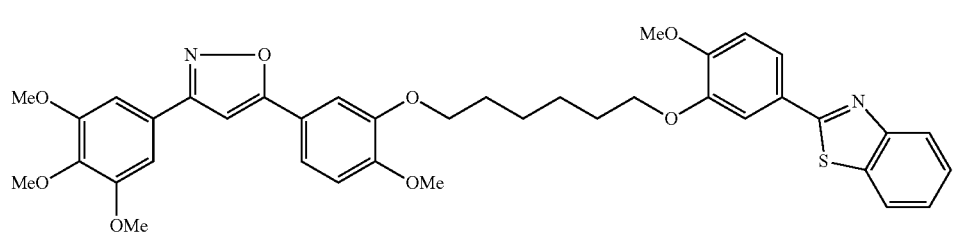
14o
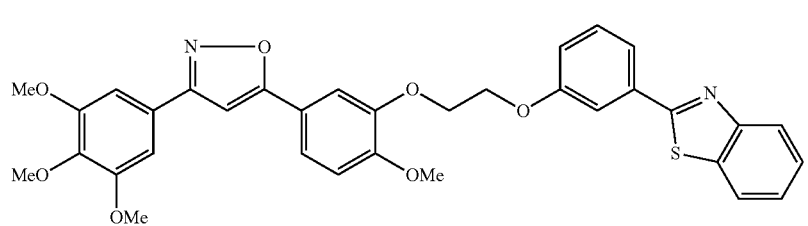
14p
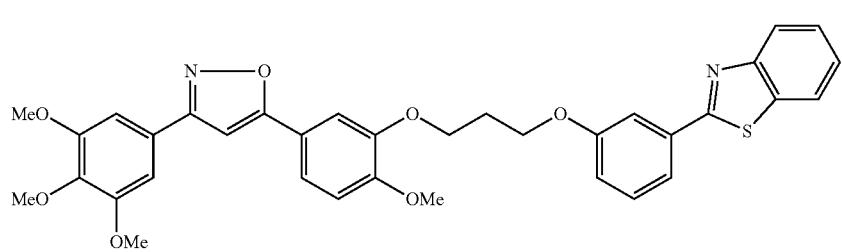
14q -continued
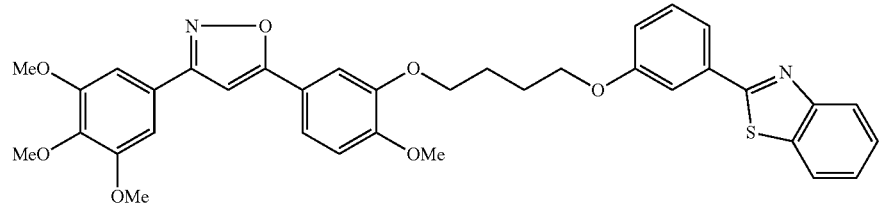
14r
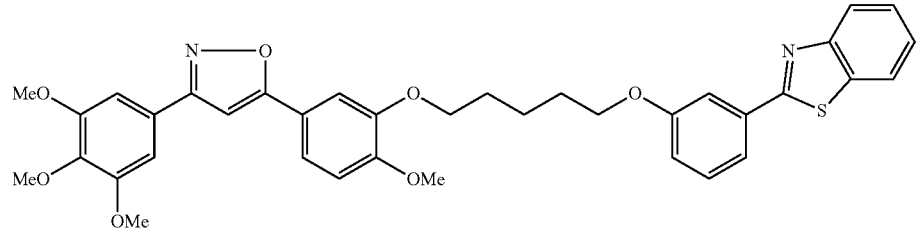
14s
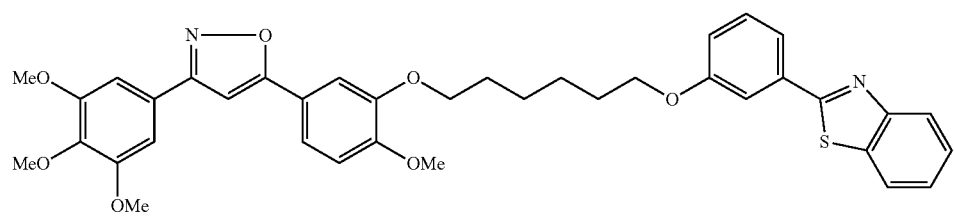
14t
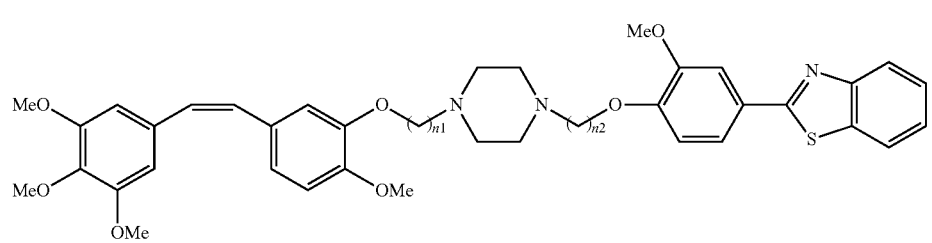
15a
n1 & n2 = 2
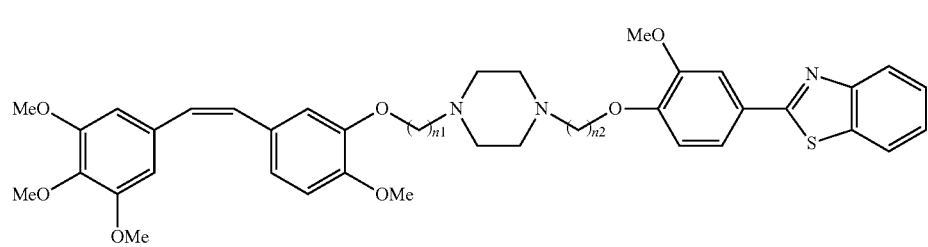
15b
n1 & n2 = 3
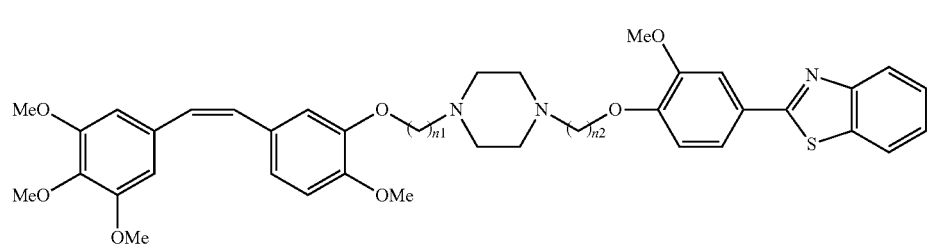
15c
n1 & n2 = 4

-continued
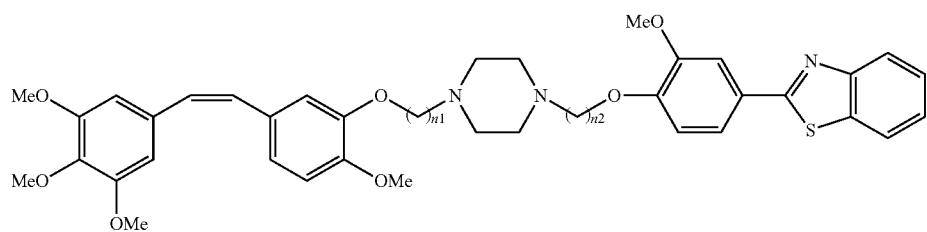
15d
n1 & n2 = 5
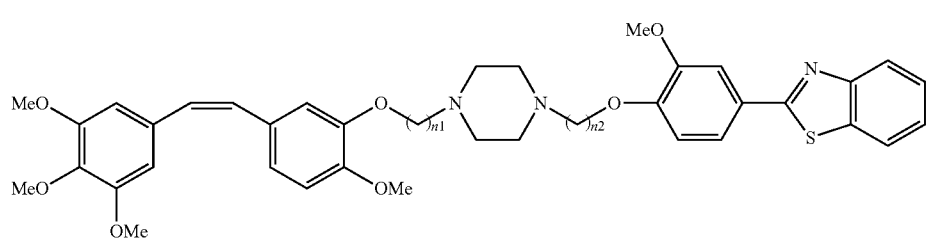
15e
n1 & n2 = 6
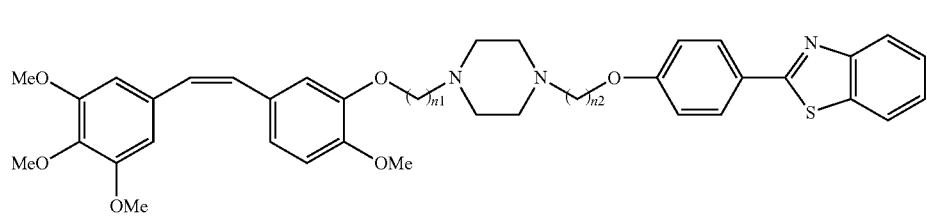
15f
n1 & n2 = 2
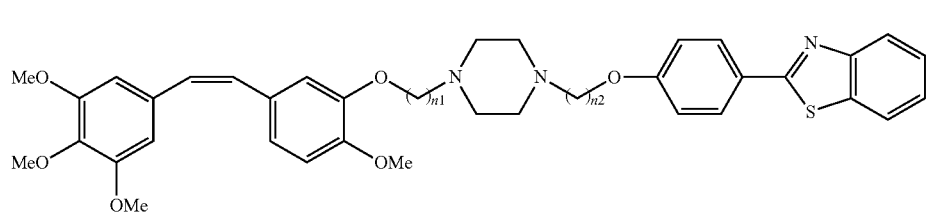
15g
n1 & n2 = 3
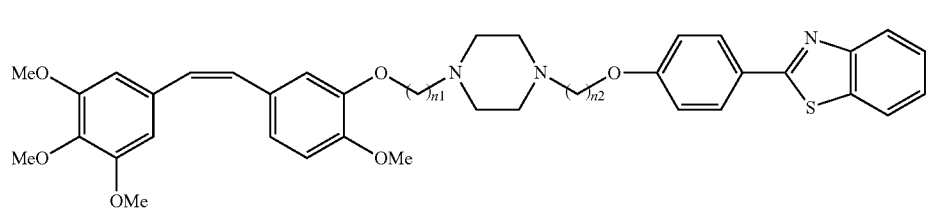
15h
n1 & n2 = 4
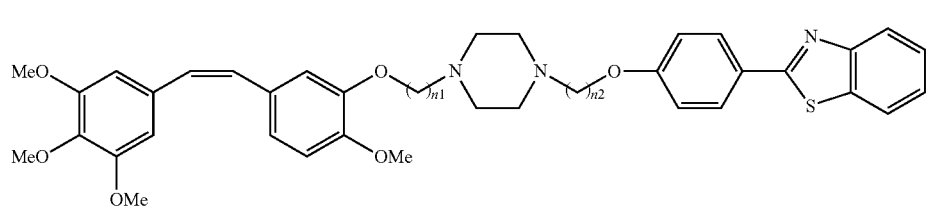
15i
n1 & n2 = 5

-continued
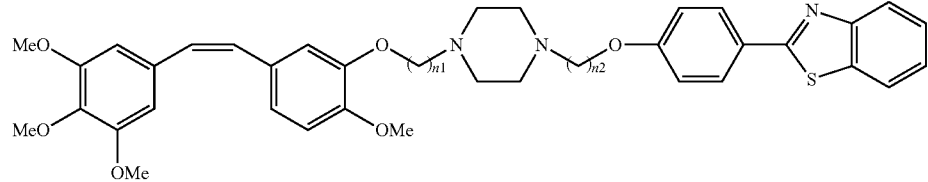
15j
n1 & n2 = 6
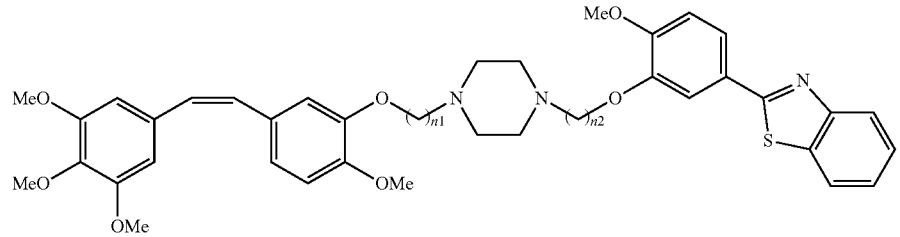
15k
n1 & n2 = 2
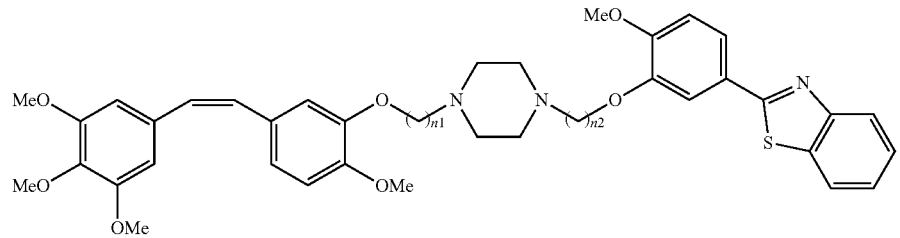
15l
n1 & n2 = 3
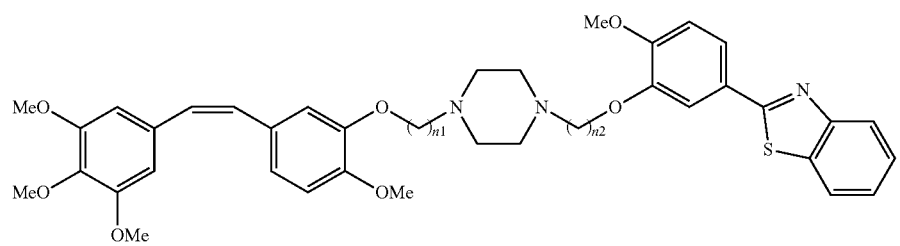
15m
n1 & n2 = 4
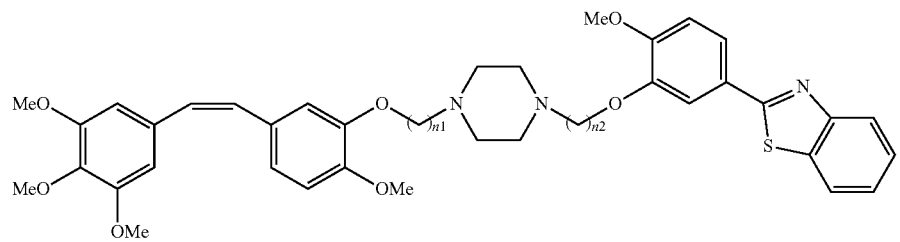
15n
n1 & n2 = 5
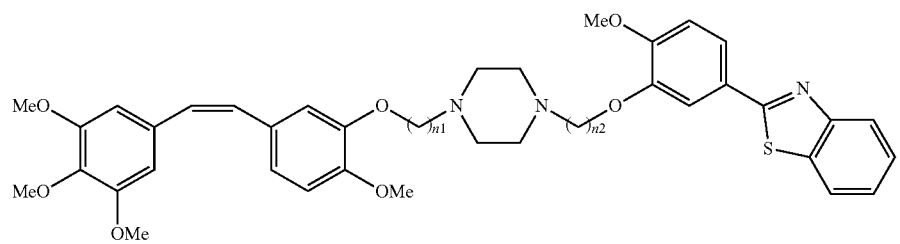
15o
n1 & n2 = 6

-continued
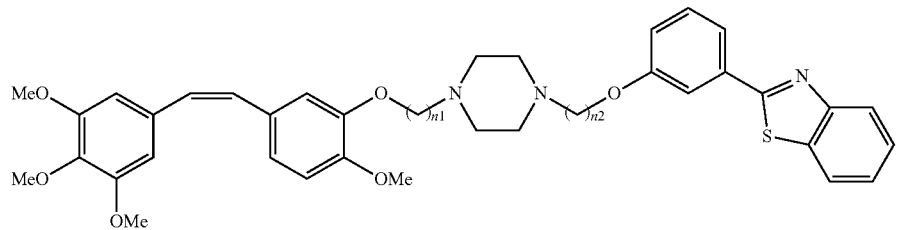
15p
n1 & n2 = 2
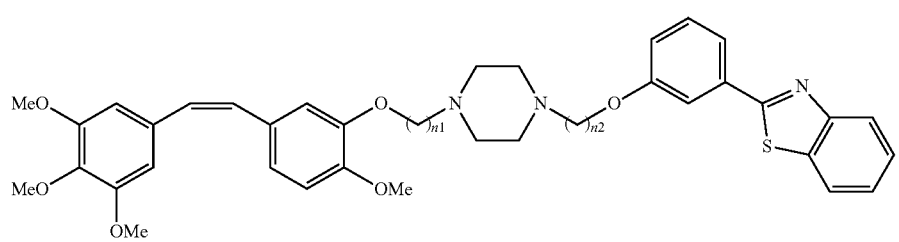
15q
n1 & n2 = 3
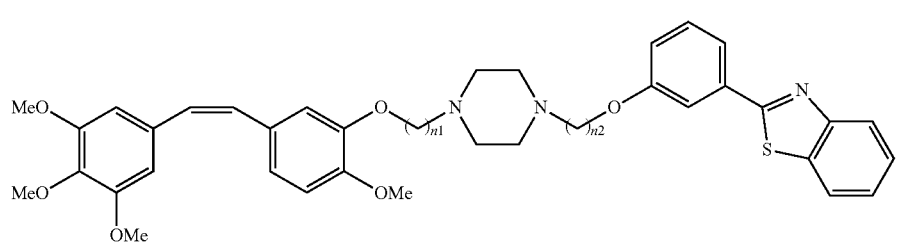
15r
n1 & n2 = 4
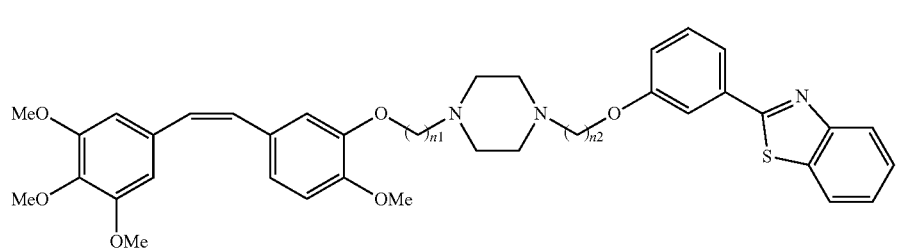
15s
n1 & n2 = 5
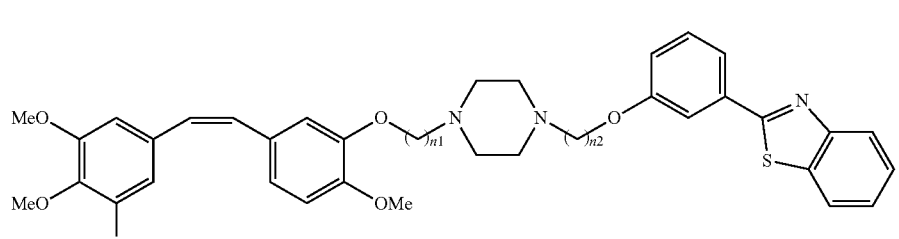
15t
n1 & n2 = 6
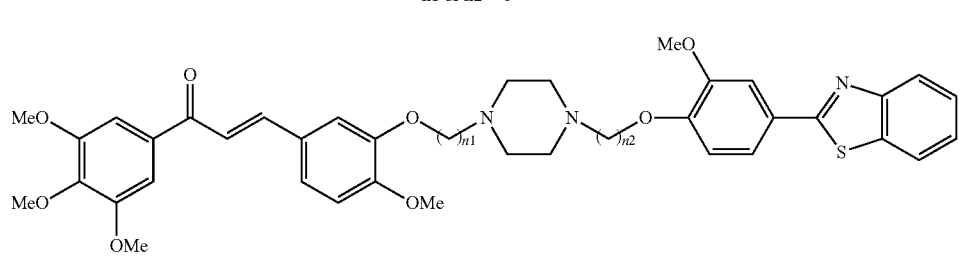
16a
n1 & n2 = 2

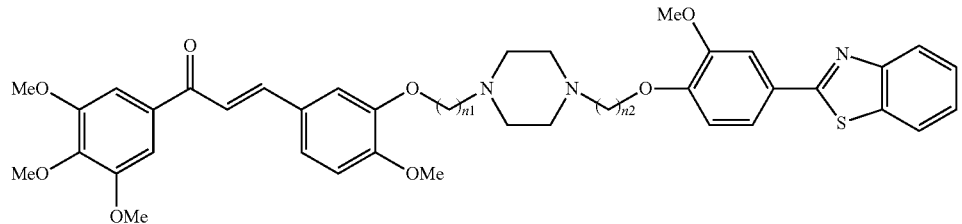
16b
n1 & n2 = 3
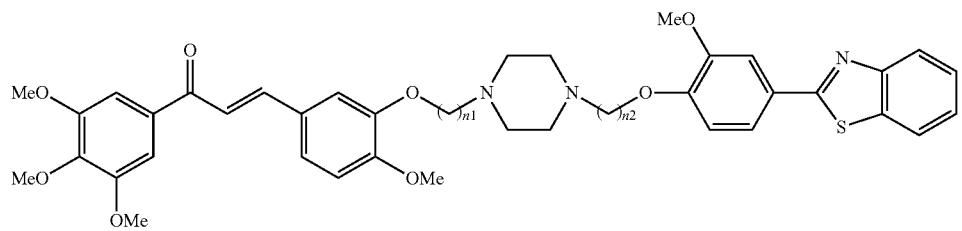
16c
n1 & n2 = 4
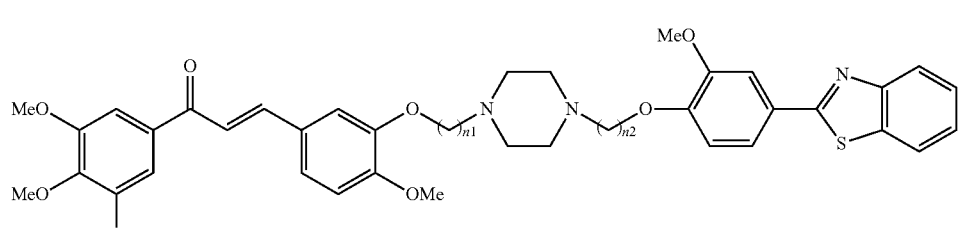
16d
n1 & n2 = 5
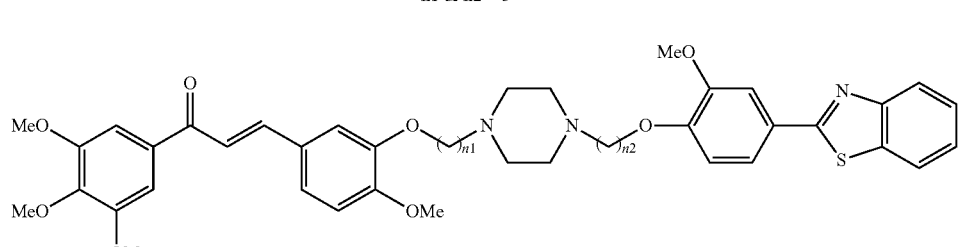
16e
n1 & n2 = 6
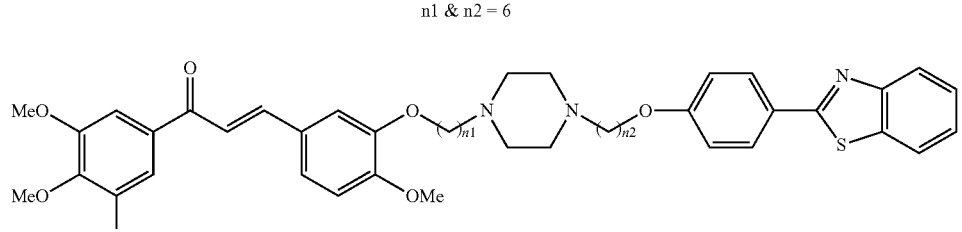
16f
n1 & n2 = 2
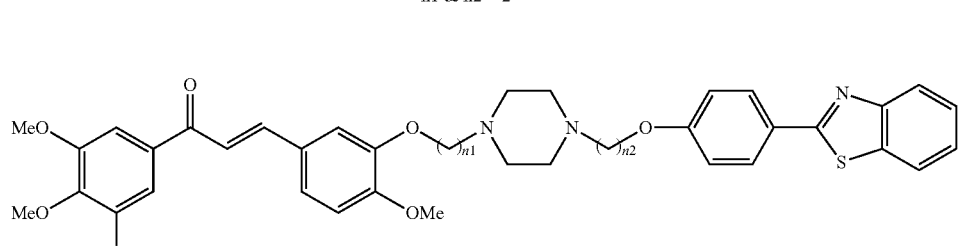
16g
n1 & n2 = 3

-continued
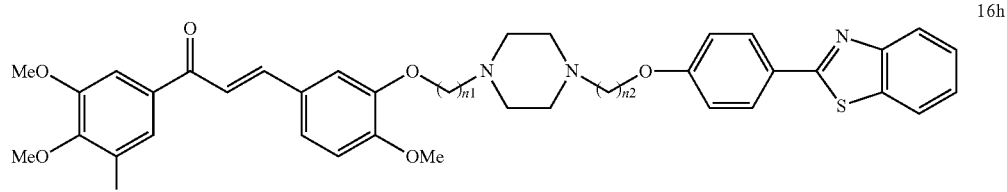
16h
n1 & n2 = 4
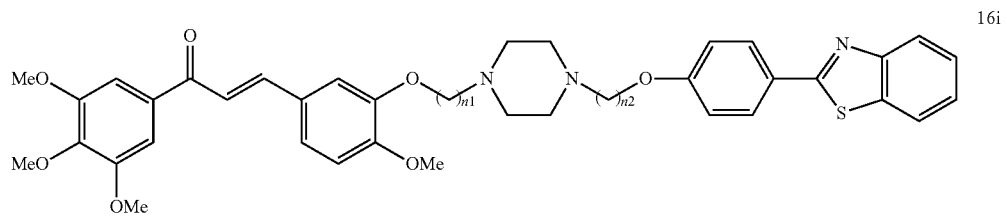
16i
n1 & n2 = 5
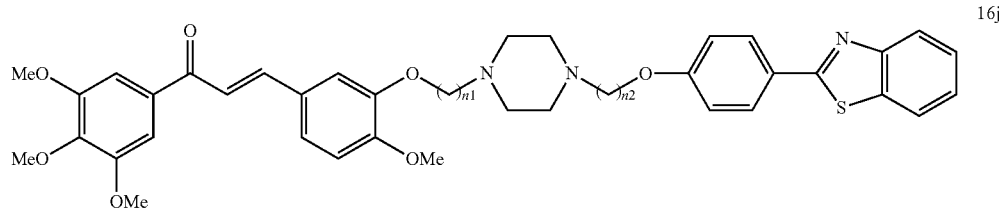
16j
n1 & n2 = 6
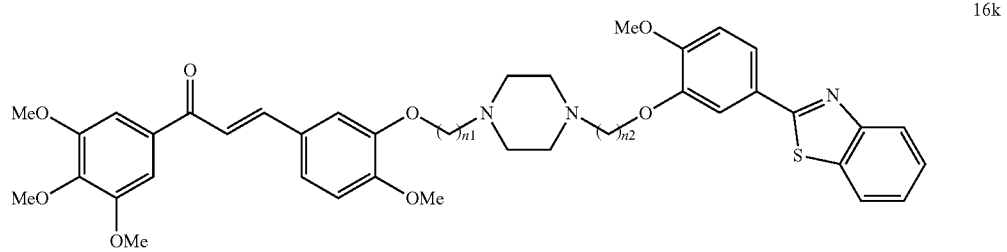
16k
n1 & n2 = 2
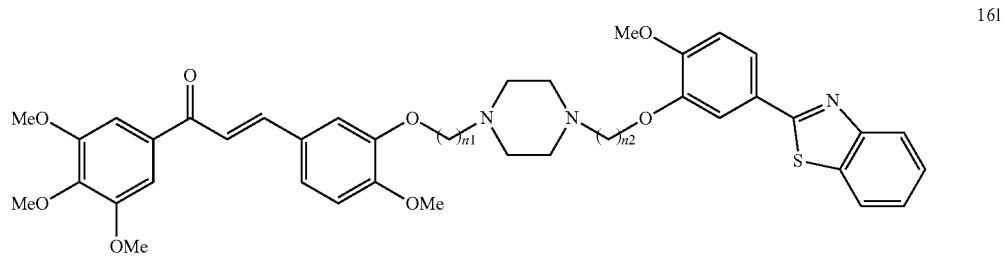
16l
n1 & n2 = 3
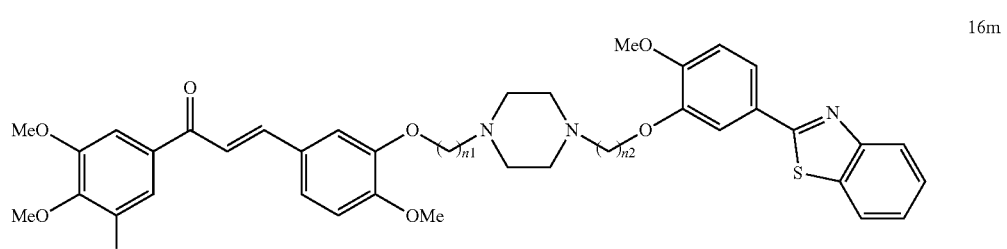
16m
n1 & n2 = 4

-continued
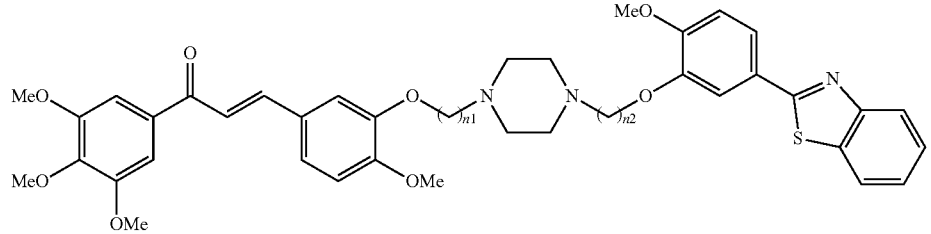
16n
n1 & n2 = 5
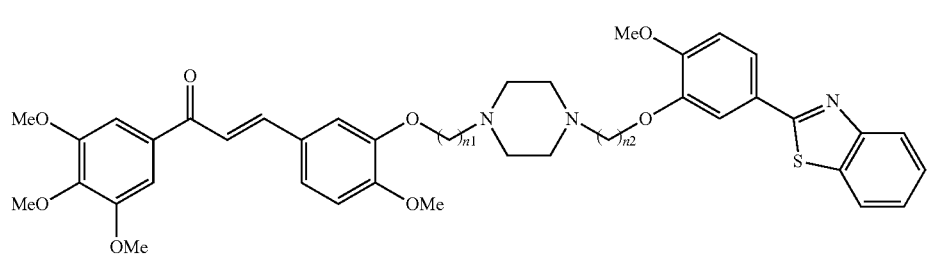
16o
n1 & n2 = 6
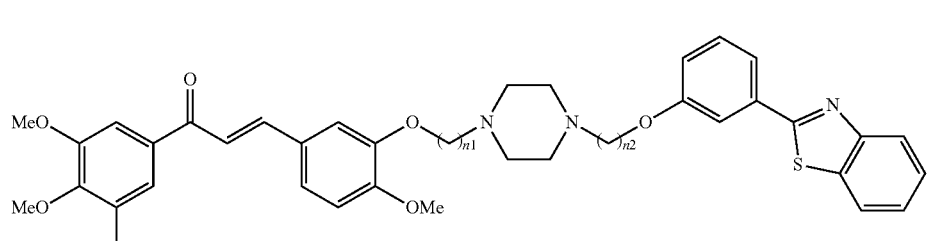
16p
n1 & n2 = 2
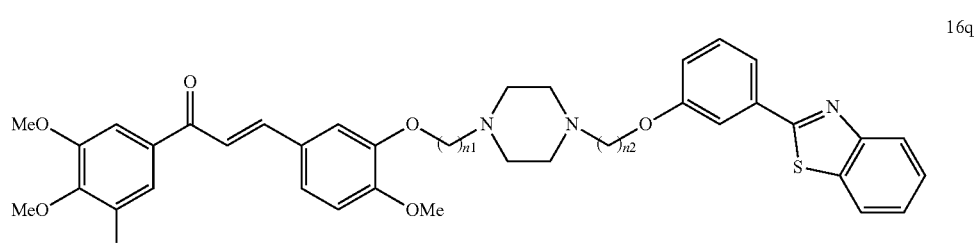
16q
n1 & n2 = 3
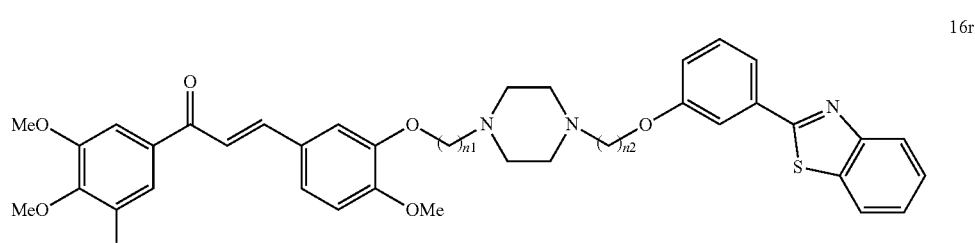
16r
n1 & n2 = 4

-continued
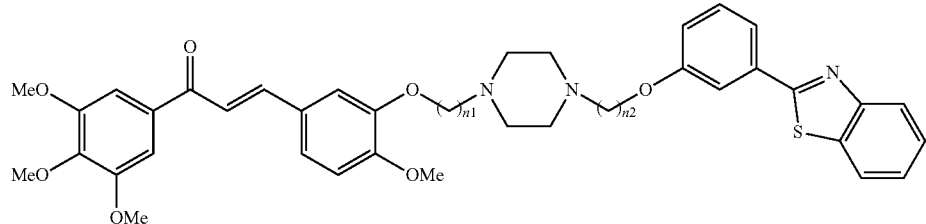
16s
n1 & n2 = 5
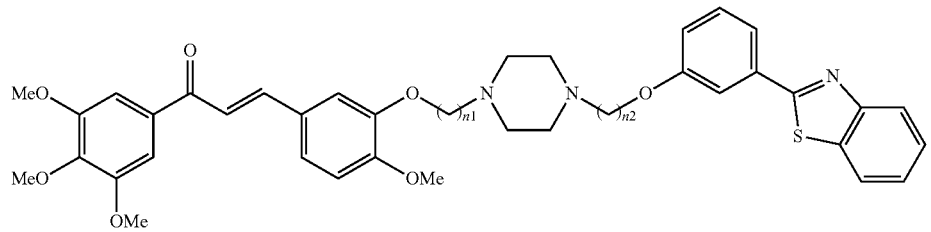
16t
n1 & n2 = 6
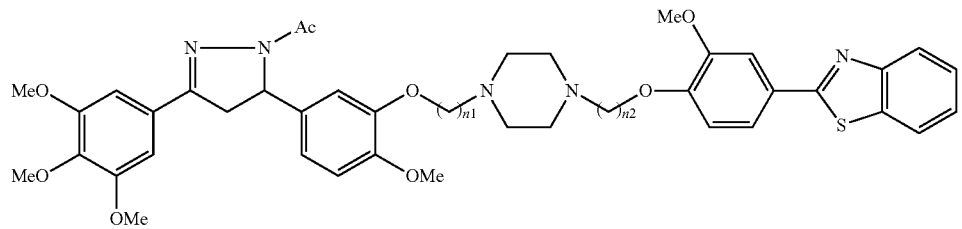
17a
n1 & n2 = 2
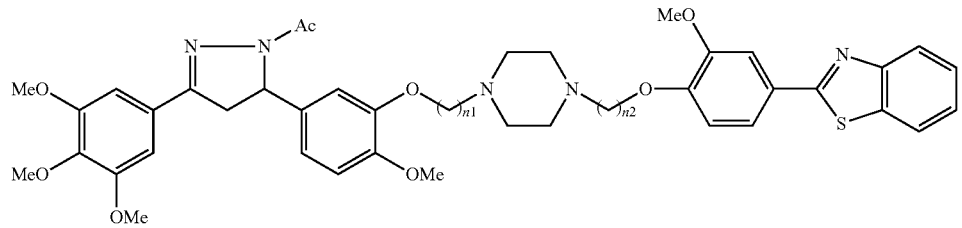
17b
n1 & n2 = 3
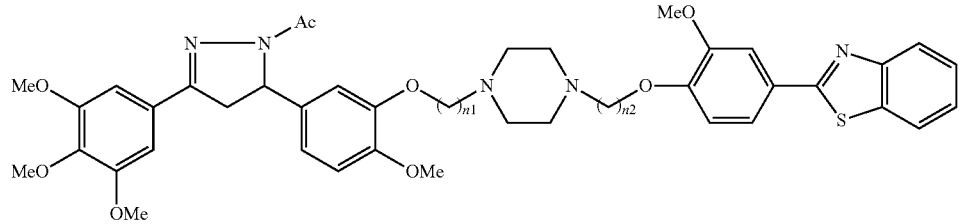
17c
n1 & n2 = 4
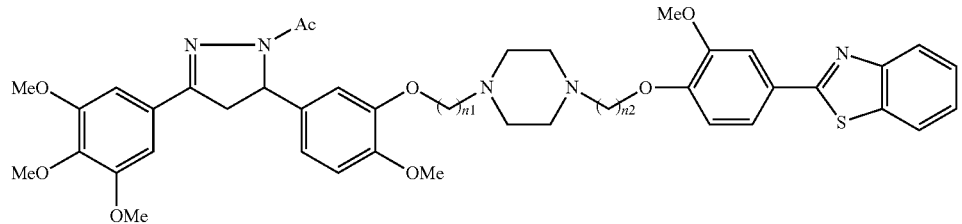
17d
n1 & n2 = 5

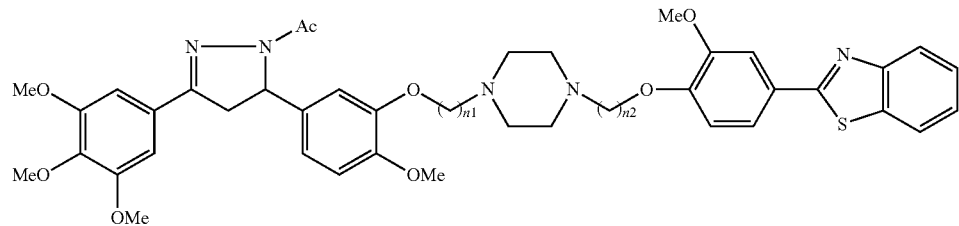
17e
n1 & n2 = 6
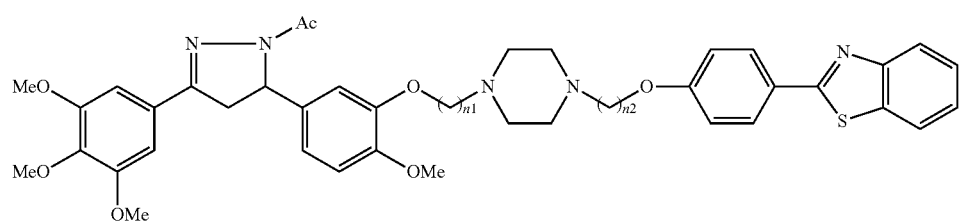
17f
n1 & n2 = 2
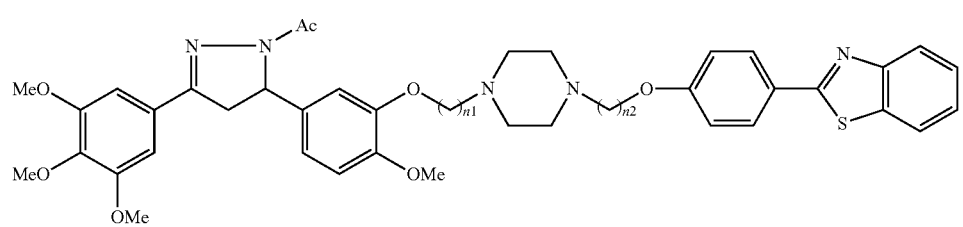
17g
n1 & n2 = 3
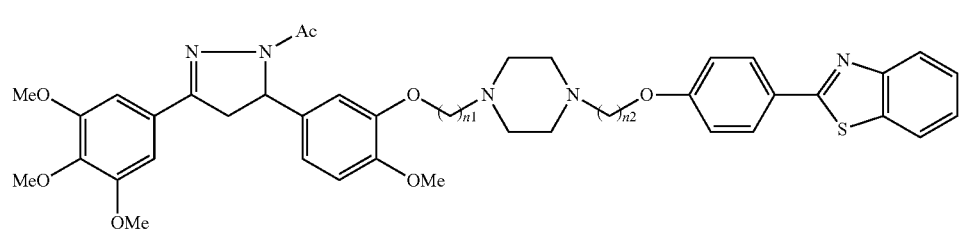
17h
n1 & n2 = 4
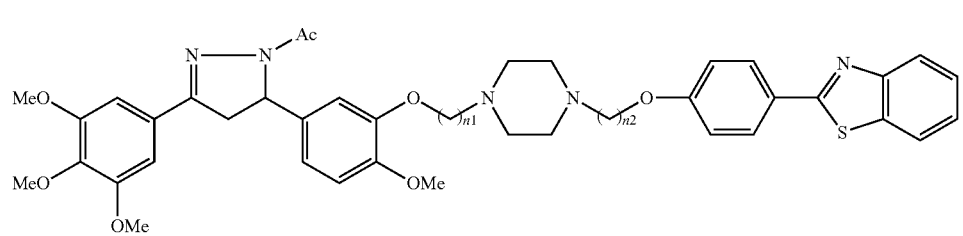
17i
n1 & n2 = 5
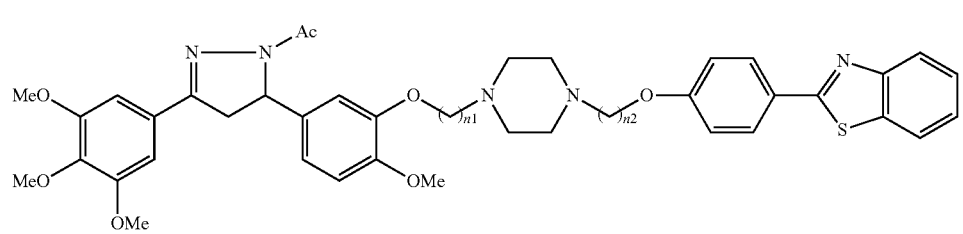
17j
n1 & n2 = 6

-continued
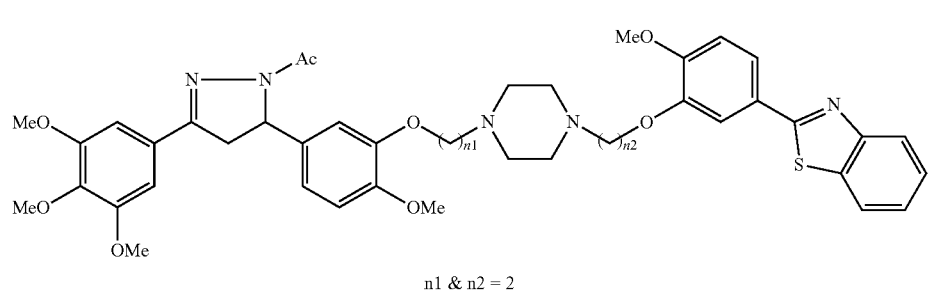
17k
n1 & n2 = 2
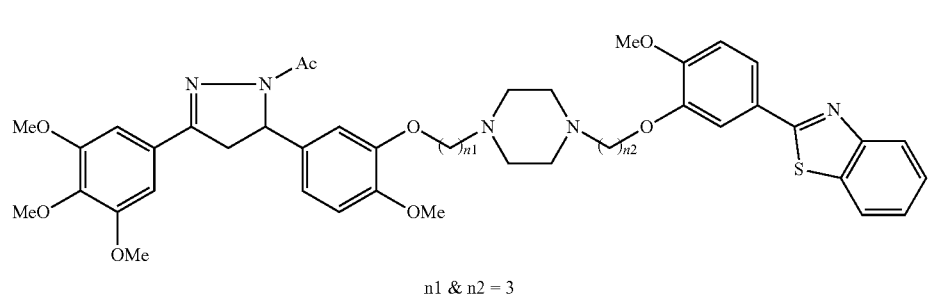
17l
n1 & n2 = 3
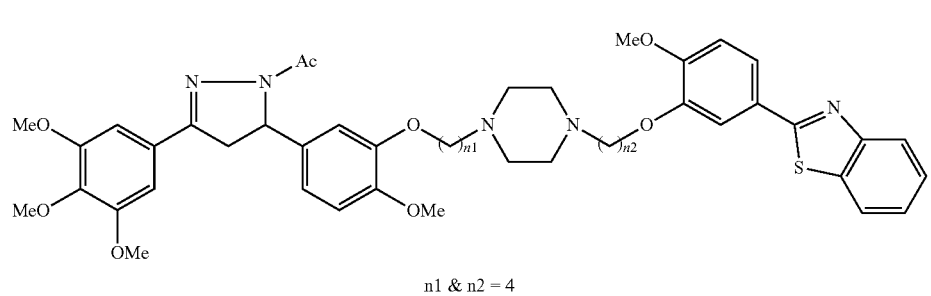
17m
n1 & n2 = 4
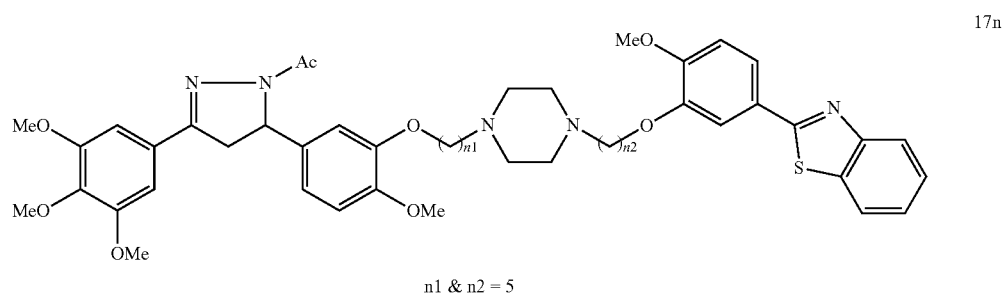
17n
n1 & n2 = 5
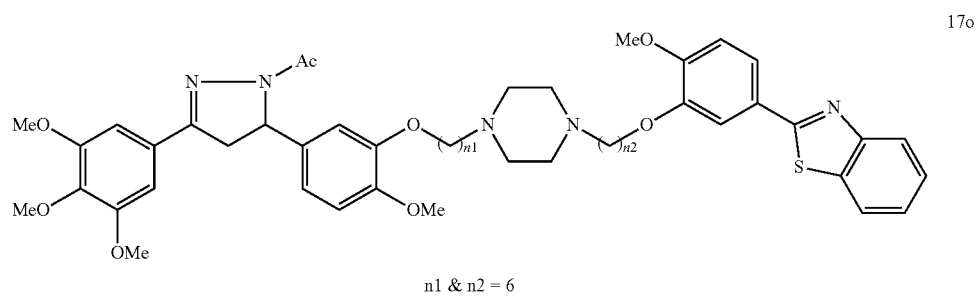
17o
n1 & n2 = 6

-continued
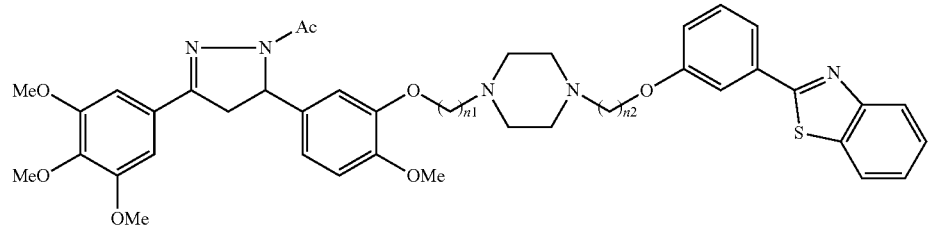
17p
n1 & n2 = 2
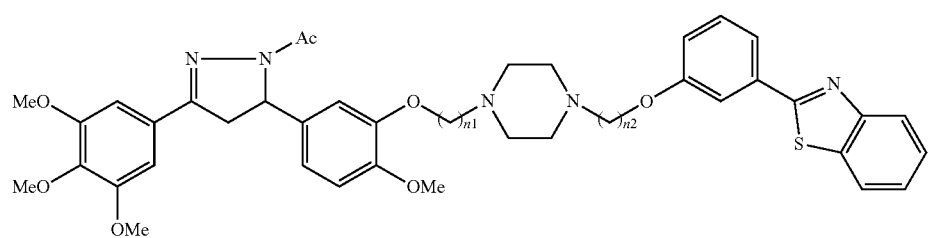
17q
n1 & n2 = 3
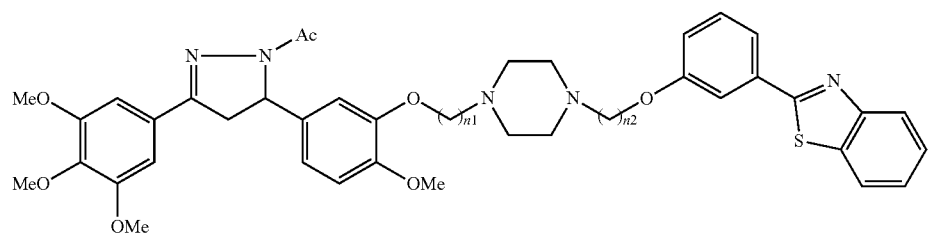
17r
n1 & n2 = 4
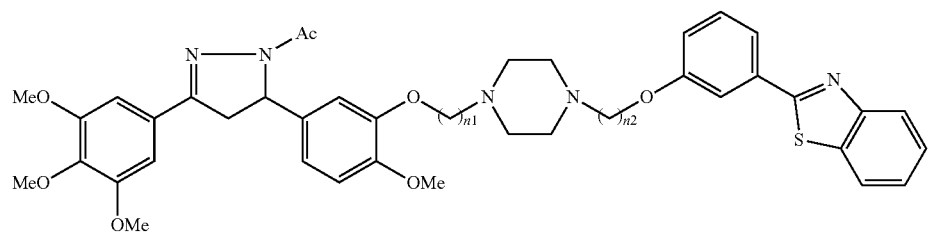
17s
n1 & n2 = 5
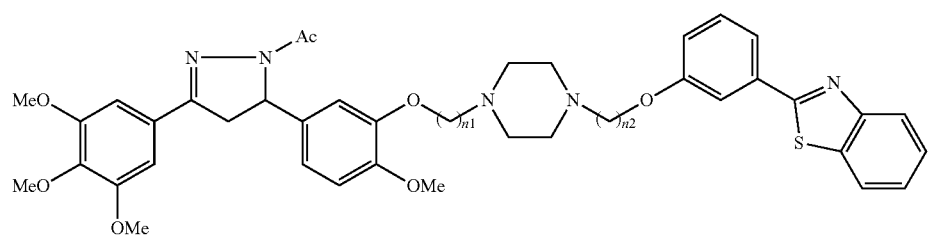
17t
n1 & n2 = 6
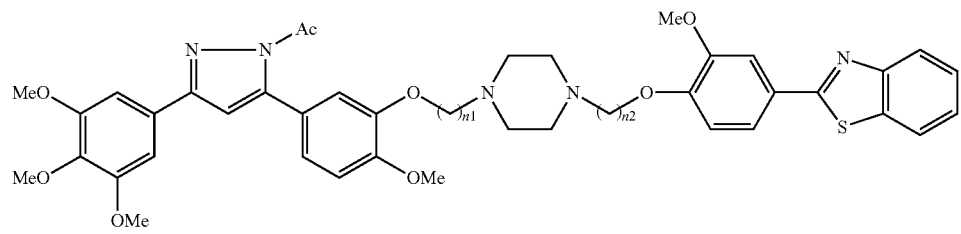
18a
n1 & n2 = 2

-continued
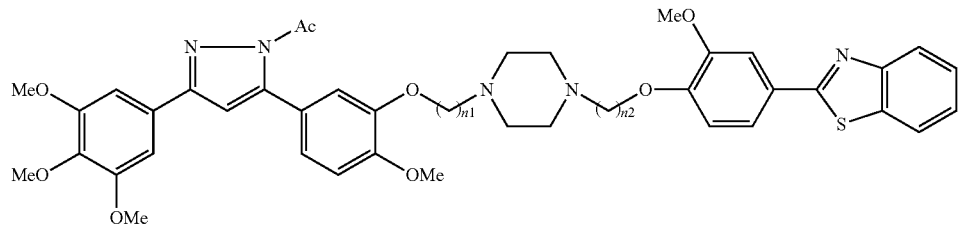
18b
n1 & n2 = 3
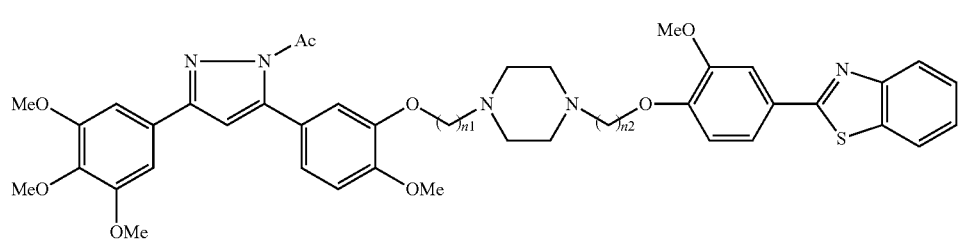
18c
n1 & n2 = 4
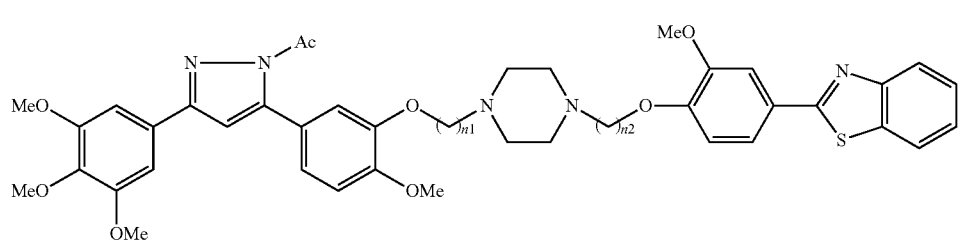
18d
n1 & n2 = 5
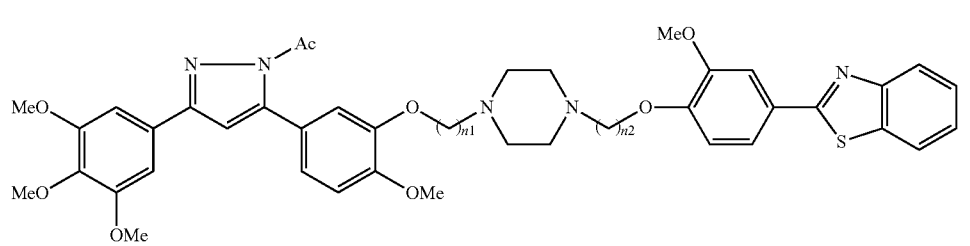
18e
n1 & n2 = 6
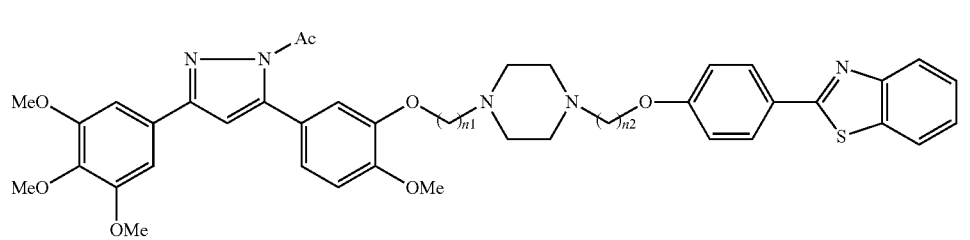
18f
n1 & n2 = 2
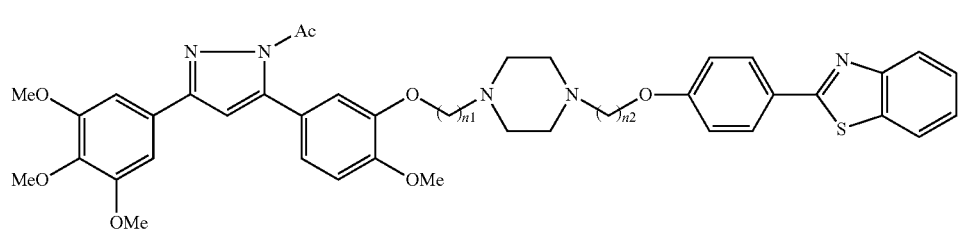
18g
n1 & n2 = 3

-continued
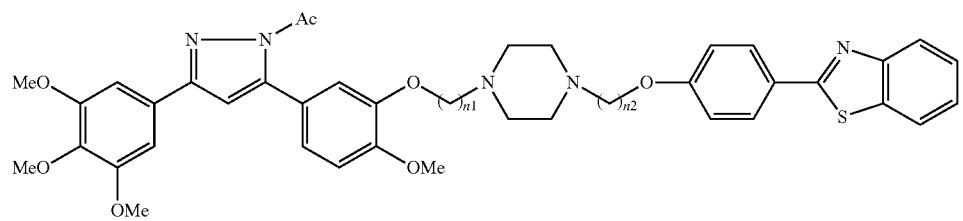
18h
n1 & n2 = 4
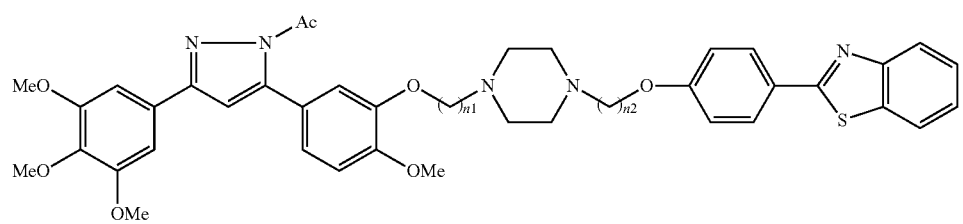
18i
n1 & n2 = 5
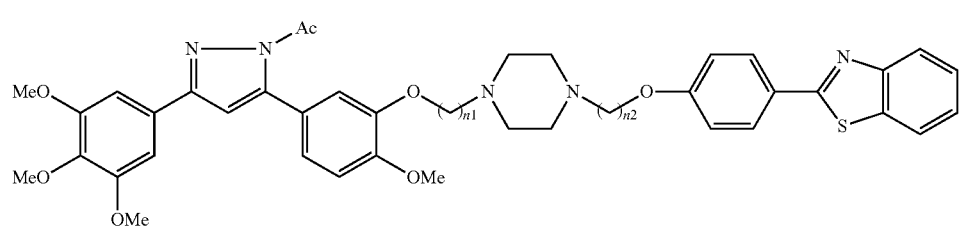
18j
n1 & n2 = 6
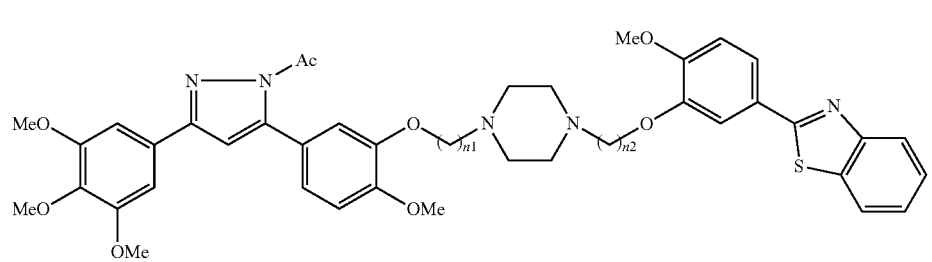
18k
n1 & n2 = 2
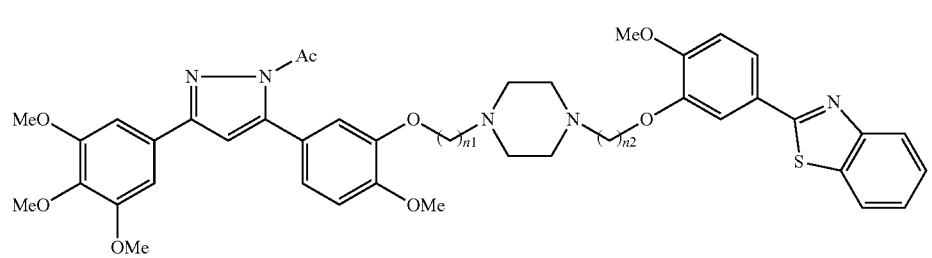
18l
n1 & n2 = 3
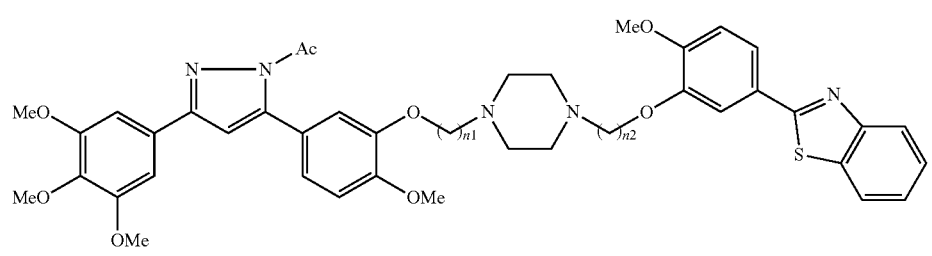
18m
n1 & n2 = 4

-continued
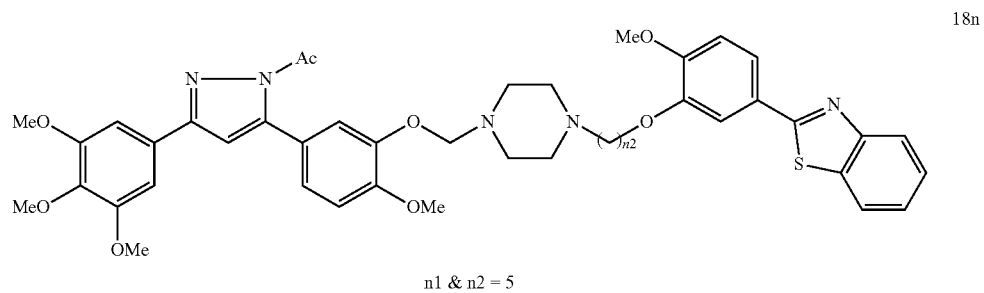
18n
n1 & n2 = 5
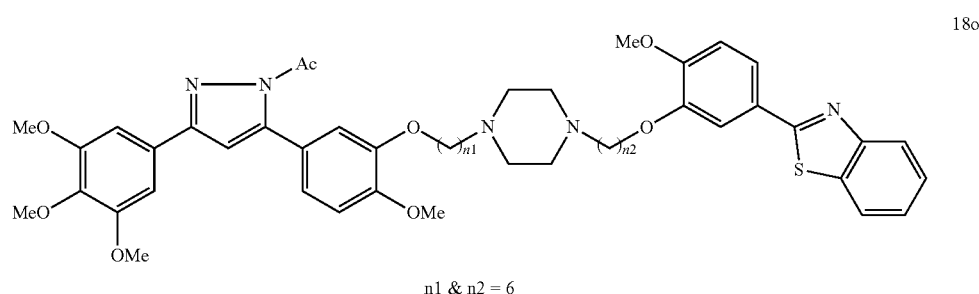
18o
n1 & n2 = 6
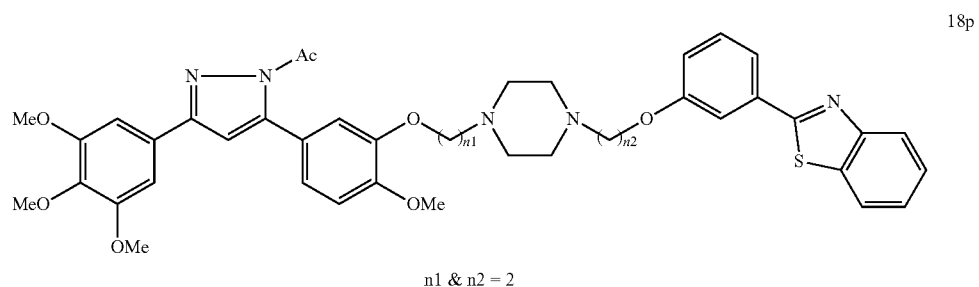
18p
n1 & n2 = 2
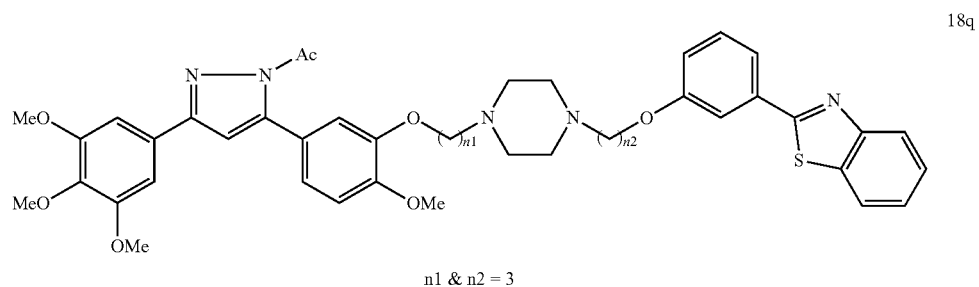
18q
n1 & n2 = 3
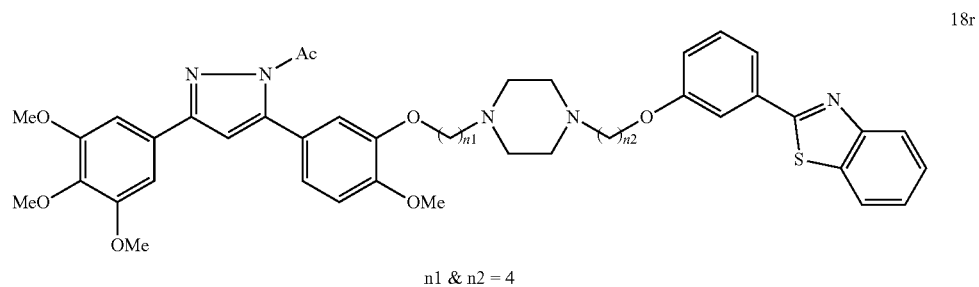
18r
n1 & n2 = 4

-continued
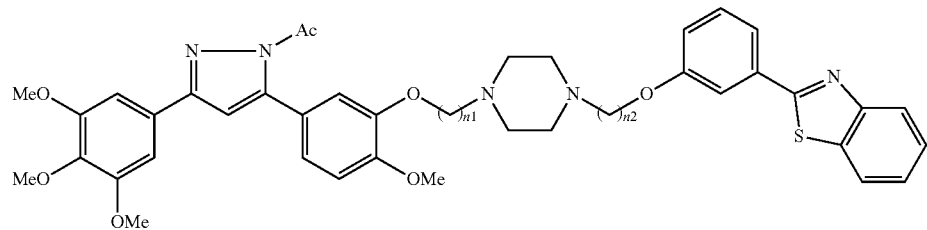
18s
n1 & n2 = 5
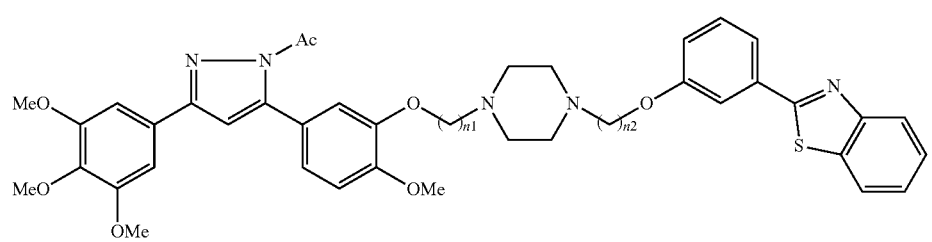
18t
n1 & n2 = 6
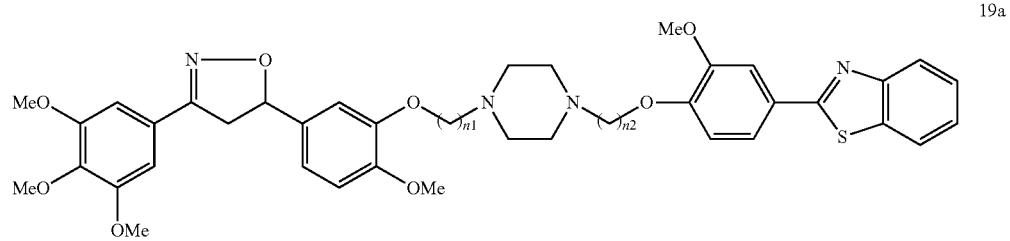
19a
n1 & n2 = 2
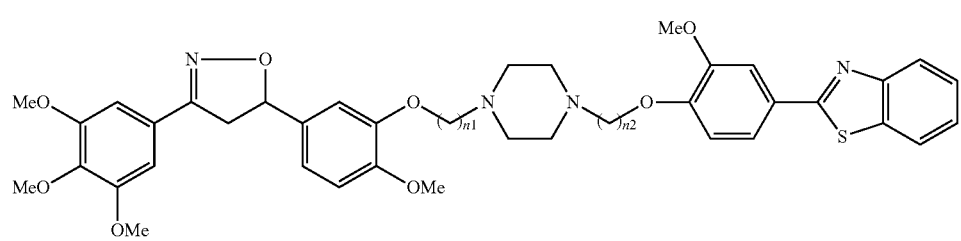
19b
n1 & n2 = 3
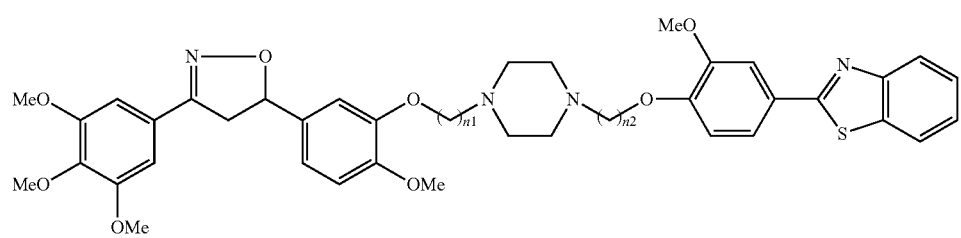
19c
n1 & n2 = 4
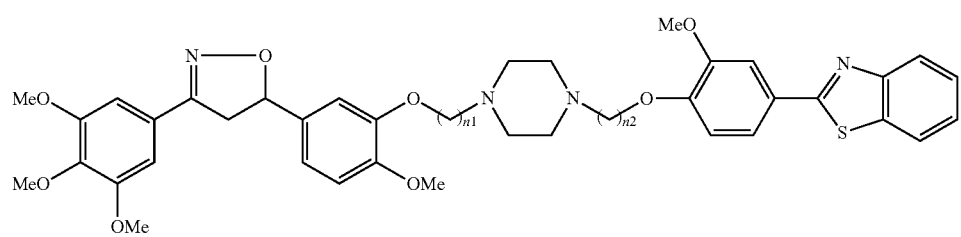
19d
n1 & n2 = 5

-continued
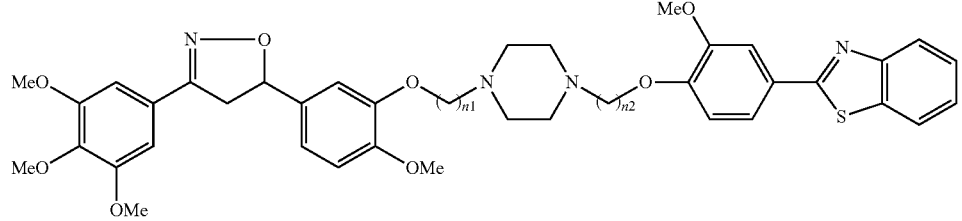
19e
n1 & n2 = 6
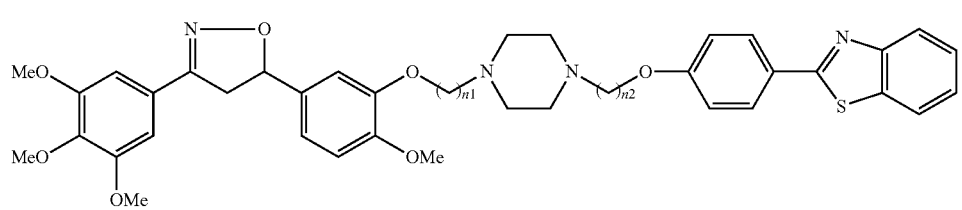
19f
n1 & n2 = 2
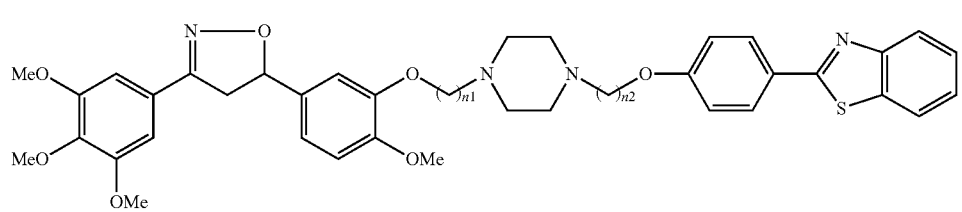
19g
n1 & n2 = 3
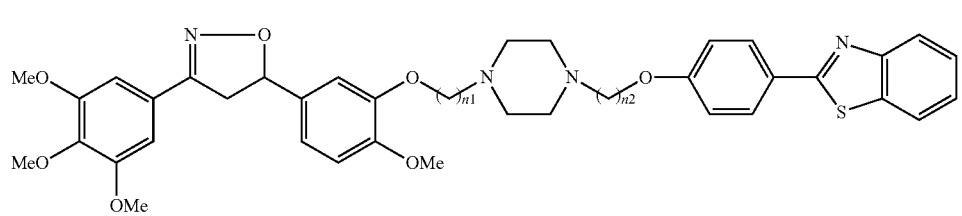
19h
n1 & n2 = 4
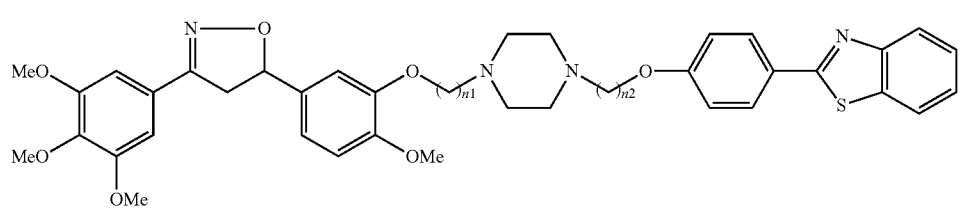
19i
n1 & n2 = 5
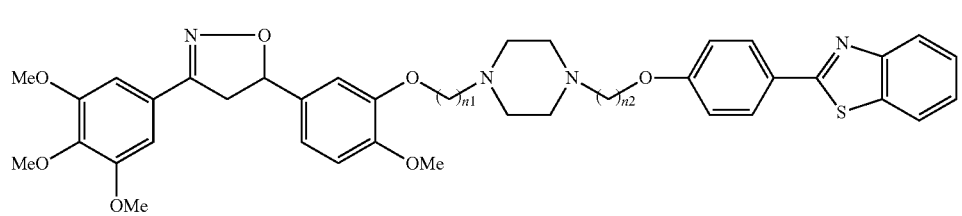
19j
n1 & n2 = 6

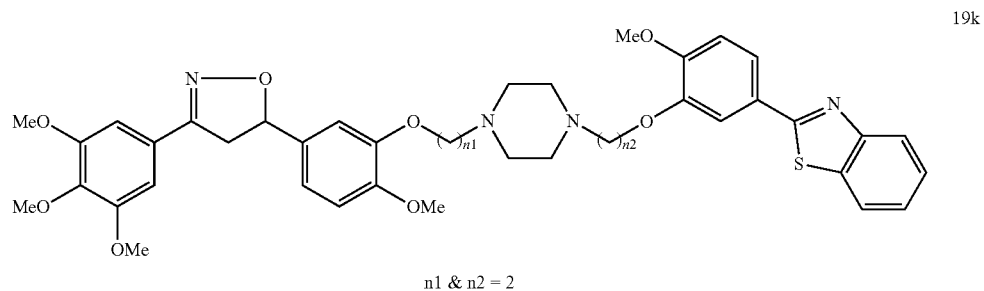
19k
n1 & n2 = 2
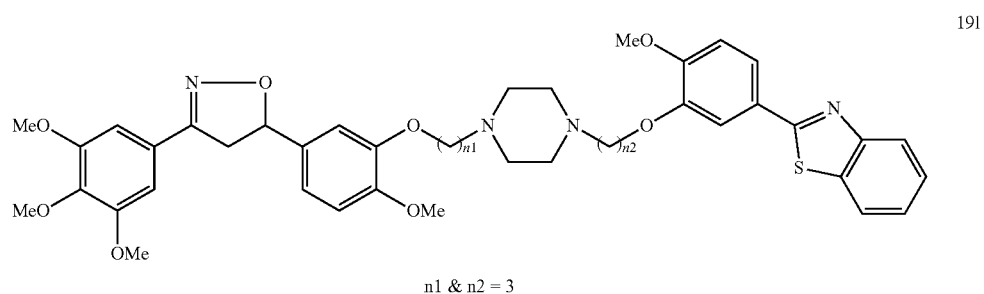
19l
n1 & n2 = 3
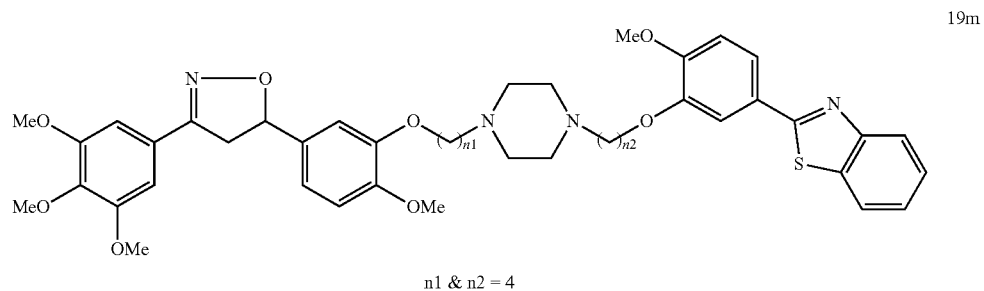
19m
n1 & n2 = 4
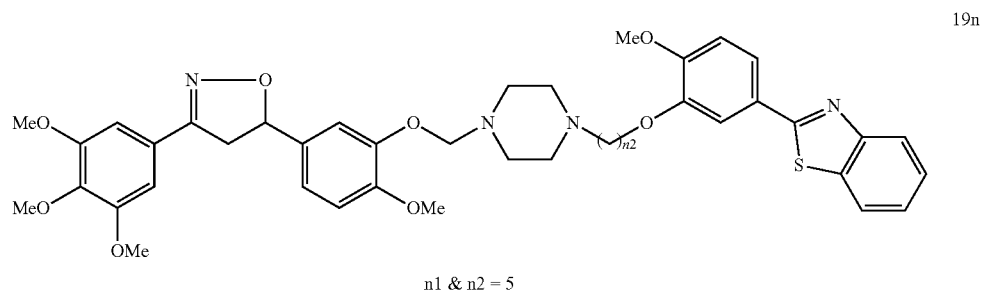
19n
n1 & n2 = 5
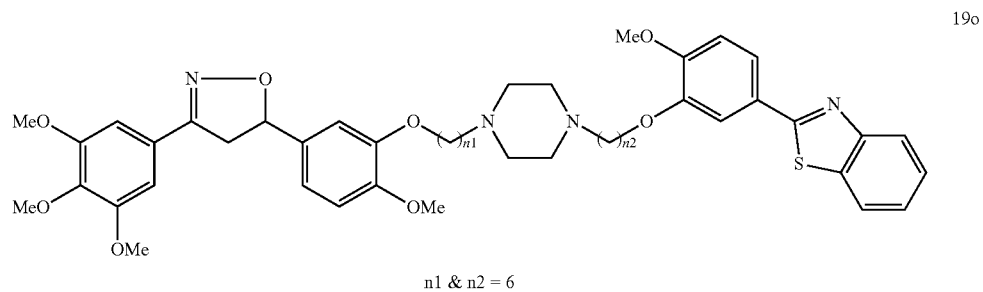
19o
n1 & n2 = 6

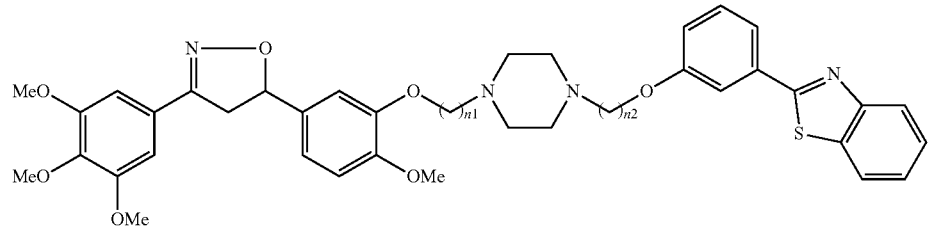
19p
n1 & n2 = 2
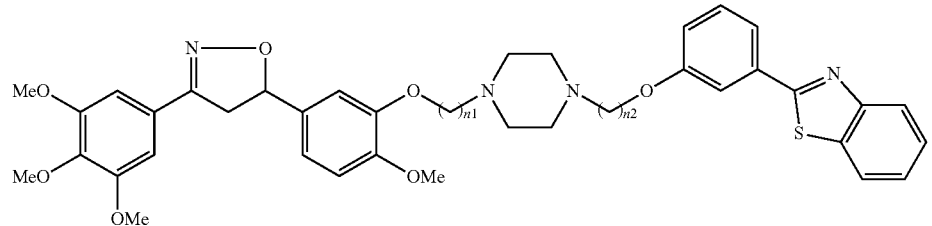
19q
n1 & n2 = 3
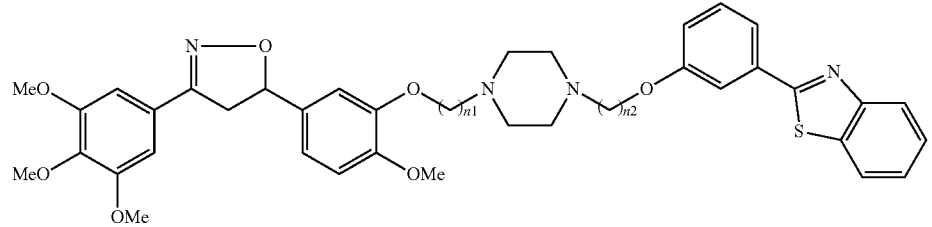
19r
n1 & n2 = 4
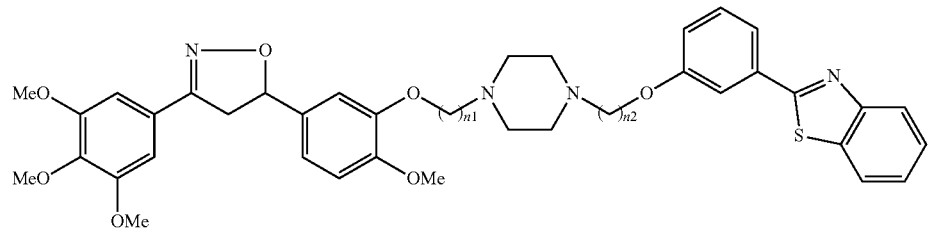
19s
n1 & n2 = 5
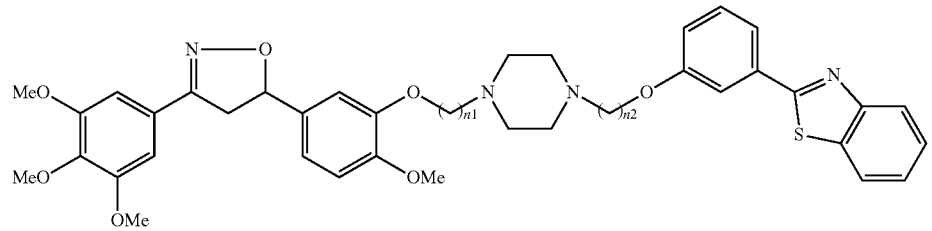
19t
n1 & n2 = 6
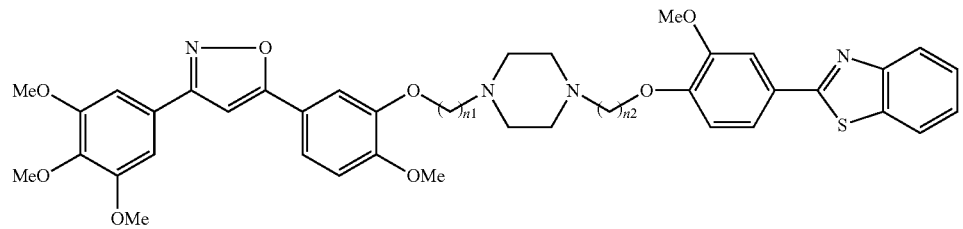
20a
n1 & n2 = 2

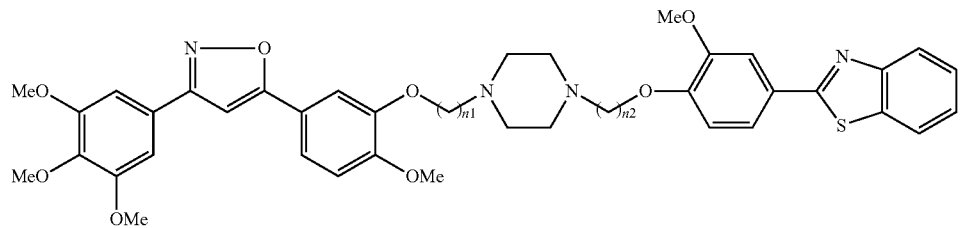
20b
n1 & n2 = 3
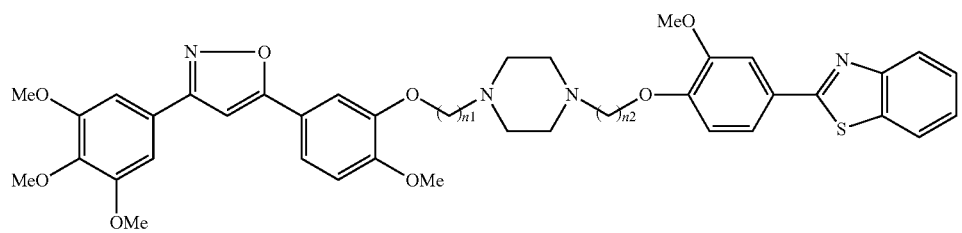
20c
n1 & n2 = 4
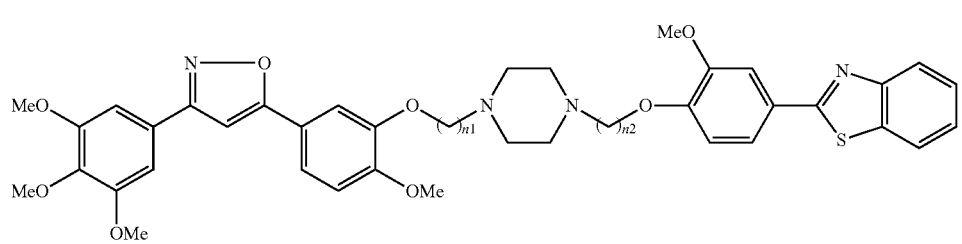
20d
n1 & n2 = 5
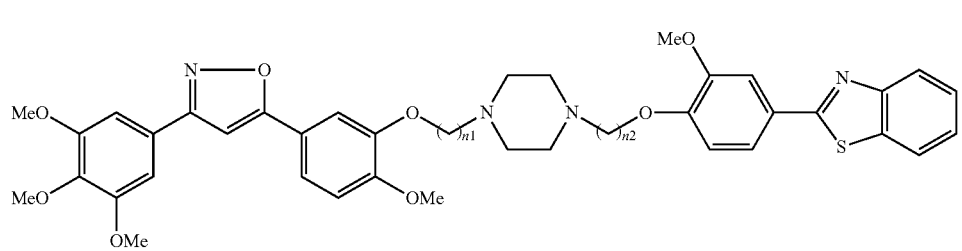
20e
n1 & n2 = 6
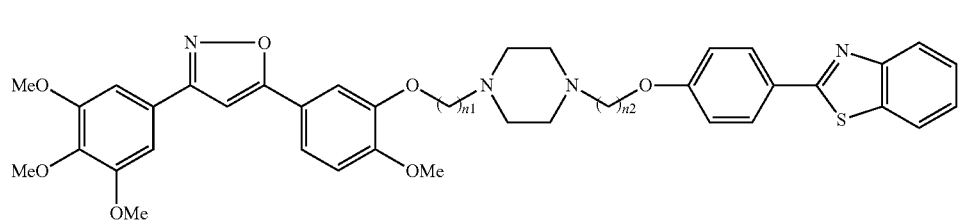
20f
n1 & n2 = 2
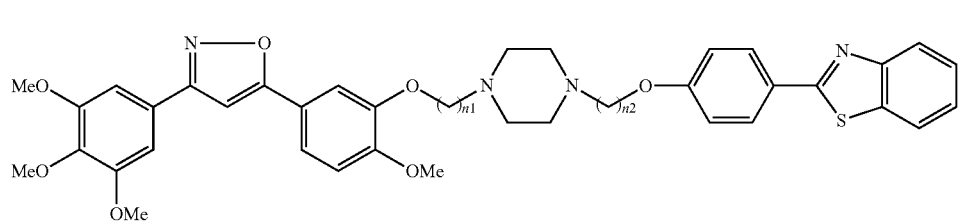
20g
n1 & n2 = 3

-continued
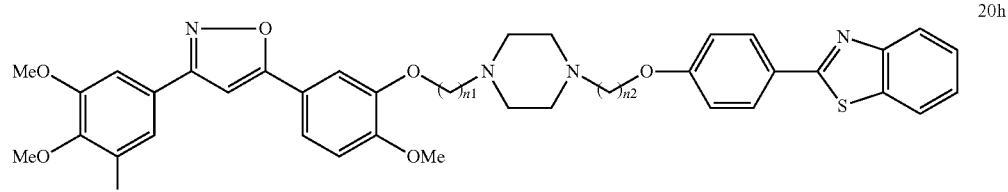
20h
n1 & n2 = 4
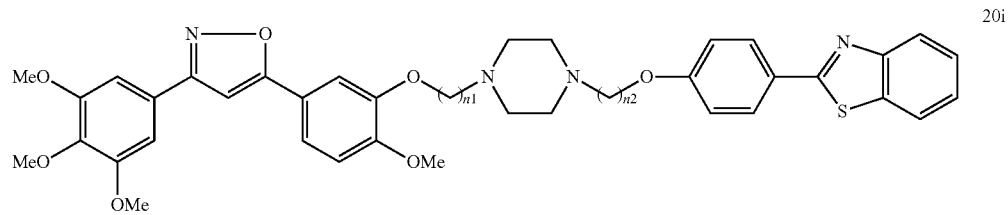
20i
n1 & n2 = 5
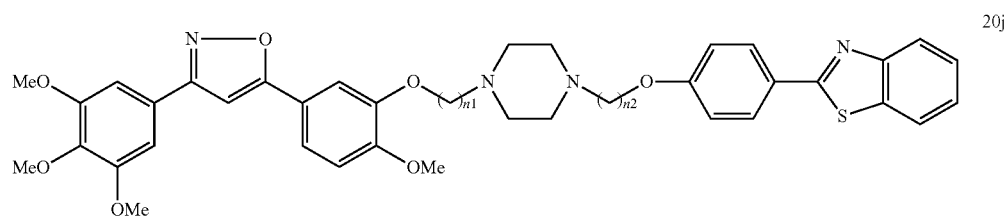
20j
n1 & n2 = 6
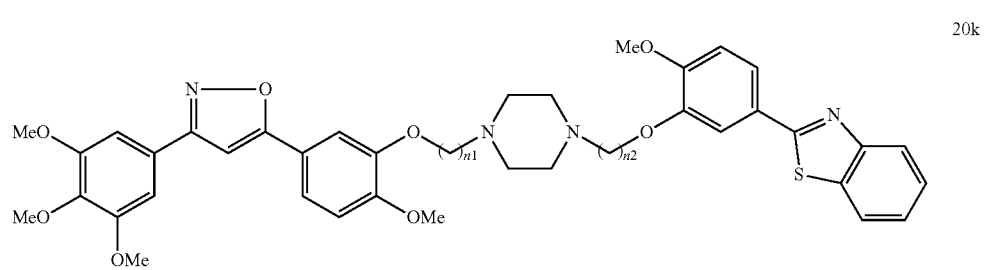
20k
n1 & n2 = 2
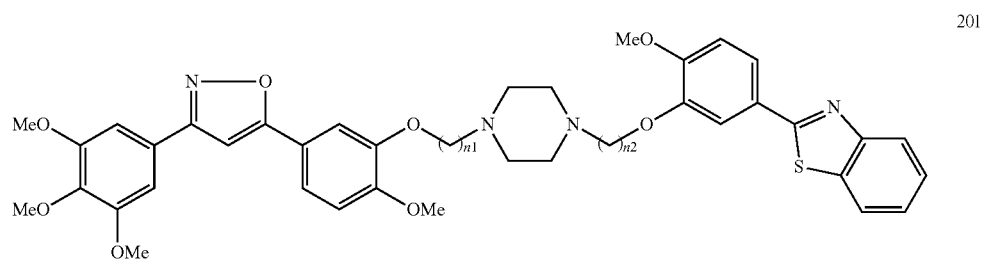
20l
n1 & n2 = 3
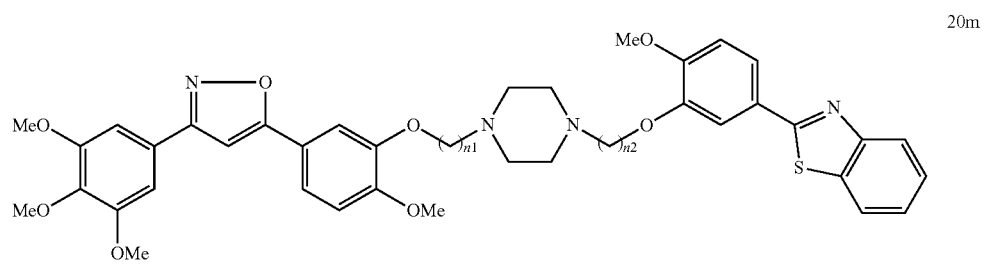
20m
n1 & n2 = 4

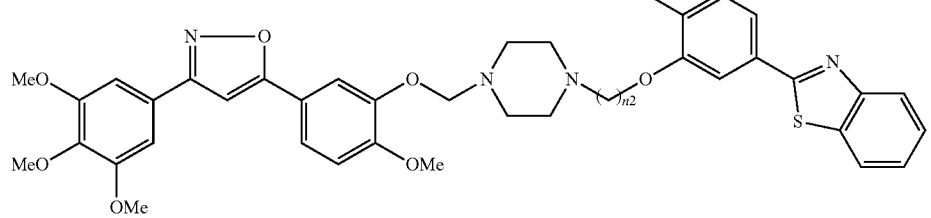
20n
n1 & n2 = 5
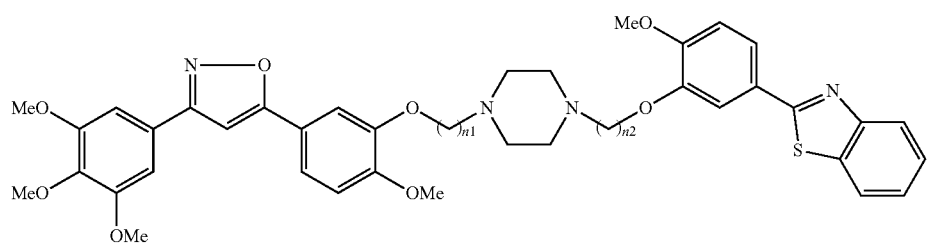
20o
n1 & n2 = 6
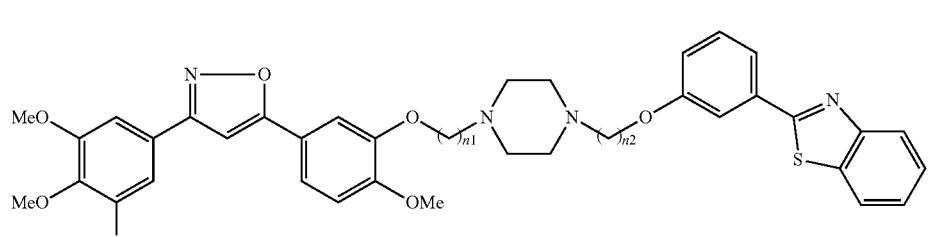
20p
n1 & n2 = 2
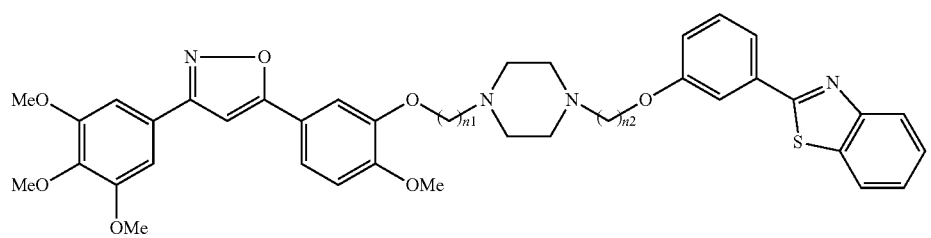
20q
n1 & n2 = 3
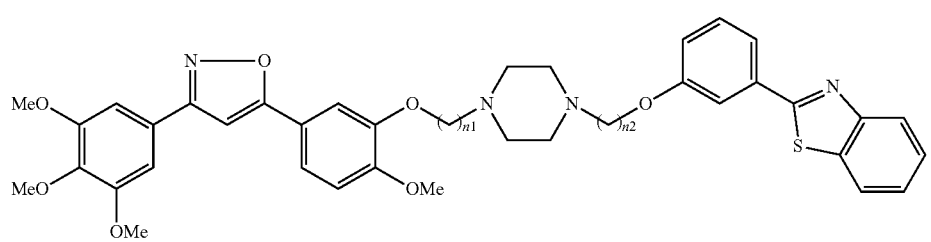
20r
n1 & n2 = 4

-continued

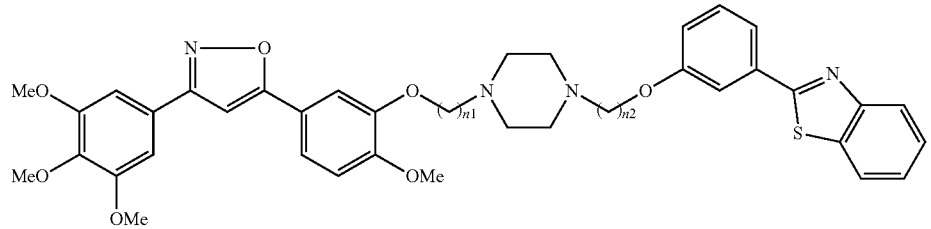

n1 & n2 = 5

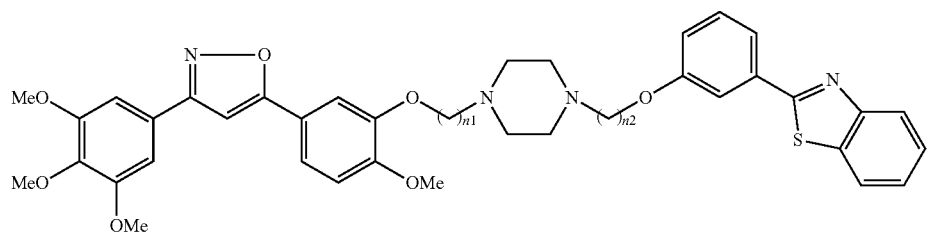

n1 & n2 = 6

In another embodiment of the present invention Benzothiazole hybrids of general formulae A is represented by the group of the following compounds 2-[3-methoxy-4-(2-{2-methoxy-5-[(Z)-2-(3,4,5-trimethoxyphenyl)-1-ethenyl]phenoxy}ethoxy)phenyl]-1,3-benzothiazole (9a)
2-[3-methoxy-4-(3-{2-methoxy-5-[(Z)-2-(3,4,5-trimethoxyphenyl)-1-ethenyl]phenoxy}propoxy)phenyl]-1,3-benzothiazole (9b)
2-[3-methoxy-4-(4-{2-methoxy-5-[(Z)-2-(3,4,5-trimethoxyphenyl)-1-ethenyl]phenoxy}butoxy)phenyl]-1,3-benzothiazole (9c)
2-[3-methoxy-4-(5-{2-methoxy-5-[(Z)-2-(3,4,5-trimethoxyphenyl)-1-ethenyl]phenoxy}pentoxy)phenyl]-1,3-benzothiazole (9d)
2-[3-methoxy-4-(6-{2-methoxy-5-[(Z)-2-(3,4,5-trimethoxyphenyl)-1-ethenyl]phenoxy}hexoxy)phenyl]-1,3-benzothiazole (9e)
2-[4-(2-{2-methoxy-5-[(Z)-2-(3,4,5-trimethoxyphenyl)-1-ethenyl]phenoxy}ethoxy)phenyl]-1,3-benzothiazole(9f)
2-[4-(3-{2-methoxy-5-[(Z)-2-(3,4,5-trimethoxyphenyl)-1-ethenyl]phenoxy}propoxy)phenyl]-1,3-benzothiazole (9g)
2-[4-(4-{2-methoxy-5-[(Z)-2-(3,4,5-trimethoxyphenyl)-1-ethenyl]phenoxy}butoxy)phenyl]-1,3-benzothiazole(9h)
2-[4-(5-{2-methoxy-5-[(Z)-2-(3,4,5-trimethoxyphenyl)-1-ethenyl]phenoxy}pentoxy)phenyl]-1,3-benzothiazole(9i)
2-[4-(6-{2-methoxy-5-[(Z)-2-(3,4,5-trimethoxyphenyl)-1-ethenyl]phenoxy}hexoxy)phenyl]-1,3-benzothiazole(9j)
2-[4-methoxy-3-(2-{2-methoxy-5-[(Z)-2-(3,4,5-trimethoxyphenyl)-1-ethenyl]phenoxy}ethoxy)phenyl]-1,3-benzothiazole(9k)
2-[4-methoxy-3-(3-{2-methoxy-5-[(Z)-2-(3,4,5-trimethoxyphenyl)-1-ethenyl]phenoxy}propoxy)phenyl]-1,3-benzothiazole(9l)
2-[4-methoxy-3-(4-{2-methoxy-5-[(Z)-2-(3,4,5-trimethoxyphenyl)-1-ethenyl]phenoxy}butoxy)phenyl]-1,3-benzothiazole(9m)
2-[4-methoxy-3-(5-{2-methoxy-5-[(Z)-2-(3,4,5-trimethoxyphenyl)-1-ethenyl]phenoxy}pentoxy)phenyl]-1,3-benzothiazole(9n)
2-[4-methoxy-3-(6-{2-methoxy-5-[(Z)-2-(3,4,5-trimethoxyphenyl)-1-ethenyl]phenoxy}hexoxy)phenyl]-1,3-benzothiazole(9o)
2-[3-(2-{2-methoxy-5-[(Z)-2-(3,4,5-trimethoxyphenyl)-1-ethenyl]phenoxy}ethoxy)phenyl]-1,3-benzothiazole(9p)
2-[3-(3-{2-methoxy-5-[(Z)-2-(3,4,5-trimethoxyphenyl)-1-ethenyl]phenoxy}propoxy)phenyl]-1,3-benzothiazole (9q)
2-[3-(4-{2-methoxy-5-[(Z)-2-(3,4,5-trimethoxyphenyl)-1-ethenyl]phenoxy}butoxy)phenyl]-1,3-benzothiazole(9r)
2-[3-(5-{2-methoxy-5-[(Z)-2-(3,4,5-trimethoxyphenyl)-1-ethenyl]phenoxy}pentoxy)phenyl]-1,3-benzothiazole(9s)
2-[3-(6-{2-methoxy-5-[(Z)-2-(3,4,5-trimethoxyphenyl)-1-ethenyl]phenoxy}hexoxy)phenyl]-1,3-benzothiazole(9t)
(E)-3-(3-{2-[4-(1,3-benzothiazol-2-yl)-2-methoxyphenoxy]ethoxy}-4-methoxy phenyl)-1-(3,4,5-trimethoxyphenyl)-2-propen-1-one(10a)
(E)-3-(3-{3-[4-(1,3-benzothiazol-2-yl)-2-methoxyphenoxy]propoxy}-4-methoxy phenyl)-1-(3,4,5-trimethoxyphenyl)-2-propen-1-one(10b)
(E)-3-(3-{4-[4-(1,3-benzothiazol-2-yl)-2-methoxyphenoxy]butoxy}-4-methoxy phenyl)-1-(3,4,5-trimethoxyphenyl)-2-propen-1-one(10c)
(E)-3-(3-{5-[4-(1,3-benzothiazol-2-yl)-2-methoxyphenoxy]pentoxy}-4-methoxy phenyl)-1-(3,4,5-trimethoxyphenyl)-2-propen-1-one(10d)
(E)-3-(3-{6-[4-(1,3-benzothiazol-2-yl)-2-methoxyphenoxy]hexoxy}-4-methoxy phenyl)-1-(3,4,5-trimethoxyphenyl)-2-propen-1-one(10e)
(E)-3-(3-{2-[4-(1,3-benzothiazol-2-yl)phenoxy]ethoxy}-4-methoxyphenyl)-1-(3,4,5-trimethoxyphenyl)-2-propen-1-one(10f)
(E)-3-(3-{3-[4-(1,3-benzothiazol-2-yl)phenoxy]propoxy}-4-methoxyphenyl)-1-(3,4,5-trimethoxyphenyl)-2-propen-1-one(10g)
(E)-3-(3-{4-[4-(1,3-benzothiazol-2-yl)phenoxy]butoxy}-4-methoxyphenyl)-1-(3,4,5-trimethoxyphenyl)-2-propen-1-one(10h)
(E)-3-(3-{5-[4-(1,3-benzothiazol-2-yl)phenoxy]pentoxy}-4-methoxyphenyl)-1-(3,4,5-trimethoxyphenyl)-2-propen-1-one(10i)

(E)-3-(3-{6-[4-(1,3-benzothiazol-2-yl)phenoxy]hexoxy}-4-methoxyphenyl)-1-(3,4,5-trimethoxyphenyl)-2-propen-1-one(10j)

(E)-3-(3-{2-[5-(1,3-benzothiazol-2-yl)-2-methoxyphenoxy]ethoxy}-4-methoxy phenyl)-1-(3,4,5-trimethoxyphenyl)-2-propen-1-one(10k)

(E)-3-(3-{3-[5-(1,3-benzothiazol-2-yl)-2-methoxyphenoxy]propoxy}-4-methoxy phenyl)-1-(3,4,5-trimethoxyphenyl)-2-propen-1-one(10l)

(E)-3-(3-{4-[5-(1,3-benzothiazol-2-yl)-2-methoxyphenoxy]butoxy}-4-methoxy phenyl)-1-(3,4,5-trimethoxyphenyl)-2-propen-1-one(10m)

(E)-3-(3-{5-[5-(1,3-benzothiazol-2-yl)-2-methoxyphenoxy]pentoxy}-4-methoxy phenyl)-1-(3,4,5-trimethoxyphenyl)-2-propen-1-one(10n)

(E)-3-(3-{6-[5-(1,3-benzothiazol-2-yl)-2-methoxyphenoxy]hexoxy}-4-methoxy phenyl)-1-(3,4,5-trimethoxyphenyl)-2-propen-1-one(10o)

(E)-3-(3-{2-[3-(1,3-benzothiazol-2-yl)phenoxy]ethoxy}-4-methoxyphenyl)-1-(3,4,5-trimethoxyphenyl)-2-propen-1-one(10p)

(E)-3-(3-{3-[3-(1,3-benzothiazol-2-yl)phenoxy]propoxy}-4-methoxyphenyl)-1-(3,4,5-trimethoxyphenyl)-2-propen-1-one(10q)

(E)-3-(3-{4-[3-(1,3-benzothiazol-2-yl)phenoxy]butoxy}-4-methoxyphenyl)-1-(3,4,5-trimethoxyphenyl)-2-propen-1-one(10r)

(E)-3-(3-{5-[3-(1,3-benzothiazol-2-yl)phenoxy]pentoxy}-4-methoxyphenyl)-1-(3,4,5-trimethoxyphenyl)-2-propen-1-one(10s)

(E)-3-(3-{6-[3-(1,3-benzothiazol-2-yl)phenoxy]hexoxy}-4-methoxyphenyl)-1-(3,4,5-trimethoxyphenyl)-2-propen-1-one(10t)

1-[5-[3-({2-[4-(1,3-benzothiazol-2-yl)-2-methoxyphenoxy]ethyl}oxy)-4-methoxy phenyl]-3-(3,4,5-trimethoxyphenyl)-4,5-dihydro-1H-1-pyrazolyl]-1-ethanone(11a)

1-[5-[3-({3-[4-(1,3-benzothiazol-2-yl)-2-methoxyphenoxy]propyl}oxy)-4-methoxyphenyl]-3-(3,4,5-trimethoxyphenyl)-4,5-dihydro-1H-1-pyrazolyl]-1-ethanone(11b)

1-[5-[3-({4-[4-(1,3-benzothiazol-2-yl)-2-methoxyphenoxy]butyl}oxy)-4-methoxyphenyl]-3-(3,4,5-trimethoxyphenyl)-4,5-dihydro-1H-1-pyrazolyl]-1-ethanone(11c)

1-[5-[3-({5-[4-(1,3-benzothiazol-2-yl)-2-methoxyphenoxy]pentyl}oxy)-4-methoxyphenyl]-3-(3,4,5-trimethoxyphenyl)-4,5-dihydro-1H-1-pyrazolyl]-1-ethanone(11d)

1-[5-[3-({6-[4-(1,3-benzothiazol-2-yl)-2-methoxyphenoxy]hexyl}oxy)-4-methoxyphenyl]-3-(3,4,5-trimethoxyphenyl)-4,5-dihydro-1H-1-pyrazolyl]-1-ethanone(11e)

1-[5-[3-({2-[4-(1,3-benzothiazol-2-yl)phenoxy]ethyl}oxy)-4-methoxyphenyl]-3-(3,4,5-trimethoxyphenyl)-4,5-dihydro-1H-1-pyrazolyl]-1-ethanone(11f)

1-[5-[3-({3-[4-(1,3-benzothiazol-2-yl)phenoxy]propyl}oxy)-4-methoxyphenyl]-3-(3,4,5-trimethoxyphenyl)-4,5-dihydro-1H-1-pyrazolyl]-1-ethanone(11g)

1-[5-[3-({4-[4-(1,3-benzothiazol-2-yl)phenoxy]butyl}oxy)-4-methoxyphenyl]-3-(3,4,5-trimethoxyphenyl)-4,5-dihydro-1H-1-pyrazolyl]-1-ethanone(11h)

1-[5-[3-({5-[4-(1,3-benzothiazol-2-yl)phenoxy]pentyl}oxy)-4-methoxyphenyl]-3-(3,4,5-trimethoxyphenyl)-4,5-dihydro-1H-1-pyrazolyl]-1-ethanone(11i)

1-[5-[3-({6-[4-(1,3-benzothiazol-2-yl)phenoxy]hexyl}oxy)-4-methoxyphenyl]-3-(3,4,5-trimethoxyphenyl)-4,5-dihydro-1H-1-pyrazolyl]-1-ethanone(11j)

1-[5-[3-({2-[5-(1,3-benzothiazol-2-yl)-2-methoxyphenoxy]ethyl}oxy)-4-methoxyphenyl]-3-(3,4,5-trimethoxyphenyl)-4,5-dihydro-1H-1-pyrazolyl]-1-ethanone(11k)

1-[5-[3-({3-[5-(1,3-benzothiazol-2-yl)-2-methoxyphenoxy]propyl}oxy)-4-methoxyphenyl]-3-(3,4,5-trimethoxyphenyl)-4,5-dihydro-1H-1-pyrazolyl]-1-ethanone(11l)

1-[5-[3-({4-[5-(1,3-benzothiazol-2-yl)-2-methoxyphenoxy]butyl}oxy)-4-methoxyphenyl]-3-(3,4,5-trimethoxyphenyl)-4,5-dihydro-1H-1-pyrazolyl]-1-ethanone(11m)

1-[5-[3-({5-[5-(1,3-benzothiazol-2-yl)-2-methoxyphenoxy]pentyl}oxy)-4-methoxyphenyl]-3-(3,4,5-trimethoxyphenyl)-4,5-dihydro-1H-1-pyrazolyl]-1-ethanone(11n)

1-[5-[3-({6-[5-(1,3-benzothiazol-2-yl)-2-methoxyphenoxy]hexyl}oxy)-4-methoxyphenyl]-3-(3,4,5-trimethoxyphenyl)-4,5-dihydro-1H-1-pyrazolyl]-1-ethanone(11o)

1-[5-(3-{2-[3-(1,3-benzothiazol-2-yl)phenoxy]ethoxy}-4-methoxyphenyl)-3-(3,4,5-trimethoxyphenyl)-4,5-dihydro-1H-1-pyrazolyl]-1-ethanone(11p)

1-[5-(3-{3-[3-(1,3-benzothiazol-2-yl)phenoxy]propoxy}-4-methoxyphenyl)-3-(3,4,5-trimethoxyphenyl)-4,5-dihydro-1H-1-pyrazolyl]-1-ethanone(11q)

1-[5-(3-{4-[3-(1,3-benzothiazol-2-yl)phenoxy]butoxy}-4-methoxyphenyl)-3-(3,4,5-trimethoxyphenyl)-4,5-dihydro-1H-1-pyrazolyl]-1-ethanone(11r)

1-[5-(3-{5-[3-(1,3-benzothiazol-2-yl)phenoxy]pentoxy}-4-methoxyphenyl)-3-(3,4,5-trimethoxyphenyl)-4,5-dihydro-1H-1-pyrazolyl]-1-ethanone(11s)

1-[5-(3-{6-[3-(1,3-benzothiazol-2-yl)phenoxy]hexoxy}-4-methoxyphenyl)-3-(3,4,5-trimethoxyphenyl)-4,5-dihydro-1H-1-pyrazolyl]-1-ethanone(11t)

1-[5-(3-{2-[4-(1,3-benzothiazol-2-yl)-2-methoxyphenoxy]ethoooxy}-4-methoxyphenyl)-3-(3,4,5-trimethoxyphenyl)-1H-1-pyrazolyl]-1-ethanone(12a)

1-[5-(3-{3-[4-(1,3-benzothiazol-2-yl)-2-methoxyphenoxy]propoxy}-4-methoxyphenyl)-3-(3,4,5-trimethoxyphenyl)-1H-1-pyrazolyl]-1-ethanone(12b)

1-[5-(3-{4-[4-(1,3-benzothiazol-2-yl)-2-methoxyphenoxy]butoxy}-4-methoxyphenyl)-3-(3,4,5-trimethoxyphenyl)-1H-1-pyrazolyl]-1-ethanone(12c)

1-[5-(3-{5-[4-(1,3-benzothiazol-2-yl)-2-methoxyphenoxy]pentoxy}-4-methoxyphenyl)-3-(3,4,5-trimethoxyphenyl)-1H-1-pyrazolyl]-1-ethanone(12d)

1-[5-(3-{6-[4-(1,3-benzothiazol-2-yl)-2-methoxyphenoxy]hexoxy}-4-methoxyphenyl)-3-(3,4,5-trimethoxyphenyl)-1H-1-pyrazolyl]-1-ethanone(12e)

1-[5-(3-{2-[4-(1,3-benzothiazol-2-yl)phenoxy]ethoxy}-4-methoxyphenyl)-3-(3,4,5-trimethoxyphenyl)-1H-1-pyrazolyl]-1-ethanone(12f)

1-[5-(3-{3-[4-(1,3-benzothiazol-2-yl)phenoxy]propoxy}-4-methoxyphenyl)-3-(3,4,5-trimethoxyphenyl)-1H-1-pyrazolyl]-1-ethanone(12g)

1-[5-(3-{4-[4-(1,3-benzothiazol-2-yl)phenoxy]butoxy}-4-methoxyphenyl)-3-(3,4,5-trimethoxyphenyl)-1H-1-pyrazolyl]-1-ethanone(12h)

1-[5-(3-{5-[4-(1,3-benzothiazol-2-yl)phenoxy]pentoxy}-4-methoxyphenyl)-3-(3,4,5-trimethoxyphenyl)-1H-1-pyrazolyl]-1-ethanone(12i)

1-[5-(3-{6-[4-(1,3-benzothiazol-2-yl)phenoxy]hexoxy}-4-methoxyphenyl)-3-(3,4,5-trimethoxyphenyl)-1H-1-pyrazolyl]-1-ethanone(12j)

1-[5-(3-{2-[5-(1,3-benzothiazol-2-yl)-2-methoxyphenoxy]ethoxy}-4-methoxyphenyl)-3-(3,4,5-trimethoxyphenyl)-1H-1-pyrazolyl]-1-ethanone(12k)

1-[5-(3-{3-[5-(1,3-benzothiazol-2-yl)-2-methoxyphenoxy]propoxy}-4-methoxyphenyl)-3-(3,4,5-trimethoxyphenyl)-1H-1-pyrazolyl]-1-ethanone(12l)

1-[5-(3-{4-[5-(1,3-benzothiazol-2-yl)-2-methoxyphenoxy]butoxy}-4-methoxyphenyl)-3-(3,4,5-trimethoxyphenyl)-1H-1-pyrazolyl]-1-ethanone(12m)

1-[5-(3-{5-[5-(1,3-benzothiazol-2-yl)-2-methoxyphenoxy]pentoxy}-4-methoxyphenyl)-3-(3,4,5-trimethoxyphenyl)-1H-1-pyrazolyl]-1-ethanone(12n)

1-[5-(3-{6-[5-(1,3-benzothiazol-2-yl)-2-methoxyphenoxy]hexoxy}-4-methoxyphenyl)-3-(3,4,5-trimethoxyphenyl)-1H-1-pyrazolyl]-1-ethanone(12o)

1-[5-(3-{2-[3-(1,3-benzothiazol-2-yl)phenoxy]ethoxy}-4-methoxyphenyl)-3-(3,4,5-trimethoxyphenyl)-4,5-dihydro-1H-1-pyrazolyl]-1-ethanone(12p)

1-[5-(3-{3-[3-(1,3-benzothiazol-2-yl)phenoxy]propoxy}-4-methoxyphenyl)-3-(3,4,5-trimethoxyphenyl)-4,5-dihydro-1H-1-pyrazolyl]-1-ethanone(12q)

1-[5-(3-{4-[3-(1,3-benzothiazol-2-yl)phenoxy]butoxy}-4-methoxyphenyl)-3-(3,4,5-trimethoxyphenyl)-4,5-dihydro-1H-1-pyrazolyl]-1-ethanone(12r)

1-[5-(3-{5-[3-(1,3-benzothiazol-2-yl)phenoxy]pentoxy}-4-methoxyphenyl)-3-(3,4,5-trimethoxyphenyl)-4,5-dihydro-1H-1-pyrazolyl]-1-ethanone(12s)

1-[5-(3-{6-[3-(1,3-benzothiazol-2-yl)phenoxy]hexoxy}-4-methoxyphenyl)-3-(3,4,5-trimethoxyphenyl)-4,5-dihydro-1H-1-pyrazolyl]-1-ethanone(12t)

5-(3-{2-[4-(1,3-benzothiazol-2-yl)-2-methoxyphenoxy]ethoxy}-4-methoxyphenyl)-3-(3,4,5-trimethoxyphenyl)-4,5-dihydroisoxazole(13a)

5-(3-{3-[4-(1,3-benzothiazol-2-yl)-2-methoxyphenoxy]propoxy}-4-methoxyphenyl)-3-(3,4,5-trimethoxyphenyl)-4,5-dihydroisoxazole(13b)

5-(3-{4-[4-(1,3-benzothiazol-2-yl)-2-methoxyphenoxy]butoxy}-4-methoxyphenyl)-3-(3,4,5-trimethoxyphenyl)-4,5-dihydroisoxazole(13c)

5-(3-{5-[4-(1,3-benzothiazol-2-yl)-2-methoxyphenoxy]pentoxy}-4-methoxyphenyl)-3-(3,4,5-trimethoxyphenyl)-4,5-dihydroisoxazole(13d)

5-(3-{6-[4-(1,3-benzothiazol-2-yl)-2-methoxyphenoxy]hexoxy}-4-methoxyphenyl)-3-(3,4,5-trimethoxyphenyl)-4,5-dihydroisoxazole(13e)

5-(3-{2-[4-(1,3-benzothiazol-2-yl)phenoxy]ethoxy}-4-methoxyphenyl)-3-(3,4,5-trimethoxyphenyl)-4,5-dihydroisoxazole(13f)

5-(3-{3-[4-(1,3-benzothiazol-2-yl)phenoxy]propoxy}-4-methoxyphenyl)-3-(3,4,5-trimethoxyphenyl)-4,5-dihydroisoxazole(13g)

5-(3-{4-[4-(1,3-benzothiazol-2-yl)phenoxy]butoxy}-4-methoxyphenyl)-3-(3,4,5-trimethoxyphenyl)-4,5-dihydroisoxazole(13h)

5-(3-{5-[4-(1,3-benzothiazol-2-yl)phenoxy]pentoxy}-4-methoxyphenyl)-3-(3,4,5-trimethoxyphenyl)-4,5-dihydroisoxazole(13i)

5-(3-{6-[4-(1,3-benzothiazol-2-yl)phenoxy]hexoxy}-4-methoxyphenyl)-3-(3,4,5-trimethoxyphenyl)-4,5-dihydroisoxazole(13j)

5-(3-{2-[5-(1,3-benzothiazol-2-yl)-2-methoxyphenoxy]ethoxy}-4-methoxyphenyl)-3-(3,4,5-trimethoxyphenyl)-4,5-dihydroisoxazole(13k 5-(3-{3-[5-(1,3-benzothiazol-2-yl)-2-methoxyphenoxy]propoxy}-4-methoxyphenyl)-3-(3,4,5-trimethoxyphenyl)-4,5-dihydroisoxazole(13l)

5-(3-{4-[5-(1,3-benzothiazol-2-yl)-2-methoxyphenoxy]butoxy}-4-methoxyphenyl)-3-(3,4,5-trimethoxyphenyl)-4,5-dihydroisoxazole(13m)

5-(3-{5-[5-(1,3-benzothiazol-2-yl)-2-methoxyphenoxy]pentoxy}-4-methoxyphenyl)-3-(3,4,5-trimethoxyphenyl)-4,5-dihydroisoxazole(13n)

5-(3-{6-[5-(1,3-benzothiazol-2-yl)-2-methoxyphenoxy]hexoxy}-4-methoxyphenyl)-3-(3,4,5-trimethoxyphenyl)-4,5-dihydroisoxazole(13o)

5-(3-{2-[3-(1,3-benzothiazol-2-yl)phenoxy]ethoxy}-4-methoxyphenyl)-3-(3,4,5-trimethoxyphenyl)-4,5-dihydroisoxazole(13p)

5-(3-{3-[3-(1,3-benzothiazol-2-yl)phenoxy]propoxy}-4-methoxyphenyl)-3-(3,4,5-trimethoxyphenyl)-4,5-dihydroisoxazole(13q)

5-(3-{4-[3-(1,3-benzothiazol-2-yl)phenoxy]butoxy}-4-methoxyphenyl)-3-(3,4,5-trimethoxyphenyl)-4,5-dihydroisoxazole(13r)

5-(3-{5-[3-(1,3-benzothiazol-2-yl)phenoxy]pentoxy}-4-methoxyphenyl)-3-(3,4,5-trimethoxyphenyl)-4,5-dihydroisoxazole(13s)

5-(3-{6-[3-(1,3-benzothiazol-2-yl)phenoxy]hexoxy}-4-methoxyphenyl)-3-(3,4,5-trimethoxyphenyl)-4,5-dihydroisoxazole(13t)

5-(3-{2-[4-(1,3-benzothiazol-2-yl)phenoxy]ethoxy}-4-methoxyphenyl)-3-(3,4,5-trimethoxyphenyl)isoxazole(14a)

5-(3-{3-[4-(1,3-benzothiazol-2-yl)phenoxy]propoxy}-4-methoxyphenyl)-3-(3,4,5-trimethoxyphenyl)isoxazole(14b)

5-(3-{4-[4-(1,3-benzothiazol-2-yl)phenoxy]butoxy}-4-methoxyphenyl)-3-(3,4,5-trimethoxyphenyl)isoxazole(14c)

5-(3-{5-[4-(1,3-benzothiazol-2-yl)phenoxy]pentoxy}-4-methoxyphenyl)-3-(3,4,5-trimethoxyphenyl)isoxazole(14d)

5-(3-{6-[4-(1,3-benzothiazol-2-yl)phenoxy]hexoxy}-4-methoxyphenyl)-3-(3,4,5-trimethoxyphenyl)isoxazole(14e)

5-(3-{2-[4-(1,3-benzothiazol-2-yl)-2-methoxyphenoxy]ethoxy}-4-methoxyphenyl)-3-(3,4,5-trimethoxyphenyl)isoxazole(14f)

5-(3-{3-[4-(1,3-benzothiazol-2-yl)-2-methoxyphenoxy]propoxy}-4-methoxyphenyl)-3-(3,4,5-trimethoxyphenyl)isoxazole(14g)

5-(3-{4-[4-(1,3-benzothiazol-2-yl)-2-methoxyphenoxy]butoxy}-4-methoxyphenyl)-3-(3,4,5-trimethoxyphenyl)isoxazole(14h)

5-(3-{5-[4-(1,3-benzothiazol-2-yl)-2-methoxyphenoxy]pentoxy}-4-methoxyphenyl)-3-(3,4,5-trimethoxyphenyl)isoxazole(14i)

5-(3-{6-[4-(1,3-benzothiazol-2-yl)-2-methoxyphenoxy]hexoxy}-4-methoxyphenyl)-3-(3,4,5-trimethoxyphenyl)isoxazole(14j)

5-(3-{2-[5-(1,3-benzothiazol-2-yl)-2-methoxyphenoxy]ethoxy}-4-methoxyphenyl)-3-(3,4,5-trimethoxyphenyl)isoxazole(14k)

5-(3-{3-[5-(1,3-benzothiazol-2-yl)-2-methoxyphenoxy]propoxy}-4-methoxyphenyl)-3-(3,4,5-trimethoxyphenyl)isoxazole(14l)

5-(3-{4-[5-(1,3-benzothiazol-2-yl)-2-methoxyphenoxy]butoxy}-4-methoxyphenyl)-3-(3,4,5-trimethoxyphenyl)isoxazole(14m)

5-(3-{5-[5-(1,3-benzothiazol-2-yl)-2-methoxyphenoxy]pentoxy}-4-methoxyphenyl)-3-(3,4,5-trimethoxyphenyl)isoxazole(14n)

5-(3-{6-[5-(1,3-benzothiazol-2-yl)-2-methoxyphenoxy]hexoxy}-4-methoxyphenyl)-3-(3,4,5-trimethoxyphenyl)isoxazole(14o)

5-(3-{2-[3-(1,3-benzothiazol-2-yl)phenoxy]ethoxy}-4-methoxyphenyl)-3-(3,4,5-trimethoxyphenyl)isoxazole(14p)

5-(3-{3-[3-(1,3-benzothiazol-2-yl)phenoxy]propoxy}-4-methoxyphenyl)-3-(3,4,5-trimethoxyphenyl)isoxazole(14q)

5-(3-{4-[3-(1,3-benzothiazol-2-yl)phenoxy]butoxy}-4-methoxyphenyl)-3-(3,4,5-trimethoxyphenyl)isoxazole (14r)

5-(3-{5-[3-(1,3-benzothiazol-2-yl)phenoxy]pentoxy}-4-methoxyphenyl)-3-(3,4,5-trimethoxyphenyl)isoxazole (14s)

5-(3-{6-[3-(1,3-benzothiazol-2-yl)phenoxy]hexoxy}-4-methoxyphenyl)-3-(3,4,5-trimethoxyphenyl)isoxazole (14t)

2-[3-methoxy-4-({2-[4-(2-{2-methoxy-5-[(Z)-2-(3,4,5-trimethoxyphenyl)-1-ethenyl]phenoxy}ethyl)piperazino]ethyl}oxy)phenyl]-1,3-benzothiazole(15a)

2-[3-methoxy-4-({3-[4-(3-{2-methoxy-5-[(Z)-2-(3,4,5-trimethoxyphenyl)-1-ethenyl]phenoxy}propyl)piperazino]propyl}oxy)phenyl]-1,3-benzothiazole(15b)

2-[3-methoxy-4-({4-[4-(4-{2-methoxy-5-[(Z)-2-(3,4,5-trimethoxyphenyl)-1-ethenyl]phenoxy}butyl)piperazino]butyl}oxy)phenyl]-1,3-benzothiazole(15c)

2-[3-methoxy-4-({5-[4-(5-{2-methoxy-5-[(Z)-2-(3,4,5-trimethoxyphenyl)-1-ethenyl]phenoxy}pentyl)piperazino]pentyl}oxy)phenyl]-1,3-benzothiazole(15d)

2-[3-methoxy-4-({6-[4-(6-{2-methoxy-5-[(Z)-2-(3,4,5-trimethoxyphenyl)-1-ethenyl]phenoxy}hexyl)piperazino]hexyl}oxy)phenyl]-1,3-benzothiazole(15e)

2-[4-({2-[4-(2-{2-methoxy-5-[(Z)-2-(3,4,5-trimethoxyphenyl)-1-ethenyl]phenoxy}ethyl)piperazino]ethyl}oxy)phenyl]-1,3-benzothiazole(15f)

2-[4-({3-[4-(3-{2-methoxy-5-[(Z)-2-(3,4,5-trimethoxyphenyl)-1-ethenyl]phenoxy}propyl)piperazino]propyl}oxy)phenyl]-1,3-benzothiazole(15g)

2-[4-({4-[4-(4-{2-methoxy-5-[(Z)-2-(3,4,5-trimethoxyphenyl)-1-ethenyl]phenoxy}butyl)piperazino]butyl}oxy)phenyl]-1,3-benzothiazole(15h)

2-[4-({5-[4-(5-{2-methoxy-5-[(Z)-2-(3,4,5-trimethoxyphenyl)-1-ethenyl]phenoxy}pentyl)piperazino]pentyl}oxy)phenyl]-1,3-benzothiazole(15i)

2-[4-({6-[4-(6-{2-methoxy-5-[(Z)-2-(3,4,5-trimethoxyphenyl)-1-ethenyl]phenoxy}hexyl)piperazino]hexyl}oxy)phenyl]-1,3-benzothiazole(15j)

2-[4-methoxy-3-({2-[4-(2-{2-methoxy-5-[(Z)-2-(3,4,5-trimethoxyphenyl)-1-ethenyl]phenoxy}ethyl)piperazino]ethyl}oxy)phenyl]-1,3-benzothiazole(15k)

2-[4-methoxy-3-({3-[4-(3-{2-methoxy-5-[(Z)-2-(3,4,5-trimethoxyphenyl)-1-ethenyl]phenoxy}propyl)piperazino]propyl}oxy)phenyl]-1,3-benzothiazole(15l)

2-[4-methoxy-3-({4-[4-(4-{2-methoxy-5-[(Z)-2-(3,4,5-trimethoxyphenyl)-1-ethenyl]phenoxy}butyl)piperazino]butyl}oxy)phenyl]-1,3-benzothiazole(15m)

2-[4-methoxy-3-({5-[4-(5-{2-methoxy-5-[(Z)-2-(3,4,5-trimethoxyphenyl)-1-ethenyl]phenoxy}pentyl)piperazino]pentyl}oxy)phenyl]-1,3-benzothiazole(15n)

2-[4-methoxy-3-({6-[4-(6-{2-methoxy-5-[(Z)-2-(3,4,5-trimethoxyphenyl)-1-ethenyl]phenoxy}hexyl)piperazino]hexyl}oxy)phenyl]-1,3-benzothiazole(15o)

2-[3-({2-[4-(2{-2-methoxy-5-[(Z)-2-(3,4,5-trimethoxyphenyl)-1-ethenyl]phenoxy}ethyl)piperazino]ethyl}oxy)phenyl]-1,3-benzothiazole(15p)

2-[3-({3-[4-(3{-2-methoxy-5-[(Z)-2-(3,4,5-trimethoxyphenyl)-1-ethenyl]phenoxy}propyl)piperazino]propyl}oxy)phenyl]-1,3-benzothiazole(15q)

2-[3-({4-[4-(4{-2-methoxy-5-[(Z)-2-(3,4,5-trimethoxyphenyl)-1-ethenyl]phenoxy}butyl)piperazino]butyl}oxy)phenyl]-1,3-benzothiazole(15r)

2-[3-({5-[4-(5{-2-methoxy-5-[(Z)-2-(3,4,5-trimethoxyphenyl)-1-ethenyl]phenoxy}pentyl)piperazino]pentyl}oxy)phenyl]-1,3-benzothiazole(15s)

2-[3-({6-[4-(6{-2-methoxy-5-[(Z)-2-(3,4,5-trimethoxyphenyl)-1-ethenyl]phenoxy}hexyl)piperazino]hexyl}oxy)phenyl]-1,3-benzothiazole(15t)

(E)-3-(3{-[2-(4-{2-[4-(1,3-benzothiazol-2-yl)-2-methoxyphenoxy]ethyl}piperazino)ethyl]oxy}-4-methoxyphenyl)-1-(3,4,5-trimethoxyphenyl)-2-propen-1-one(16a)

(E)-3-(3{-[3-(4-{3-[4-(1,3-benzothiazol-2-yl)-2-methoxyphenoxy]propyl}piperazino)propyl]oxy}methoxyphenyl)-1-(3,4,5-trimethoxyphenyl)-2-propen-1-one(16b)

(E)-3-(3{-[4-(4-{4-[4-(1,3-benzothiazol-2-yl)-2-methoxyphenoxy]butyl}piperazino)butyl]oxy}-4-methoxyphenyl)-1-(3,4,5-trimethoxyphenyl)-2-propen-1-one(16c)

(E)-3-(3{-[5-(4-{5-[4-(1,3-benzothiazol-2-yl)-2-methoxyphenoxy]pentyl}piperazino)pentyl]oxy}-methoxyphenyl)-1-(3,4,5-trimethoxyphenyl)-2-propen-1-one(16d)

(E)-3-(3{-[6-(4-{6-[4-(1,3-benzothiazol-2-yl)-2-methoxyphenoxy]hexyl}piperazino)hexyl]oxy}-4-methoxyphenyl)-1-(3,4,5-trimethoxyphenyl)-2-propen-1-one(16e)

(E)-3-(3{-[2-(4-{2-[4-(1,3-benzothiazol-2-yl)phenoxy]ethyl}piperazino)ethyl]oxy}-4-methoxyphenyl)-1-(3,4,5-trimethoxyphenyl)-2-propen-1-one(16f)

(E)-3-(3{-[3-(4-{3-[4-(1,3-benzothiazol-2-yl)phenoxy]propyl}piperazino)propyl]oxy}-4-methoxyphenyl)-1-(3,4,5-trimethoxyphenyl)-2-propen-1-one(16g)

(E)-3-(3{-[4-(4-{4-[4-(1,3-benzothiazol-2-yl)phenoxy]butyl}piperazino)butyl]oxy}-4-methoxyphenyl)-1-(3,4,5-trimethoxyphenyl)-2-propen-1-one(16h)

(E)-3-(3{-[5-(4-{5-[4-(1,3-benzothiazol-2-yl)phenoxy]pentyl}piperazino)pentyl]oxy}-4-methoxyphenyl)-1-(3,4,5-trimethoxyphenyl)-2-propen-1-one(16i)

(E)-3-(3{-[6-(4-{6-[4-(1,3-benzothiazol-2-yl)phenoxy]hexyl}piperazino)hexyl]oxy}-4-methoxyphenyl)-1-(3,4,5-trimethoxyphenyl)-2-propen-1-one(16j)

(E)-3-(3{-[2-(4-{2-[5-(1,3-benzothiazol-2-yl)-2-methoxyphenoxy]ethyl}piperazino)ethyl]oxy}-4-methoxyphenyl)-1-(3,4,5-trimethoxyphenyl)-2-propen-1-one(16k)

(E)-3-(3{-[3-(4-{3-[5-(1,3-benzothiazol-2-yl)-2-methoxyphenoxy]propyl}piperazino)propyl]oxy}-4-methoxyphenyl)-1-(3,4,5-trimethoxyphenyl)-2-propen-1-one (16l)

(E)-3-(3{-[4-(4-{4-[5-(1,3-benzothiazol-2-yl)-2-methoxyphenoxy]butyl}piperazino)butyl]oxy}-4-methoxyphenyl)-1-(3,4,5-trimethoxyphenyl)-2-propen-1-one(16m)

(E)-3-(3{-[5-(4-{5-[5-(1,3-benzothiazol-2-yl)-2-methoxyphenoxy]pentyl}piperazino)pentyl]oxy}-4-methoxyphenyl)-1-(3,4,5-trimethoxyphenyl)-2-propen-1-one (16n)

(E)-3-(3{-[6-(4-{6-[5-(1,3-benzothiazol-2-yl)-2-methoxyphenoxy]hexyl}piperazino)hexyl]oxy}-4-methoxyphenyl)-1-(3,4,5-trimethoxyphenyl)-2-propen-1-one(16o)

(E)-3-(3-{[2-(4-{2-[3-(1,3-benzothiazol-2-yl)phenoxy]ethyl}piperazino)ethyl]oxy}-4-methoxyphenyl)-1-(3,4,5-trimethoxyphenyl)-2-propen-1-one(16p)

(E)-3-(3-{[3-(4-{3-[3-(1,3-benzothiazol-2-yl)phenoxy]propyl}piperazino)propyl]oxy}-4-methoxyphenyl)-1-(3,4,5-trimethoxyphenyl)-2-propen-1-one(16q)

(E)-3-(3-{[4-(4-{4-[3-(1,3-benzothiazol-2-yl)phenoxy]butyl}piperazino)butyl]oxy}-4-methoxyphenyl)-1-(3,4,5-trimethoxyphenyl)-2-propen-1-one(16r)

(E)-3-(3-{[5-(4-{5-[3-(1,3-benzothiazol-2-yl)phenoxy]pentyl}piperazino)pentyl]oxy}-4-methoxyphenyl)-1-(3,4,5-trimethoxyphenyl)-2-propen-1-one(16s)

(E)-3-(3-{[6-(4-{6-[3-(1,3-benzothiazol-2-yl)phenoxy]hexyl}piperazino)hexyl]oxy}-4-methoxyphenyl)-1-(3,4,5-trimethoxyphenyl)-2-propen-1-one(16t)

1-[5-(3-{[2-(4-{2-[4-(1,3-benzothiazol-2-yl)-2-methoxyphenoxy]ethyl}piperazino)ethyl]oxy}-4-methoxyphenyl)-3-(3,4,5-trimethoxyphenyl)-4,5-dihydro-1H-1-pyrazolyl]-1-ethanone(17a)

1-[5-(3-{[3-(4-{3-[4-(1,3-benzothiazol-2-yl)-2-methoxyphenoxy]propyl}piperazino)propyl]oxy}-4-methoxyphenyl)-3-(3,4,5-trimethoxyphenyl)-4,5-dihydro-1H-1-pyrazolyl]-1-ethanone(17b)

1-[5-(3-{[4-(4-{4-[4-(1,3-benzothiazol-2-yl)-2-methoxyphenoxy]butyl}piperazino)butyl]oxy}-4-methoxyphenyl)-3-(3,4,5-trimethoxyphenyl)-4,5-dihydro-1H-1-pyrazolyl]-1-ethanone(17c)

1-[5-(3-{[5-(4-{5-[4-(1,3-benzothiazol-2-yl)-2-methoxyphenoxy]pentyl}piperazino)pentyl]oxy}-4-methoxyphenyl)-3-(3,4,5-trimethoxyphenyl)-4,5-dihydro-1H-1-pyrazolyl]-1-ethanone(17d)

1-[5-(3-{[6-(4-{6-[4-(1,3-benzothiazol-2-yl)-2-methoxyphenoxy]hexyl}piperazino)hexyl]oxy}-4-methoxyphenyl)-3-(3,4,5-trimethoxyphenyl)-4,5-dihydro-1H-1-pyrazolyl]-1-ethanone(17e)

1-[5-(3{-[2-(4-{2-[4-(1,3-benzothiazol-2-yl)phenoxy]ethyl}piperazino)ethyl]oxy}-4-methoxyphenyl)-3-(3,4,5-trimethoxyphenyl)-4,5-dihydro-1H-1-pyrazolyl]-1-ethanone(17f)

1-[5-(3{-[3-(4-{3-[4-(1,3-benzothiazol-2-yl)phenoxy]propyl}piperazino)propyl]oxy}-4-methoxyphenyl)-3-(3,4,5-trimethoxyphenyl)-4,5-dihydro-1H-1-pyrazolyl]-1-ethanone(17g)

1-[5-(3{-[4-(4-{4-[4-(1,3-benzothiazol-2-yl)phenoxy]butyl}piperazino)butyl]oxy}-4-methoxyphenyl)-3-(3,4,5-trimethoxyphenyl)-4,5-dihydro-1H-1-pyrazolyl]-1-ethanone(17h)

1-[5-(3{-[5-(4-{5-[4-(1,3-benzothiazol-2-yl)phenoxy]pentyl}piperazino)pentyl]oxy}-4-methoxyphenyl)-3-(3,4,5-trimethoxyphenyl)-4,5-dihydro-1H-1-pyrazolyl]-1-ethanone(17i)

1-[5-(3{-[6-(4-{6-[4-(1,3-benzothiazol-2-yl)phenoxy]hexyl}piperazino)hexyl]oxy}-4-methoxyphenyl)-3-(3,4,5-trimethoxyphenyl)-4,5-dihydro-1H-1-pyrazolyl]-1-ethanone(17j)

1-[5-(3-{[2-(4-{2-[5-(1,3-benzothiazol-2-yl)-2-methoxyphenoxy]ethyl}piperazino)ethyl]oxy}-4-methoxyphenyl)-3-(3,4,5-trimethoxyphenyl)-4,5-dihydro-1H-1-pyrazolyl]-1-ethanone(17k)

1-[5-(3-{[3-(4-{3-[5-(1,3-benzothiazol-2-yl)-2-methoxyphenoxy]propyl}piperazino)propyl]oxy}-4-methoxyphenyl)-3-(3,4,5-trimethoxyphenyl)-4,5-dihydro-1H-1-pyrazolyl]-1-ethanone(17l)

1-[5-(3-{[4-(4-{4-[5-(1,3-benzothiazol-2-yl)-2-methoxyphenoxy]butyl}piperazino)butyl]oxy}-4-methoxyphenyl)-3-(3,4,5-trimethoxyphenyl)-4,5-dihydro-1H-1-pyrazolyl]-1-ethanone(17m)

1-[5-(3-{[5-(4-{5-[5-(1,3-benzothiazol-2-yl)-2-methoxyphenoxy]pentyl}piperazino)pentyl]oxy}-4-methoxyphenyl)-3-(3,4,5-trimethoxyphenyl)-4,5-dihydro-1H-1-pyrazolyl]-1-ethanone(17n)

1-[5-(3-{[6-(4-{6-[5-(1,3-benzothiazol-2-yl)-2-methoxyphenoxy]hexyl}piperazino)hexyl]oxy}-4-methoxyphenyl)-3-(3,4,5-trimethoxyphenyl)-4,5-dihydro-1H-1-pyrazolyl]-1-ethanone(17o)

1-[5-(3-{[2-(4-{2-[3-(1,3-benzothiazol-2-yl)phenoxy]ethyl}piperazino)ethyl]oxy}-4-methoxyphenyl)-3-(3,4,5-trimethoxyphenyl)-4,5-dihydro-1H-1-pyrazolyl]-1-ethanone(17p)

1-[5-(3-{[3-(4-{3-[3-(1,3-benzothiazol-2-yl)phenoxy]propyl}piperazino)propyl]oxy}-4-methoxyphenyl)-3-(3,4,5-trimethoxyphenyl)-4,5-dihydro-1H-1-pyrazolyl]-1-ethanone(17q)

1-[5-(3-{[4-(4-{4-[3-(1,3-benzothiazol-2-yl)phenoxy]butyl}piperazino) butyl]oxy}-4-methoxyphenyl)-3-(3,4,5-trimethoxyphenyl)-4,5-dihydro-1H-1-pyrazolyl]-1-ethanone(17r)

1-[5-(3-{[5-(4-{5-[3-(1,3-benzothiazol-2-yl)phenoxy]pentyl}piperazino)pentyl]oxy}-4-methoxyphenyl)-3-(3,4,5-trimethoxyphenyl)-4,5-dihydro-1H-1-pyrazolyl]-1-ethanone(17s)

1-[5-(3-{[6-(4-{6-[3-(1,3-benzothiazol-2-yl)phenoxy]hexyl}piperazino)hexyl]oxy}-4-methoxyphenyl)-3-(3,4,5-trimethoxyphenyl)-4,5-dihydro-1H-1-pyrazolyl]-1-ethanone(17t)

1-[5-(3-{[2-(4-{2-[4-(1,3-benzothiazol-2-yl)-2-methoxyphenoxy]ethyl}piperazino)ethyl]oxy}-4-methoxyphenyl)-3-(3,4,5-trimethoxyphenyl)-1H-1-pyrazolyl]-1-ethanone(18a)

1-[5-(3-{[3-(4-{3-[4-(1,3-benzothiazol-2-yl)-2-methoxyphenoxy]propyl}piperazino)propyl]oxy}-4-methoxyphenyl)-3-(3,4,5-trimethoxyphenyl)-1H-1-pyrazolyl]-1-ethanone(18b)

1-[5-(3-{[4-(4-{4-[4-(1,3-benzothiazol-2-yl)-2-methoxyphenoxy]butyl}piperazino)butyl]oxy}-4-methoxyphenyl)-3-(3,4,5-trimethoxyphenyl)-1H-1-pyrazolyl]-1-ethanone(18c)

1-[5-(3-{[5-(4-{5-[4-(1,3-benzothiazol-2-yl)-2-methoxyphenoxy]pentyl}piperazino)pentyl]oxy}-4-methoxyphenyl)-3-(3,4,5-trimethoxyphenyl)-1H-1-pyrazolyl]-1-ethanone(18d)

1-[5-(3-{[6-(4-{6-[4-(1,3-benzothiazol-2-yl)-2-methoxyphenoxy]hexyl}piperazinohexyl]oxy}-4-methoxyphenyl)-3-(3,4,5-trimethoxyphenyl)-1H-1-pyrazolyl]-1-ethanone(18e)

1-[5-(3{-[2-(4-{2-[4-(1,3-benzothiazol-2-yl)phenoxy]ethyl}piperazino)ethyl]oxy}-4-methoxyphenyl)-3-(3,4,5-trimethoxyphenyl)-1H-1-pyrazolyl]-1-ethanone(18f)

1-[5-(3{-[3-(4-{3-[4-(1,3-benzothiazol-2-yl)phenoxy]propyl}piperazino)propyl]oxy}-4-methoxyphenyl)-3-(3,4,5-trimethoxyphenyl)-1H-1-pyrazolyl]-1-ethanone(18g)

1-[5-(3{-[4-(4-{4-[4-(1,3-benzothiazol-2-yl)phenoxy]butyl}piperazino)butyl]oxy}-4-methoxyphenyl)-3-(3,4,5-trimethoxyphenyl)-1H-1-pyrazolyl]-1-ethanone(18h)

1-[5-(3{-[5-(4-{5-[4-(1,3-benzothiazol-2-yl)phenoxy]pentyl}piperazino)pentyl]oxy}-4-methoxyphenyl)-3-(3,4,5-trimethoxyphenyl)-1H-1-pyrazolyl]-1-ethanone(18i)

1-[5-(3{-[6-(4-{6-[4-(1,3-benzothiazol-2-yl)phenoxy]hexyl}piperazino)hexyl]oxy}-4-methoxyphenyl)-3-(3,4,5-trimethoxyphenyl)-1H-1-pyrazolyl]-1-ethanone(18j)

1-[5-(3-{[2-(4-{2-[5-(1,3-benzothiazol-2-yl)-2-methoxyphenoxy]ethyl}piperazino)ethyl]oxy}-4-methoxyphenyl)-3-(3,4,5-trimethoxyphenyl)-1H-1-pyrazolyl]-1-ethanone(18k)

1-[5-(3-{[3-(4-{3-[5-(1,3-benzothiazol-2-yl)-2-methoxyphenoxy]propyl}piperazino)propyl]oxy}-4-methoxyphenyl)-3-(3,4,5-trimethoxyphenyl)-1H-1-pyrazolyl]-1-ethanone(18l)

1-[5-(3-{[4-(4-{4-[5-(1,3-benzothiazol-2-yl)-2-methoxyphenoxy]butyl}piperazino)butyl]oxy}-4-methoxyphenyl)-3-(3,4,5-trimethoxyphenyl)-1H-1-pyrazolyl]-1-ethanone(18m)

1-[5-(3-{[5-(4-{5-[5-(1,3-benzothiazol-2-yl)-2-methoxyphenoxy]pentyl}piperazino)pentyl]oxy}-4-methoxyphenyl)-3-(3,4,5-trimethoxyphenyl)-1H-1-pyrazolyl]-1-ethanone(18n)

1-[5-(3-{[6-(4-{6-[5-(1,3-benzothiazol-2-yl)-2-methoxyphenoxy]hexyl}piperazino)hexyl]oxy}-4-methoxyphenyl)-3-(3,4,5-trimethoxyphenyl)-1H-1-pyrazolyl]-1-ethanone(18o)

1-[5-(3-{[2-(4-{2-[3-(1,3-benzothiazol-2-yl)phenoxy]ethyl}piperazino)ethyl]oxy}-4-methoxyphenyl)-3-(3,4,5-trimethoxyphenyl)-1H-1-pyrazolyl]-1-ethanone(18p)

1-[5-(3-{[3-(4-{3-[3-(1,3-benzothiazol-2-yl)phenoxy]propyl}piperazino)propyl]oxy}-4-methoxyphenyl)-3-(3,4,5-trimethoxyphenyl)-1H-1-pyrazolyl]-1-ethanone(18q)

1-[5-(3-{[4-(4-{4-[3-(1,3-benzothiazol-2-yl)phenoxy]butyl}piperazino)butyl]oxy}-4-methoxyphenyl)-3-(3,4,5-trimethoxyphenyl)-1H-1-pyrazolyl]-1-ethanone(18r)

1-[5-(3-{[5-(4-{5-[3-(1,3-benzothiazol-2-yl)phenoxy]pentyl}piperazino)pentyl]oxy}-4-methoxyphenyl)-3-(3,4,5-trimethoxyphenyl)-1H-1-pyrazolyl]-1-ethanone(18s)

1-[5-(3-{[6-(4-{6-[3-(1,3-benzothiazol-2-yl)phenoxy]hexyl}piperazino)hexyl]oxy}-4-methoxyphenyl)-3-(3,4,5-trimethoxyphenyl)-1H-1-pyrazolyl]-1-ethanone(18t)

5-(3-{[2-(4-{2-[4-(1,3-benzothiazol-2-yl)-2-methoxyphenoxy]ethyl}piperazino)ethyl]oxy}-4-methoxyphenyl)-3-(3,4,5-trimethoxyphenyl)-4,5-dihydroisoxazole(19a)

5-(3-{[3-(4-{3-[4-(1,3-benzothiazol-2-yl)-2-methoxyphenoxy]propyl}piperazino)propyl]oxy}-4-methoxyphenyl)-3-(3,4,5-trimethoxyphenyl)-4,5-dihydroisoxazole(19b)

5-(3-{[4-(4-{4-[4-(1,3-benzothiazol-2-yl)-2-methoxyphenoxy]butyl}piperazino) butyl]oxy}-4-methoxyphenyl)-3-(3,4,5-trimethoxyphenyl)-4,5-dihydroisoxazole(19c)

5-(3-{[5-(4-{5-[4-(1,3-benzothiazol-2-yl)-2-methoxyphenoxy]pentyl}piperazino)pentyl]oxy}-4-methoxyphenyl)-3-(3,4,5-trimethoxyphenyl)-4,5-dihydroisoxazole(19d)

5-(3-{[6-(4-{6-[4-(1,3-benzothiazol-2-yl)-2-methoxyphenoxy]hexyl}piperazino)hexyl]oxy}-4-methoxyphenyl)-3-(3,4,5-trimethoxyphenyl)-4,5-dihydroisoxazole(19e)

5-(3-{[2-(4-{2-[4-(1,3-benzothiazol-2-yl)phenoxy]ethyl}piperazino)ethyl]oxy}-4-methoxyphenyl)-3-(3,4,5-trimethoxyphenyl)-4,5-dihydroisoxazole(19f)

5-(3-{[3-(4-{3-[4-(1,3-benzothiazol-2-yl)phenoxy]propyl}piperazino)propyl]oxy}-4-methoxyphenyl)-3-(3,4,5-trimethoxyphenyl)-4,5-dihydroisoxazole(19g)

5-(3-{[4-(4-{4-[4-(1,3-benzothiazol-2-yl)phenoxy]butyl}piperazino)butyl]oxy}-4-methoxyphenyl)-3-(3,4,5-trimethoxyphenyl)-4,5-dihydroisoxazole(19h)

5-(3-{[5-(4-{5-[4-(1,3-benzothiazol-2-yl)phenoxy]pentyl}piperazino)pentyl]oxy}-4-methoxyphenyl)-3-(3,4,5-trimethoxyphenyl)-4,5-dihydroisoxazole(19i)

5-(3-{[6-(4-{6-[4-(1,3-benzothiazol-2-yl)phenoxy]hexyl}piperazino)hexyl]oxy}-4-methoxyphenyl)-3-(3,4,5-trimethoxyphenyl)-4,5-dihydroisoxazole(19j)

5-(3-{[2-(4-{2-[5-(1,3-benzothiazol-2-yl)-2-methoxyphenoxy]ethyl}piperazino)ethyl]oxy}-4-methoxyphenyl)-3-(3,4,5-trimethoxyphenyl)-4,5-dihydroisoxazole (19k)

5-(3-{[3-(4-{3-[5-(1,3-benzothiazol-2-yl)-2-methoxyphenoxy]propyl}piperazino)propyl]oxy}-4-methoxyphenyl)-3-(3,4,5-trimethoxyphenyl)-4,5-dihydroisoxazole (19l)

5-(3-{[4-(4-{4-[5-(1,3-benzothiazol-2-yl)-2-methoxyphenoxy]butyl}piperazino) butyl]oxy}-4-methoxyphenyl)-3-(3,4,5-trimethoxyphenyl)-4,5-dihydroisoxazole (19m)

5-(3-{[5-(4-{5-[5-(1,3-benzothiazol-2-yl)-2-methoxyphenoxy]pentyl}piperazino)pentyl]oxy}-4-methoxyphenyl)-3-(3,4,5-trimethoxyphenyl)-4,5-dihydroisoxazole (19n)

5-(3-{[6-(4-{6-[5-(1,3-benzothiazol-2-yl)-2-methoxyphenoxy]hexyl}piperazino)hexyl]oxy}-4-methoxyphenyl)-3-(3,4,5-trimethoxyphenyl)-4,5-dihydroisoxazole (19o)

5-(3-{[2-(4-{2-[3-(1,3-benzothiazol-2-yl)phenoxy]ethyl}piperazino)ethyl]oxy}-4-methoxyphenyl)-3-(3,4,5-trimethoxyphenyl)-4,5-dihydroisoxazole(19p)

5-(3-{[3-(4-{3-[3-(1,3-benzothiazol-2-yl)phenoxy]propyl}piperazino)propyl]oxy}-4-methoxyphenyl)-3-(3,4,5-trimethoxyphenyl)-4,5-dihydroisoxazole(19q)

5-(3-{[4-(4-{4-[3-(1,3-benzothiazol-2-yl)phenoxy]butyl}piperazino)butyl]oxy}-4-methoxyphenyl)-3-(3,4,5-trimethoxyphenyl)-4,5-dihydroisoxazole(19r)

5-(3-{[5-(4-{5-[3-(1,3-benzothiazol-2-yl)phenoxy]pentyl}piperazino)pentyl]oxy}-4-methoxyphenyl)-3-(3,4,5-trimethoxyphenyl)-4,5-dihydroisoxazole(19s)

5-(3-{[6-(4-{6-[3-(1,3-benzothiazol-2-yl)phenoxy]hexyl}piperazino)hexyl]oxy}-4-methoxyphenyl)-3-(3,4,5-trimethoxyphenyl)-4,5-dihydroisoxazole(19t)

5-(3-{[2-(4-{2-[4-(1,3-benzothiazol-2-yl)-2-methoxyphenoxy]ethyl}piperazino)ethyl]oxy}-4-methoxyphenyl)-3-(3,4,5-trimethoxyphenyl)isoxazole(20a)

5-(3-{[3-(4-{3-[4-(1,3-benzothiazol-2-yl)-2-methoxyphenoxy]propyl}piperazino)propyl]oxy}-4-methoxyphenyl)-3-(3,4,5-trimethoxyphenyl)isoxazole(20b)

5-(3-{[4-(4-{4-[4-(1,3-benzothiazol-2-yl)-2-methoxyphenoxy]butyl}piperazino) butyl]oxy}-4-methoxyphenyl)-3-(3,4,5-trimethoxyphenyl)isoxazole(20c)

5-(3-{[5-(4-{5-[4-(1,3-benzothiazol-2-yl)-2-methoxyphenoxy]pentyl}piperazino)pentyl]oxy}-4-methoxyphenyl)-3-(3,4,5-trimethoxyphenyl)isoxazole(20d)

5-(3-{[6-(4-{6-[4-(1,3-benzothiazol-2-yl)-2-methoxyphenoxy]hexyl}piperazino)hexyl]oxy}-4-methoxyphenyl)-3-(3,4,5-trimethoxyphenyl)isoxazole(20e)

5-(3-{[2-(4-{2-[4-(1,3-benzothiazol-2-yl)phenoxy]ethyl}piperazino)ethyl]oxy}-4-methoxyphenyl)-3-(3,4,5-trimethoxyphenyl)isoxazole(20f)

5-(3-{[3-(4-{3-[4-(1,3-benzothiazol-2-yl)phenoxy]propyl}piperazino)propyl]oxy}-4-methoxyphenyl)-3-(3,4,5-trimethoxyphenyl)isoxazole(20g)

5-(3-{[4-(4-{4-[4-(1,3-benzothiazol-2-yl)phenoxy]butyl}piperazino)butyl]oxy}-4-methoxyphenyl)-3-(3,4,5-trimethoxyphenyl)isoxazole(20h)

5-(3-{[5-(4-{5-[4-(1,3-benzothiazol-2-yl)phenoxy]pentyl}piperazino)pentyl]oxy}-4-methoxyphenyl)-3-(3,4,5-trimethoxyphenyl)isoxazole(20i)

5-(3-{[6-(4-{6-[4-(1,3-benzothiazol-2-yl)phenoxy]hexyl}piperazino)hexyl]oxy}-4-methoxyphenyl)-3-(3,4,5-trimethoxyphenyl)isoxazole(20j)

5-(3-{[2-(4-{2-[5-(1,3-benzothiazol-2-yl)-2-methoxyphenoxy]ethyl}piperazino)ethyl]oxy}-4-methoxyphenyl)-3-(3,4,5-trimethoxyphenyl)isoxazole(20k)

5-(3-{[3-(4-{3-[5-(1,3-benzothiazol-2-yl)-2-methoxyphenoxy]propyl}piperazino)propyl]oxy}-4-methoxyphenyl)-3-(3,4,5-trimethoxyphenyl)isoxazole(20l)

5-(3-{[4-(4-{4-[5-(1,3-benzothiazol-2-yl)-2-methoxyphenoxy]butyl}piperazino) butyl]oxy}-4-methoxyphenyl)-3-(3,4,5-trimethoxyphenyl)isoxazole(20m)

5-(3-{[5-(4-{5-[5-(1,3-benzothiazol-2-yl)-2-methoxyphenoxy]pentyl}piperazino) pentyl]oxy}-4-methoxyphenyl)-3-(3,4,5-trimethoxyphenyl)isoxazole(20n)

5-(3-{[6-(4-{6-[5-(1,3-benzothiazol-2-yl)-2-methoxyphenoxy]hexyl}piperazino) hexyl]oxy}-4-methoxyphenyl)-3-(3,4,5-trimethoxyphenyl)isoxazole(20o)

5-(3-{[2-(4-{2-[3-(1,3-benzothiazol-2-yl)phenoxy]ethyl}piperazino)ethyl]oxy}-4-methoxyphenyl)-3-(3,4,5-trimethoxyphenyl)isoxazole(20p)

5-(3-{[3-(4-{3-[3-(1,3-benzothiazol-2-yl)phenoxy]propyl}piperazino)propyl]oxy}-4-methoxyphenyl)-3-(3,4,5-trimethoxyphenyl)isoxazole(20q)

5-(3-{[4-(4-{4-[3-(1,3-benzothiazol-2-yl)phenoxy]butyl}piperazino)butyl]oxy}-4-methoxyphenyl)-3-(3,4,5-trimethoxyphenyl)isoxazole(20r)

5-(3-{[5-(4-{5-[3-(1,3-benzothiazol-2-yl)phenoxy]
pentyl}piperazino)pentyl]oxy}-4-methoxyphenyl)-3-(3,
4,5-trimethoxyphenyl)isoxazole(20s)

5-(3-{[6-(4-{6-[3-(1,3-benzothiazol-2-yl)phenoxy]
hexyl}piperazino)hexyl]oxy}-4-methoxyphenyl)-3-(3,4,
5-trimethoxyphenyl)isoxazole(20t)

In an embodiment of the present invention Benzothiazole hybrids of general formulae A are useful as antitumor agents.

In an embodiment of the present invention Benzothiazole hybrids exhibiting invitro anticancer activity against human tumor cell lines selected from the group consisting of lung cancer, colon cancer, CNS cancer, ovarian cancer, prostate cancer and breast cancer.

In an embodiment of the present invention the percentage growth inhibition of compounds 9b, 9h, 9m, 9r, 15c, 15h, 15m, 15r, 10b, 10h, 10m, 10r, 16c, 16h, 16m for invitro anticancer activity is in the range of 1-100 at 10 µM concentration at an exposure period of at least 48 hrs.

In an embodiment of the present invention A process for the preparation of benzothiazole hybrids of general formulae A Formula A

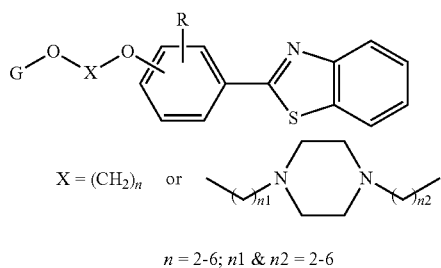

$X = (CH_2)_n$ or 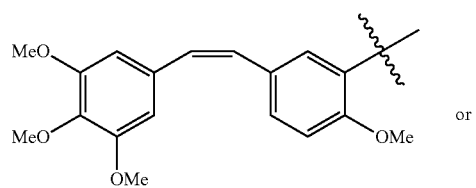

$n = 2\text{-}6; n1 \ \& \ n2 = 2\text{-}6$

Where in R = H or methoxy and
G =

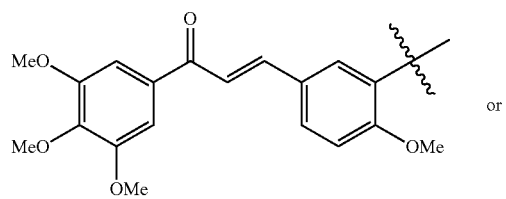

or

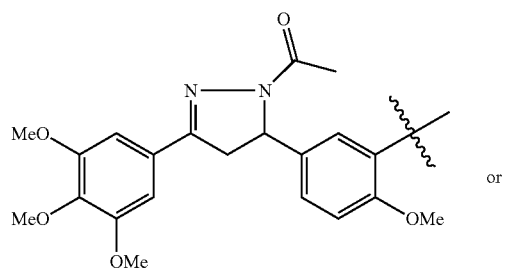

or

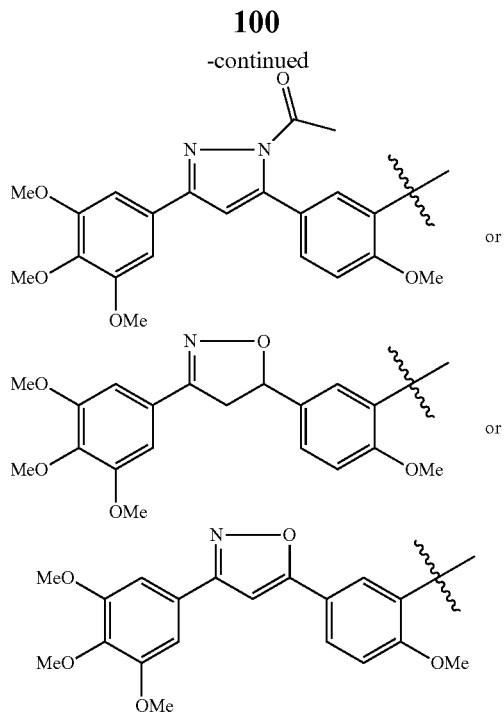

and the said process comprising steps of
A) reacting benzothiazole derivatives of formula 7 and 8

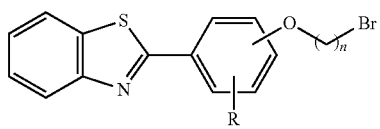 7

$n = 2\text{-}6$

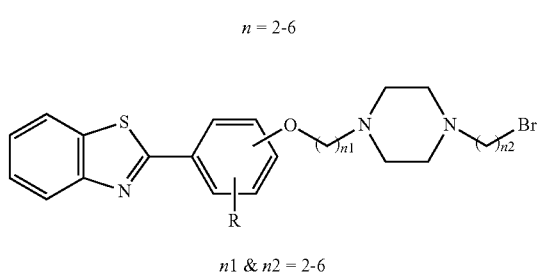 8

$n1 \ \& \ n2 = 2\text{-}6$ with the compounds of formulae 1, 2, 3, 4, 5 and 6

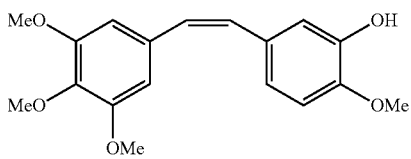 1

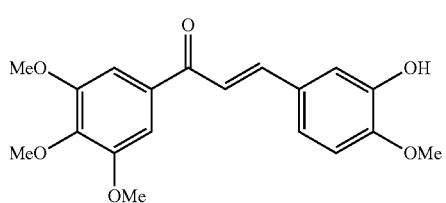 2

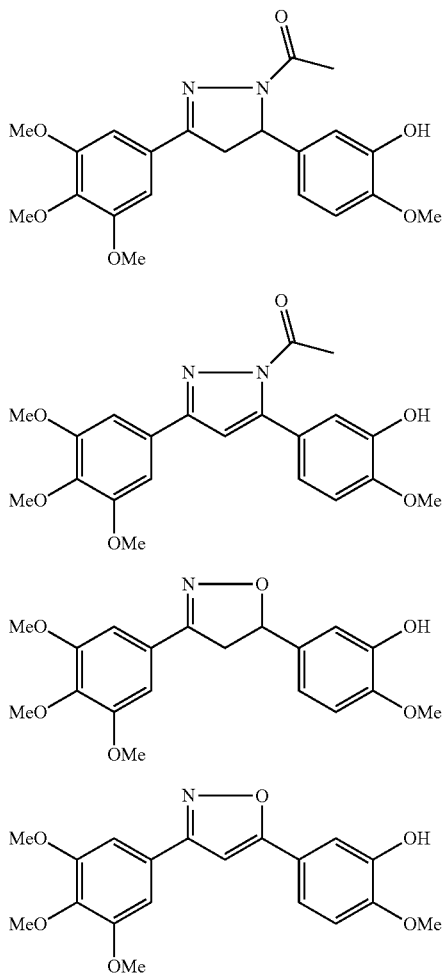

B) in an organic solvent in the presence of inorganic base selected from the group consisting of potassium carbonate or sodium carbonate at temperature range of 25-35° C. for a period of about 22-26 h, C) followed by adding water, extracting with organic solvent and evaporating the organic solvent to obtain the resultant crude product D) and purifying it by column chromatography to obtain the desired products of formulae A.

In an embodiment of the present invention the molar ratios of compound of formula 7 or 8 are 1.0 mmol with the compounds of formula 1, 2, 3, 4, 5 or 6 are 1.0-2.0 mmol and inorganic base is 1.0-6.0 mmol.

In an embodiment of the present invention the reaction in step (a) is performed for a period of about 22-26 h.

In an embodiment of the present invention the organic solvent used is selected from the group consisting of N,N-dimethylformamide, acetone, acetonitrile, dimethyl sulfoxide and ethyl acetate.

DETAILED DESCRIPTION OF THE INVENTION

Figure 1:
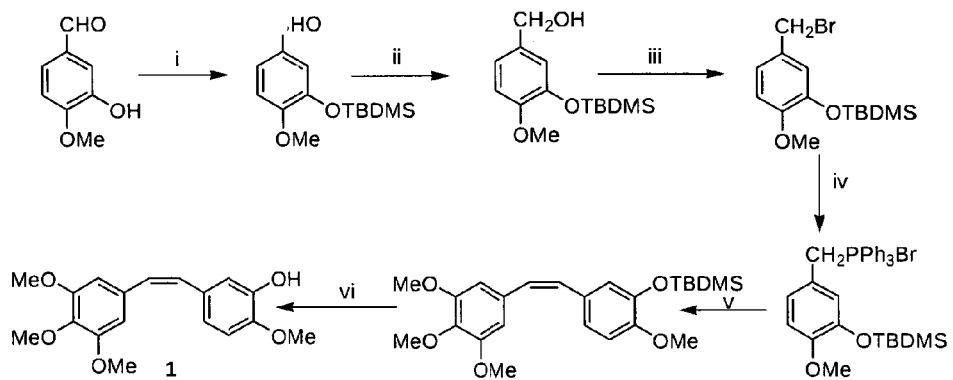
FIG. 1: depicts the process for the preparation of the compound 2-methoxy-5-[(Z)-2-(3,4,5-trimethoxyphenyl)-1-ethenyl]phenol (1).
Figure 2:
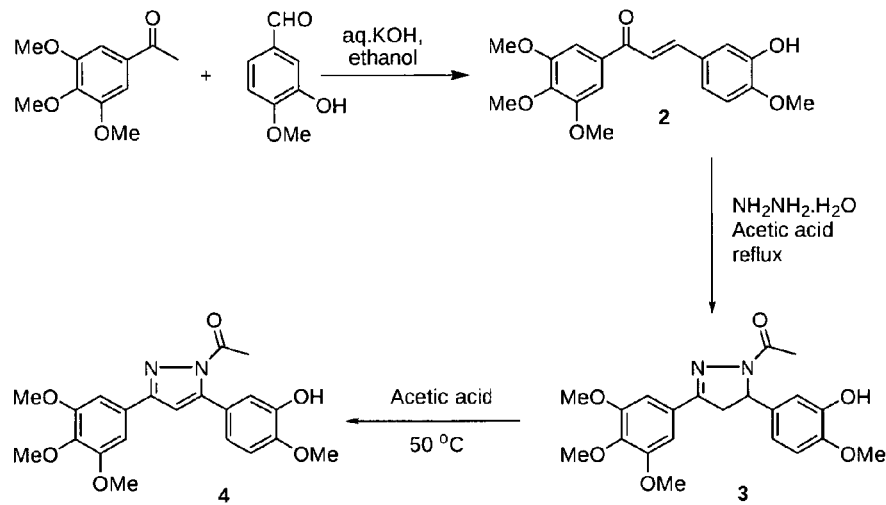
FIG. 2: depicts the process for the preparation of the compound 1-(5-(3-hydroxy-4-methoxyphenyl)-3-(3,4,5-trimethoxyphenyl)-1H-pyrazol-1-yl)ethanone (4).
Figure 3:
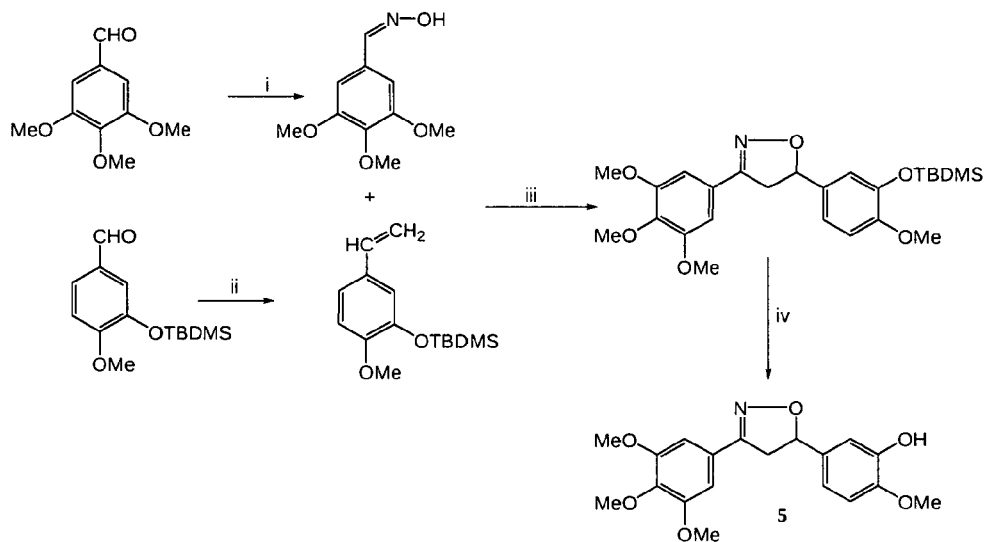
FIG. 3 depicts the process for the preparation of the compound 2-methoxy-5-(3-(3,4,5-trimethoxyphenyl)-4,5-dihydroisoxazol-5-yl)phenol (5).
Figure 4:
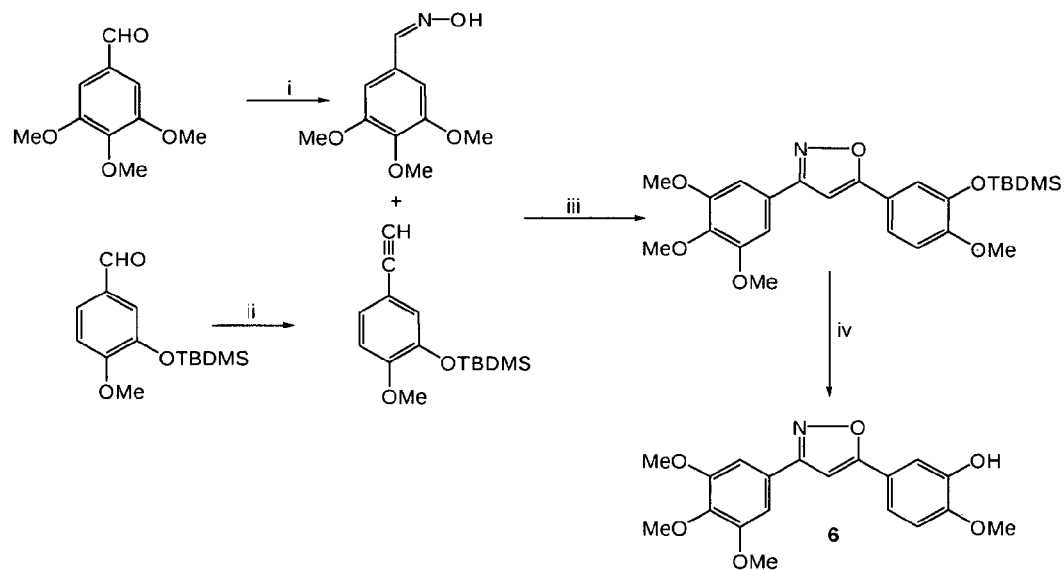
FIG. 4 depicts the process for the preparation of the compound 2-methoxy-5-(3-(3,4,5-trimethoxyphenyl)isoxazol-5-yl)phenol (6).
Figure 5:
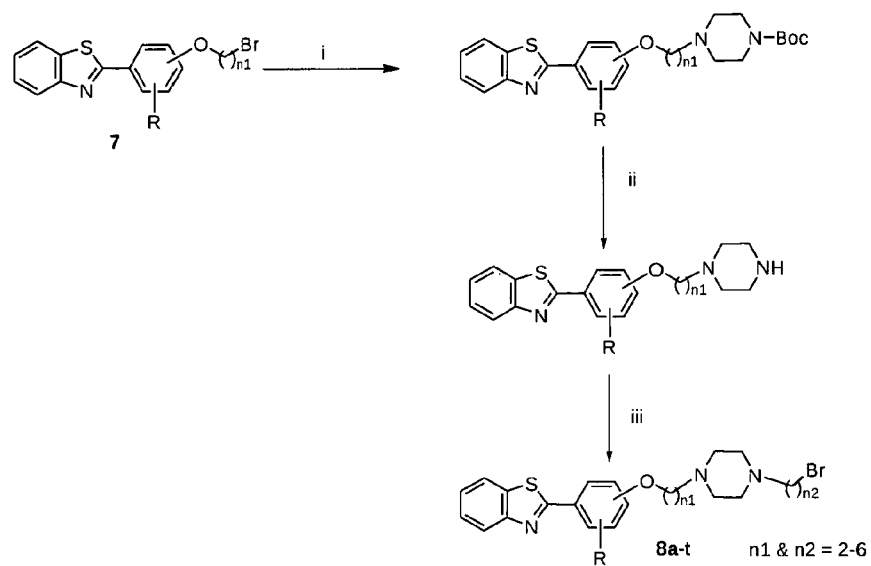
FIG. 5 depicts the process for the preparation of compounds 8a-t.
Figure 6:
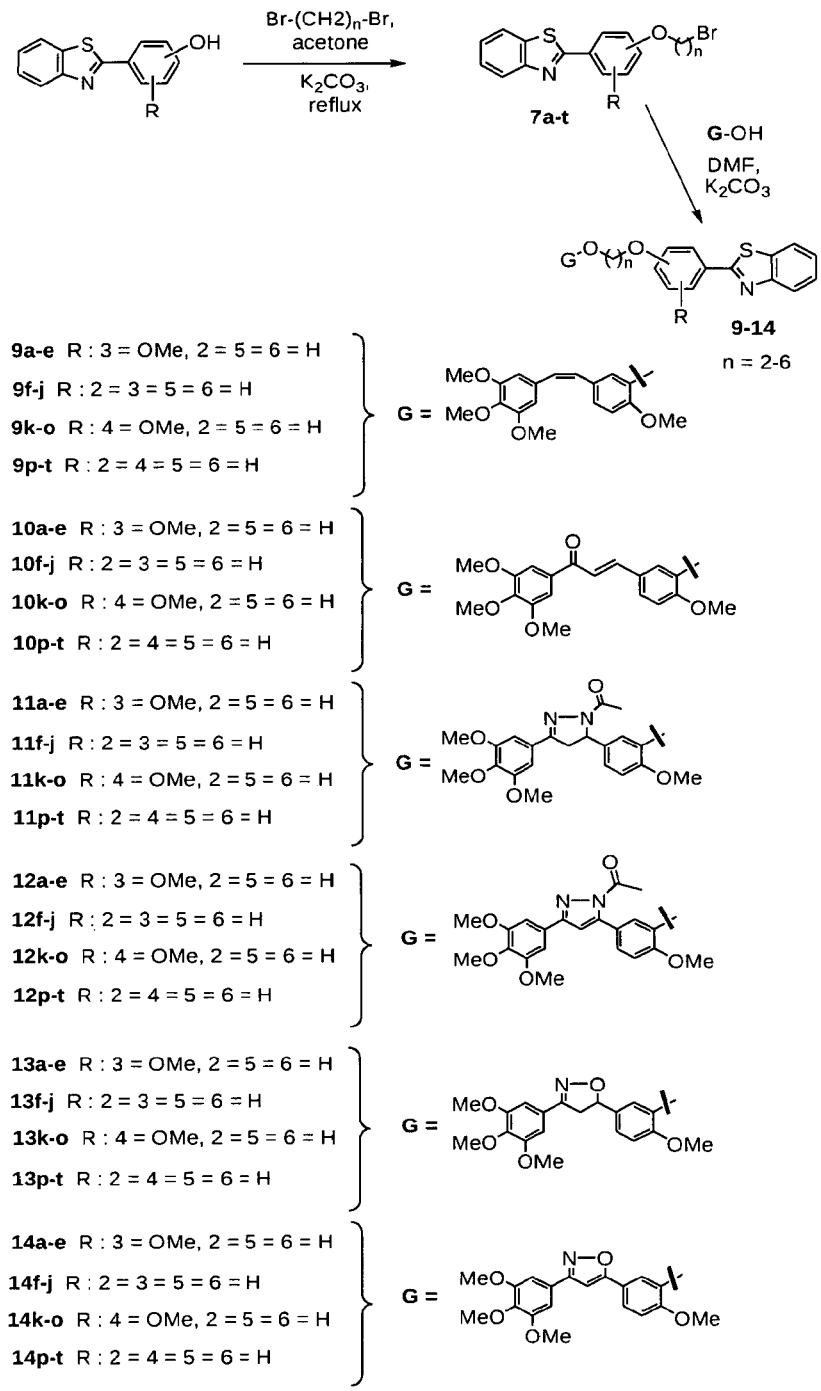
FIG. 6 depicts the process for the preparation of compounds 9-14.
Figure 7:
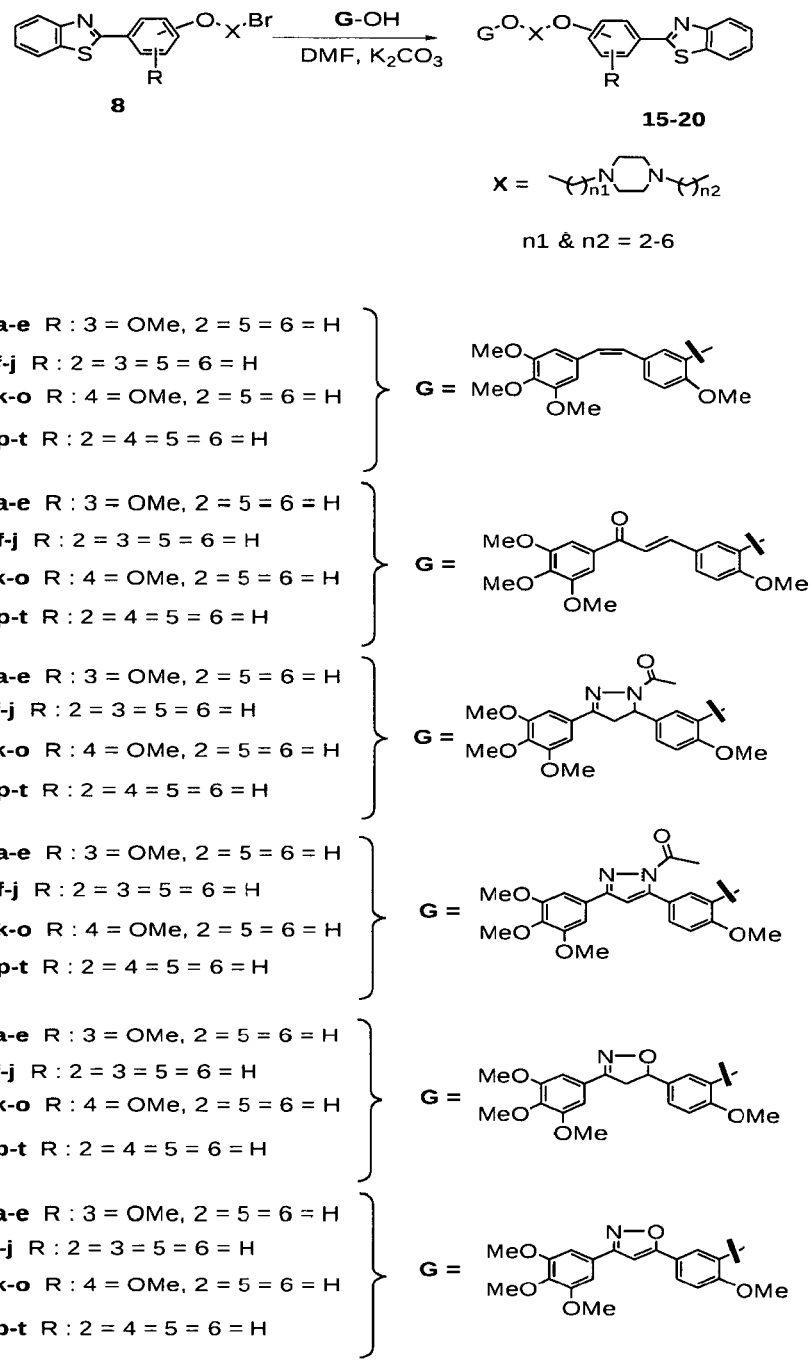
FIG. 7 depicts the process for the preparation of compounds 15-20.

The precursors of phenyl benzothiazole derivatives of formula 7, has been prepared using literature method (Ben-Allum, A.; Bakkas, S.; Soufiaoui, M. *Tetrahedron Lett.* 1997, 38, 6395; Wells, G.; Lowe, P. R.; Stevens, M. F. G. *ARKIVOC* 2000, 1, 779) and the precursors of phenyl benzothiazole derivatives of piperazine of formula 8 have been prepared by as shown in scheme-5. The precursors olefine, chalcone, pyrazoline, pyrazole, isoxazoline and isoxazole of formulae 1, 2, 3, 4, 5 and 6 have been prepared using literature methods or as shown in schemes (Sylvie Ducki, David Rennison, Meiko Woo, Alexander Kendall, Jérémie Fournier Dit Chabert, Alan T. McGown, Nicholas J. Lawrence. *Bioorg. Med. Chem,* 17, 2009, 7698-7710; Regan LeBlanc, John Dickson, Toni Brown, Michelle Stewart, Hari N. Pati, Don VanDerveer, Hadi Arman, Jeff Harris, William Pennington, Herman L. Holt Jr., Moses Lee. *Bioorg. Med. Chem,* 13, 2005, 6025-6034; Marlie Johnson, Brent Younglove, Lauren Lee, Regan LeBlanc, Herman Holt Jr., Patrice Hills, Hilary Mackay, Toni Brown, Susan L. Mooberry, Moses Lee. *Bioorg. Med. Chem. Lett,* 17, 2007, 5897-5901; B. A. Bhat, K. L. Dhar, S. C. Puri, A. K. Saxena, M. Shanmugavel, G. N. Qazi. *Bioorg. Med. Chem. Lett,* 15, 2005, 3177-3180; Gian Ceasure Tron, Tracy Pirali, Giovanni sorba, Francesca pagliai, Sara Buasacca and Armado A. Genazzani. *J. Med. Chem.* 2006, 49, 3033-3044.; Tracey Pirali, Sara buasacca, Lorena Beltrami, Daniela Imovilli, Francesca Paliai, Gianluca Migilio, Alberto Massrotti, Luisella Verotta, Gian Cesare Tron, Givanni Sorba, and Armado A. Genazzani. *J. Med. Chem.* 2006, 49, 5372-5376; Julia kaffy, Renee Pontikis, Daniele Carrez, Alain Croisy, Claude Monneret and Jean-Claude Florent. *Bioorg. Med. Chem.* 2006, 14, 4067-4077, Simoni, D.; Grisolia, G.; Giannini, G.; Roberti, M.; Rondanin, R.; Piccagli, L.; Baruchello, R.; Rossi, M.; Romagnoli, R.; Invidiata, F. P.; Grimaudo, S.; Jung, M. K.; Hamel, E.; Gebbia, N.; Crosta, L.; Abbadessa, V.; DiCristina, A.; Dusonchet, L.; Meli, M.; Tolomeo, M. *J. Med. Chem.* 2005, 48, 723).

These new analogues of olefine, chalcone, pyrazoline, pyrazole, isoxazole and isoxazoline linked benzothiazole hybrids have shown promising anticancer activity in various cell lines. The molecules synthesized are of immense biological significance.

The following examples are given by way of illustration and therefore should not be construed to the present limit of the scope of invention.

Example 1

2-[3-methoxy-4-(3-2-methoxy-5-[(Z)-2-(3,4,5-trimethoxyphenyl)-1-ethenyl]phenoxypropoxy)phenyl]-1,3-benzothiazole (9b)

2-methoxy-5-[(Z)-2-(3,4,5-trimethoxyphenyl)-1-ethenyl]phenol (1) (316 mg, 1.0 mmol) in DMF (20 mL) was added anhydrous potassium carbonate (690 mg, 5.0 mmol) and 2-[4-(3-bromopropoxy)-3-methoxyphenyl]-1,3-benzothiazole (7b) (378 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using ethyl acetate:hexane (6:4) as a solvent system to obtain the pure product (9b) (450 mg, 75% yield).

$^1$H NMR (CDCl$_3$): δ8.03 (d, 1H, J=8.1 Hz), 7.87 (d, 1H, J=7.3 Hz), 7.69 (d, 1H, J=2.0 Hz), 7.54 (dd, 1H, J=8.3, 2.0 Hz), 7.44-7.51 (m, 1H), 7.33-7.38 (m, 1H), 6.99 (d, 1H, J=8.4 Hz), 6.84-6.90 (m, 2H), 6.76 (d, 1H, J=8.6 Hz), 6.47-6.51 (m, 3H), 6.43 (d, 1H, J=12.0 Hz), 4.26 (t, 2H, J=6.0 Hz), 4.08 (t, 2H, J=6.0 Hz), 3.98 (s, 3H), 3.83 (s, 3H), 3.82 (s, 3H), 3.68 (s, 6H), 2.25-2.36 (m, 2H).

ESIMS:614 (M+1)$^+$.

Example 2

2-[4-methoxy-3-(4-2-methoxy-5-[(Z)-2-(3,4,5-tri-methoxyphenyl)-1-ethenyl]phenoxybutoxy)phenyl]-1,3-benzothiazole (9m)

2-methoxy-5-[(Z)-2-(3,4,5-trimethoxyphenyl)-1-ethenyl]phenol (1) (316 mg, 1.0 mmol) in DMF (20 mL) was added anhydrous potassium carbonate (690 mg, 5.0 mmol) and 2-[3-(4-bromobutoxy)-4-methoxyphenyl]-1,3-benzothiazole (7m) (404 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using ethyl acetate:hexane (6:4) as a solvent system to obtain the pure product (9m) (470 mg, 74% yield).

$^1$H NMR (CDCl$_3$): δ7.96 (d, 1H, J=8.3 Hz), 7.84 (d, 1H, J=7.5 Hz), 7.68 (s, 1H), 7.51-7.54 (m, 1H), 7.40-7.45 (m, 1H), 7.28-7.35 (m, 1H), 6.88 (d, 1H, J=8.2 Hz), 6.76-6.83 (m, 1H), 6.65-6.73 (m, 2H), 6.47 (s, 2H), 6.40 (d, 1H, J=12.0 Hz), 6.34 (d, 1H, J=12.0 Hz), 4.21 (t, 2H, J=6.0 Hz), 3.89 (s, 3H), 3.86 (s, 3H), 3.78-3.80 (m, 5H), 3.68 (s, 6H), 1.95-2.05 (m, 4H).

ESIMS:628 (M+1)$^+$.

Example 3

2-[4-(4-2-methoxy-5-[(Z)-2-(3,4,5-trimethoxyphenyl)-1-ethenyl]phenoxybutoxy)phenyl]-1,3-benzothiazole (9h)

2-methoxy-5-[(Z)-2-(3,4,5-trimethoxyphenyl)-1-ethenyl]phenol (1) (316 mg, 1.0 mmol) in DMF (20 mL) was added anhydrous potassium carbonate (690 mg, 5.0 mmol) and 2-[4-(4-bromobutoxy)phenyl]-1,3-benzothiazole (7h) (362 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using ethyl acetate:hexane (6:4) as a solvent system to obtain the pure product (9h) (375 mg, 74% yield).

$^1$H NMR (CDCl$_3$): δ7.98-8.07 (m, 3H), 7.87 (d, 1H, J=8.3 Hz), 7.43-7.51 (t, 1H, J=7.5 Hz), 7.31-7.39 (t, 1H, J=7.5 Hz), 6.95-7.03 (m, 2H), 6.82-6.92 (m, 2H), 6.70-6.80 (m, 1H), 6.47-6.55 (m, 3H), 6.45 (d, 1H, J=12.0 Hz), 4.08 (t, 2H, J=5.8 Hz), 3.85-3.93 (m, 5H), 3.84 (s, 3H), 3.70 (s, 6H), 1.88-1.99 (m, 4H).

ESIMS:598 (M+1)$^+$.

Example 4

E)-3-(3-3-[4-(1,3-benzothiazol-2-yl)-2-methoxyphenoxy]propoxy-4-methoxy phenyl)-1-(3,4,5-tri-methoxyphenyl)-2-propen-1-one (10b (E)-3-(3-hydroxy-4-methoxyphenyl)-1-(3,4,5-trimethoxyphenyl)-2-propen-1-one (2) (344 mg, 1.0 mmol) in DMF (20 mL) was added anhydrous potassium carbonate (690 mg, 5.0 mmol) and 2-[4-(3-bromopropoxy)-3-methoxyphenyl]-1,3-benzothiazole (7b) (378 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using ethyl acetate:hexane (6:4) as a solvent system to obtain the pure product (10b) (580 mg, 90% yield).

$^1$H NMR (CDCl$_3$): δ 7.98 (d, 1H, J=8.0 Hz), 7.83 (d, 1H, J=7.3 Hz), 7.64-7.75 (m, 2H), 7.48-7.55 (dd, 1H, J=8.7, 2.1 Hz), 7.39-7.47 (m, 1H), 7.27-7.37 (m, 2H), 7.17-7.24 (m, 4H), 6.96 (d, 1H, J=8.0 Hz), 6.85 (d, 1H, J=8.7 Hz), 4.24-4.37 (m, 4H), 3.98 (s, 3H), 3.92 (s, 6H), 3.87-3.90 (m, 6H), 2.31-2.49 (m, 2H).

ESIMS:642 (M+1)$^+$.

Example 5

E)-3-(3-4-[4-(1,3-benzothiazol-2-yl)phenoxy]butoxy-4-methoxyphenyl)-1-(3,4,5-trimethoxyphenyl)-2-propen-1-one (10h (E)-3-(3-hydroxy-4-methoxyphenyl)-1-(3,4,5-trimethoxyphenyl)-2-propen-1-one (2) (344 mg, 1.0 mmol) in DMF (20 mL) was added anhydrous potassium carbonate (690 mg, 5.0 mmol) and 2-[4-(4-bromobutoxy)phenyl]-1,3-benzothiazole (7h) (362 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using ethyl acetate:hexane (6:4) as a solvent system to obtain the pure product (10h) (503 mg, 74% yield).

$^1$H NMR (CDCl$_3$): δ7.96 (d, 1H, J=8.0 Hz), 7.82 (d, 1H, J=8.0 Hz), 7.65-7.76 (m, 2H), 7.48-7.56 (dd, 1H, J=8.0, 1.4 Hz), 7.37-7.47 (m, 1H), 7.22-7.36 (m, 2H), 7.12-7.21 (m, 4H), 6.79-6.92 (m, 3H), 4.13-4.34 (m, 4H), 3.92 (s, 6H), 3.89 (s, 3H), 3.87 (s, 3H), 2.06-2.21 (m, 4H).

ESIMS:626 (M+1)$^+$.

Example 6

2-(3-methoxy-4-3-[4-(4-2-methoxy-5-[(Z)-2-(3,4,5-trimethoxyphenyl)-1-ethenyl]phenoxybutyl)piperazino]propoxyphenyl)-1,3-benzothiazole (15c)

2-methoxy-5-[(Z)-2-(3,4,5-trimethoxyphenyl)-1-ethenyl]phenol (1) (316 mg, 1.0 mmol) in DMF (20 mL) was added anhydrous potassium carbonate (690 mg, 5.0 mmol) and 2-(4-3-[4-(4-bromobutyl)piperazino]propoxy-3-methoxyphenyl)-1,3-benzothiazole(8c) (518 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using chloroform:methanol (9:1) as a solvent system to obtain the pure product (15c) (600 mg, 80% yield).

$^1$H NMR (CDCl$_3$): δ8.02 (d, 1H, J=8.3 Hz), 7.87 (d, 1H, J=7.5 Hz), 7.70 (d, 1H, J=2.2 Hz), 7.56-7.59 (dd, 1H, J=8.3, 2.2 Hz), 7.43-7.50 (m, 1H), 7.32-7.38 (m, 1H), 6.93 (d, 1H, J=8.3 Hz), 6.84-6.88 (m, 1H), 6.72-6.78 (m, 2H), 6.51 (s, 2H), 6.48 (d, 1H, J=12.0 Hz), 6.44 (d, 1H, J=12.0 Hz), 4.15 (t, 2H, J=6.0 Hz), 3.99 (s, 3H), 3.83 (s, 3H), 3.77-3.81 (m, 5H), 3.70 (s, 6H), 2.68-3.09 (m, 12H), 2.06-2.17 (m, 2H), 1.67-1.81 (m, 4H).

ESIMS:754 (M+1)$^+$.

Example 7

2-(4-4-[4-(4-2-methoxy-5-[(Z)-2-(3,4,5-trimethoxyphenyl)-1-ethenyl]phenoxybutyl)piperazino]butoxyphenyl)-1,3-benzothiazole (15h)

2-methoxy-5-[(Z)-2-(3,4,5-trimethoxyphenyl)-1-ethenyl] phenol (1) (316 mg, 1.0 mmol) in DMF (20 mL) was added anhydrous potassium carbonate (690 mg, 5.0 mmol) and 2-(4-4-[4-(4-bromobutyl)piperazino]butoxyphenyl)-1,3-benzothiazole (8h) (502 mg, 1.0 mmol). The reaction mixture was stirred at a temperature of 30° C. for 24 h and the reaction was monitored by TLC. After completion of reaction added cool water and extracted with chloroform. The solvent was evaporated under vacuum to afford the crude product. This was purified by column chromatography using chloroform:methanol (9:1) as a solvent system to obtain the pure product (15h) (580 mg, 79% yield).

$^1$H NMR (CDCl$_3$): δ 8.0-8.04 (m, 3H), 7.86 (d, 1H, J=8.0 Hz), 7.45-7.49 (m, 1H), 7.33-7.37 (m, 1H), 6.96-6.99 (m, 2H), 6.84-6.87 (m, 1H), 6.75-6.78 (m, 2H), 6.46-6.52 (m, 3H), 6.44 (d, 1H, J=12.4 Hz), 4.06 (t, 2H, J=5.8 Hz), 3.83 (s, 3H), 3.81 (s, 3H), 3.78 (t, 2H, J=5.8 Hz), 3.70 (s, 6H), 2.68-3.04 (m, 12H), 1.79-1.89 (m, 4H), 1.69-1.75 (m, 4H).

ESIMS:738 (M+1).

Example 8

2-(4-methoxy-3-4-[4-(4-2-methoxy-5-[(Z)-2-(3,4,5-trimethoxyphenyl)-1-ethenyl]phenoxybutyl)piperazino]butoxyphenyl)-1,3-benzothiazole (15m)

2-methoxy-5-[(Z)-2-(3,4,5-trimethoxyphenyl)-1-ethenyl] phenol (1) (316 mg, 1.0 mmol) in DMF (20 mL) was added anhydrous potassium carbonate (690 mg, 5.0 mmol) and 2-(3-4-[4-(4-bromobutyl)piperazino]butoxy-4-methoxyphenyl)-1,3-benzothiazole (8m) (532 mg, 1.0 mmol). The reaction mixture was stirred at a temperature of 30° C. for 24 h and the reaction was monitored by TLC. After completion of reaction added cool water and extracted with chloroform. The solvent was evaporated under vacuum to afford the crude product. This was purified by column chromatography using chloroform:methanol (9:1) as a solvent system to obtain the pure product (15m) (600 mg, 80% yield).

$^1$H NMR (CDCl$_3$): δ58.02 (d, 1H, J=7.9 Hz), 7.70 (d, 1H, J=2.0 Hz), 7.57-7.62 (dd, 1H, J=8.3, 2.0 Hz), 7.44-7.50 (m, 1H), 7.32-7.39 (m, 1H), 6.95 (d, 1H, J=8.5 Hz), 6.84-6.89 dd, 1H, J=8.1, 1.8 Hz), 6.73-6.79 (m, 2H), 6.51 (s, 2H), 6.48 (d, 1H, J=12.0 Hz), 6.45 (d, 1H, J=12.0 Hz), 4.19 (t, 2H, J=6.0 Hz), 3.93 (s, 3H), 3.83 (s, 3H), 3.81 (s, 3H), 3.78 (t, 2H, J=5.6 Hz), 3.70 (s, 6H), 2.82-3.03 (m, 8H), 2.64-2.79 (m, 4H), 1.78-1.99 (m, 4H), 1.66-1.76 (m, 4H).

ESIMS:768 (M+1)$^+$.

Example 9

E)-3-3-[4-(4-3-[4-(1,3-benzothiazol-2-yl)-2-methoxyphenoxy]propylpiperazino)butoxy]-4-methoxyphenyl-1-(3,4,5-trimethoxyphenyl)-2-propen-1-one (16c (E)-3-(3-hydroxy-4-methoxyphenyl)-1-(3,4,5-trimethoxyphenyl)-2-propen-1-one (2) (344 mg, 1.0 mmol) in DMF (20 mL) was added anhydrous potassium carbonate (690 mg, 5.0 mmol) and 2-(4-3-[4-(4-bromobutyl)piperazino]propoxy-3-methoxyphenyl)-1,3-benzothiazole (8c) (518 mg, 1.0 mmol). The reaction mixture was stirred at a temperature of 30° C. for 24 h and the reaction was monitored by TLC. After completion of reaction added cool water and extracted with chloroform. The solvent was evaporated under vacuum to afford the crude product. This was purified by column chromatography using chloroform:methanol (9:1) as a solvent system to obtain the pure product (16c) (620 mg, 80% yield).

$^1$H NMR (CDCl$_3$): δ 7.99 (d, 1H, J=8.3 Hz), 7.83 (d, 1H, J=8.3 Hz), 7.66-7.74 (m, 2H), 7.48-7.53 (dd, 1H, J=8.3, 1.5 Hz), 7.40-7.47 (m, 1H), 7.37 (d, 1H, J=15.1 Hz), 7.28-7.32 (m, 1H), 7.16-7.23 (m, 4H), 6.88 (d, 1H, J=8.3 Hz), 6.84 (d, 1H, J=9.0 Hz), 4.09 (t, 2H, J=6.0 Hz), 3.98 (s, 3H), 3.94 (s, 6H), 3.89 (s, 3H), 3.87 (s, 3H), 3.84 (t, 2H, J=6.0 Hz), 2.62-2.93 (m, 12H), 2.0-2.12 (m, 2H), 1.72-1.9 (m, 4H). ESIMS: 782 (M+1)$^+$.

Example 10

E)-3-3-[4-(4-4-[5-(1,3-benzothiazol-2-yl)-2-methoxyphenoxy]butylpiperazino) butoxy]-4-methoxyphenyl-1-(3,4,5-trimethoxyphenyl)-2-propen-1-one (16m (E)-3-(3-hydroxy-4-methoxyphenyl)-1-(3,4,5-trimethoxyphenyl)-2-propen-1-one (2) (344 mg, 1.0 mmol) in DMF (20 mL) was added anhydrous potassium carbonate (690 mg, 5.0 mmol) and 2-(3-4-[4-(4-bromobutyl)piperazino]butoxy-4-methoxyphenyl)-1,3-benzothiazole (8m) (532 mg, 1.0 mmol). The reaction mixture was stirred at a temperature of 30° C. for 24 h and the reaction was monitored by TLC. After completion of reaction added cool water and extracted with chloroform. The solvent was evaporated under vacuum to afford the crude product. This was purified by column chromatography using chloroform:methanol (9:1) as a solvent system to obtain the pure product (16m) (640 mg, 81% yield).

$^1$H NMR (CDCl$_3$): δ7.97 (d, 1H, J=8.3 Hz), 7.83 (d, 1H, J=8.3 Hz), 7.65-7.74 (m, 2H), 7.49-7.55 (m, 1H), 7.40-7.47 (m, 1H), 7.28-7.39 (m, 2H), 7.25 (s, 2H), 7.15-7.221 (m, 2H), 6.88 (d, 1H, J=8.3 Hz), 6.84 (d, 1H, J=8.3 Hz), 4.16 (t, 2H, J=6.0 Hz), 4.02 (t, 2H, J=6.0 Hz), 3.93 (s, 6H), 3.91 (s, 3H), 3.89 (s, 3H), 3.87 (s, 3H), 2.52-2.83 (m, 12H), 1.64-1.96 (m, 8H).

ESIMS:796 (M+1)$^+$.

Example 11

1-[5-[3-({3-[4-(1,3-benzothiazol-2-yl)-2-methoxyphenoxy]propyl}oxy)-4-methoxy phenyl]-3-(3,4,5-trimethoxyphenyl)-4,5-dihydro-1H-1-pyrazolyl]-1-ethanone(11b)

1-(5-(3-hydroxy-4-methoxyphenyl)-3-(3,4,5-trimethoxyphenyl)-4,5-dihydro-1H-pyrazol-1-yl)ethanone (3) (400 mg, 1.0 mmol) in DMF (20 mL) was added anhydrous potassium carbonate (690 mg, 5.0 mmol) and 2-[4-(3-bromopropoxy)-3-methoxyphenyl]-1,3-benzothiazole (7b) (378 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using ethyl acetate:hexane (6:4) as a solvent system to obtain the pure product (11b) (420 mg, 76% yield).

$^1$H NMR (CDCl$_3$): δ7.88 (d, 1H, J=8.1 Hz), 7.78 (d, 1H, J=7.3 Hz), 7.64-7.73 (m, 2H), 7.44-7.52 (dd, 1H, J=8.3, 2.1 Hz), 7.23-7.34 (m, 2H), 6.95 (s, 2H), 6.68-6.84 (m, 3H), 5.45-5.57 (dd, 1H, J=11.7, 4.4 Hz), 4.2-4.32 (m, 4H), 3.91 (s, 6H), 3.89 (s, 3H), 3.85 (s, 6H), 3.6-3.79 (dd, 1H, J=17.7, 11.2 Hz), ), 3.2-3.22 (dd, 1H, J=17.6, 4.4 Hz), 2.31-2.45 (m, 2H), 2.29 (s, 3H).

ESIMS:697 (M+1)$^+$.

Example 12

1-[5-(3-{3-[4-(1,3-benzothiazol-2-yl)-2-methoxyphenoxy]propoxy}-4-methoxy phenyl)-3-(3,4,5-trimethoxyphenyl)-1H-1-pyrazolyl]-1-ethanone(12b)

1-(5-(3-hydroxy-4-methoxyphenyl)-3-(3,4,5-trimethoxyphenyl)-1H-pyrazol-1-yl)ethanone (4) (398 mg, 1.0 mmol) in DMF (20 mL) was added anhydrous potassium carbonate (690 mg, 5.0 mmol) and 2-[4-(3-bromopropoxy)-3-methoxyphenyl]-1,3-benzothiazole (7b) (378 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using ethyl acetate:hexane (6:4) as a solvent system to obtain the pure product (12b) (410 mg, 75% yield).

$^1$H NMR (CDCl$_3$): δ7.88 (d, 1H, J=8.1 Hz), 7.78 (d, 1H, J=7.3 Hz), 7.64-7.73 (m, 2H), 7.44-7.52 (dd, 1H, J=8.3, 2.1 Hz), 7.23-7.34 (m, 2H), 6.95 (s, 2H), 6.68-6.84 (m, 3H), 6.62 (s, 1H), 4.2-4.32 (m, 4H), 3.91 (s, 6H), 3.89 (s, 3H), 3.85 (s, 6H), 2.31-2.45 (m, 2H), 2.29 (s, 3H)

ESIMS:695 (M+1)$^+$.

Example 13

5-(3-{3-[4-(1,3-benzothiazol-2-yl)-2-methoxyphenoxy]propoxy}-4-methoxyphenyl)-3-(3,4,5-trimethoxyphenyl)-4,5-dihydroisoxazole(13b)

2-methoxy-5-(3-(3,4,5-trimethoxyphenyl)-4,5-dihydroisoxazol-5-yl)phenol (5) (359 mg, 1.0 mmol) in DMF (20 mL) was added anhydrous potassium carbonate (690 mg, 5.0 mmol) and 2-[4-(3-bromopropoxy)-3-methoxyphenyl]-1,3-benzothiazole (7b) (378 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using ethyl acetate:hexane (6:4) as a solvent system to obtain the pure product (13b) (359 mg, 58% yield).

$^1$H NMR (CDCl$_3$): δ7.91 (d, 1H, J=7.8 Hz), 7.8 (d, 1H, J=7.2 Hz), 7.61-7.72 (m, 2H), 7.41-7.52 (dd, 1H, J=8.1, 2.3 Hz), 7.2-7.32 (m, 2H), 6.93 (s, 2H), 6.65-6.71 (m, 2H), 6.61 (d, 1H, J=8.7 Hz), 5.54-5.62 (dd, 1H, J=11.4, 4.4 Hz), 4.22- 4.35 (m, 4H), 3.92 (s, 6H), 3.88 (s, 3H), 3.85 (s, 6H), 3.61-3.74 (dd, 1H, J=17.1, 11.4 Hz), ), 3.22-3.26 (dd, 1H, J=17.1, 4.4 Hz), 2.3-2.45 (m, 2H).

ESIMS:656 (M+1)$^+$.

Example 14

5-(3-{3-[4-(1,3-benzothiazol-2-yl)phenoxy]propoxy}-4-methoxyphenyl)-3-(3,4,5-trimethoxyphenyl)isoxazole(14b)

2-methoxy-5-(3-(3,4,5-trimethoxyphenyl)isoxazol-5-yl)phenol (6) (357 mg, 1.0 mmol) in DMF (20 mL) was added anhydrous potassium carbonate (690 mg, 5.0 mmol) and 2-[4-(3-bromopropoxy)-3-methoxyphenyl]-1,3-benzothiazole (7b) (378 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using ethyl acetate:hexane (6:4) as a solvent system to obtain the pure product (14b) (325 mg, 51% yield).

$^1$H NMR (CDCl$_3$): δ7.91 (d, 1H, J=7.8 Hz), 7.82 (d, 1H, J=7.3 Hz), 7.62-7.73 (m, 2H), 7.4-7.51 (dd, 1H, J=8.1, 2.3 Hz), 7.21-7.32 (m, 2H), 6.92 (s, 2H), 6.64-6.7 (m, 2H), 6.63 (s, 1H), 6.6 (d, 1H, J=8.7 Hz), 4.21-4.36 (m, 4H), 3.91 (s, 6H), 3.87 (s, 3H), 3.85 (s, 6H), 2.31-2.46 (m, 2H).

ESIMS:654 (M+1)$^+$.

Example 15

1-[5-(3-{[3-(4-{3-[4-(1,3-benzothiazol-2-yl)-2-methoxyphenoxy]propyl}piperazino) propyl]oxy}-4-methoxyphenyl)-3-(3,4,5-trimethoxyphenyl)-4,5-dihydro-1H-1-pyrazolyl]-1-ethanone(17b)

1-(5-(3-hydroxy-4-methoxyphenyl)-3-(3,4,5-trimethoxyphenyl)-4,5-dihydro-1H-pyrazol-1-yl)ethanone (3) (400 mg, 1.0 mmol) in DMF (20 mL) was added anhydrous potassium carbonate (690 mg, 5.0 mmol) and 2-(4-4-[4-(4-bromopropyl)piperazino]proxyphenyl)-1,3-benzothiazole (8b) (518 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using chloroform:methanol (9:1) as a solvent system to obtain the pure product (17b) (425 mg, 55% yield).

$^1$H NMR (CDCl$_3$): δ7.89 (d, 1H, J=8.3 Hz), 7.78 (d, 1H, J=7.3 Hz), 7.65-7.73 (m, 2H), 7.44-7.51 (dd, 1H, J=8.3, 2.3 Hz), 7.24-7.33 (m, 2H), 6.94 (s, 2H), 6.69-6.84 (m, 3H), 5.44-5.57 (dd, 1H, J=11.7, 4.4 Hz), 4.14-4.26 (m, 4H), 3.91 (s, 6H), 3.88 (s, 3H), 3.85 (s, 6H), 3.61-3.79 (dd, 1H, J=17.7, 11.2 Hz), ), 3.21-3.28 (dd, 1H, J=17.6, 4.4 Hz), 2.68-3.04 (m, 12H), 2.29 (s, 3H), 1.79-1.89 (m, 4H).

ESIMS:759 (M+1)$^+$.

Example 16

1-[5-(3-{[3-(4-{3-[4-(1,3-benzothiazol-2-yl)-2-methoxyphenoxy]propyl}piperazino) propyl]oxy}-4-methoxyphenyl)-3-(3,4,5-trimethoxyphenyl)-1H-1-pyrazolyl]-1-ethanone(18b)

1-(5-(3-hydroxy-4-methoxyphenyl)-3-(3,4,5-trimethoxyphenyl)-1H-pyrazol-1-yl)ethanone (4) (398 mg, 1.0 mmol)

in DMF (20 mL) was added anhydrous potassium carbonate (690 mg, 5.0 mmol) and 2-(4-4-[4-(4-bromopropyl)piperazino]proxyphenyl)-1,3-benzothiazole (8b) (518 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using chloroform:methanol (9:1) as a solvent system to obtain the pure product (18b) (410 mg, 53% yield).

$^1$H NMR (CDCl$_3$): δ7.89 (d, 1H, J=8.5 Hz), 7.78 (d, 1H, J=7.3 Hz), 7.64-7.73 (m, 2H), 7.43-7.52 (dd, 1H, J=8.3, 2.1 Hz), 7.21-7.34 (m, 2H), 6.95 (s, 2H), 6.67-6.84 (m, 3H), 6.63 (s, 1H), 4.2-4.32 (m, 4H), 3.91 (s, 6H), 3.89 (s, 3H), 3.85 (s, 6H), 2.75-3.07 (m, 12H), 2.27 (s, 3H), 1.85-1.91 (m, 4H).

ESIMS:757 (M+1)$^+$.

Example 17

5-(3-{[3-(4-{3-[4-(1,3-benzothiazol-2-yl)-2-methoxyphenoxy]propyl}piperazino) propyl]oxy}-4-methoxyphenyl)-3-(3,4,5-trimethoxyphenyl)-4,5-dihydroisoxazole(19b)

2-methoxy-5-(3-(3,4,5-trimethoxyphenyl)-4,5-dihydroisoxazol-5-yl)phenol (5) (359 mg, 1.0 mmol) in DMF (20 mL) was added anhydrous potassium carbonate (690 mg, 5.0 mmol) and 2-(4-4-[4-(4-bromopropyl)piperazino]proxyphenyl)-1,3-benzothiazole (8b) (518 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using chloroform:methanol (9:1) as a solvent system to obtain the pure product (19b) (470 mg, 76% yield).

$^1$H NMR (CDCl$_3$): δ7.92 (d, 1H, J=7.3 Hz), 7.81 (d, 1H, J=7.3 Hz), 7.62-7.72 (m, 2H), 7.4-7.52 (dd, 1H, J=8.3, 2.3 Hz), 7.21-7.32 (m, 2H), 6.92 (s, 2H), 6.65-6.7 (m, 2H), 6.62 (d, 1H, J 5=8.5 Hz), 5.54-5.61 (dd, 1H, J=11.4, 4.4 Hz), 4.21-4.34 (m, 4H), 3.91 (s, 6H), 3.89 (s, 3H), 3.85 (s, 6H), 3.62-3.72 (dd, 1H, J=17.3, 11.4 Hz), ), 3.21-3.26 (dd, 1H, J=17.3, 4.4 Hz), 2.61-3.11 (m, 12H), 1.65-1.72 (m, 4H).

ESIMS:717 (M+1)$^+$.

Example 18

5-(3-{[3-(4-{3-[4-(1,3-benzothiazol-2-yl)-2-methoxyphenoxy]propyl}piperazino) propyl]oxy}-4-methoxyphenyl)-3-(3,4,5-trimethoxyphenyl)isoxazole (20b)

2-methoxy-5-(3-(3,4,5-trimethoxyphenyl)isoxazol-5-yl)phenol (6) (357 mg, 1.0 mmol) in DMF (20 mL) was added anhydrous potassium carbonate (690 mg, 5.0 mmol) and 2-(4-4-[4-(4-bromopropyl)piperazino]proxyphenyl)-1,3-benzothiazole (8b) (518 mg, 1.0 mmol). The reaction mixture was stirred at a temperature of 30° C. for 24 h and the reaction was monitored by TLC. After completion of reaction added cool water and extracted with ethyl acetate. The solvent was evaporated under vacuum to afford the crude product. This was purified by column chromatography using chloroform: methanol (9:1) as a solvent system to obtain the pure product (20b) (475 mg, 75% yield).

$^1$H NMR (CDCl$_3$): δ 7.9 (d, 1H, J=7.5 Hz), 7.81 (d, 1H, J=7.3 Hz), 7.61-7.73 (m, 2H), 7.42-7.51 (dd, 1H, J=8.3, 2.1 Hz), 7.22-7.32 (m, 2H), 6.93 (s, 2H), 6.62-6.7 (m, 2H), 6.62 (s, 1H), 6.59 (d, 1H, J=8.7 Hz), 4.2-4.36 (m, 4H), 3.91 (s, 6H), 3.89 (s, 3H), 3.85 (s, 6H), 2.59-2.95 (m, 12H), 1.62-1.71 (m, 4H).

ESIMS:715 (M+1)$^+$.

Biological Activity: In vitro Cytotoxicity

The benzothiazole hybrids has been tested against seven human tumor cell lines derived from six cancer types (lung cancer, colon cancer, CNS cancer, ovarian cancer, prostate cancer and breast cancer). For these compounds results are expressed as percent of cell growth inhibition relative to that of untreated control cells. A protocol of 48 h continuous drug exposure has been used, and a sulforhodamine B (SRB) protein assay was used to estimate cell viability or growth.

The compounds 9b, 9h, 9m, 9r, 15c, 15h, 15m, 15r, 10b, 10h, 10m, 10r, 16c, 16h and 16m were evaluated for in vitro anticancer activity against seven human tumor cells derived from six cancer types (lung cancer, colon cancer, CNS cancer, ovarian cancer, prostate cancer and breast cancer) at concentration of 10 μM and the results are shown in Table 1.

The compounds 9b, 9h, 9m, 9r, 15c, 15h, 15m and 15r exhibited an interesting profile of activity for various cell lines. There is an increase in activity is observed in compounds 15c, 15h, 15m and 15r with introduction of piperazine ring in compounds 9b, 9h, 9m and 9r. Table 2. In vitro cytotoxicity of compounds 9b, 9h, 9m, 9r, 15c, 15h, 15m, 15r, 10b, 10h, 10m, 10r, 16c, 16h and 16m in different cancer cell lines.

| Compound | % of growth inhibition at 10 μM concentration | | | | | | |
|---|---|---|---|---|---|---|---|
| | Lung A-549 | Ovarian IGR-OV-1 | Colon Colo-205 | Colon SW-620 | Prostate PC-3 | Breast MCF7 | CNS SF-295 |
| 9b | 69 | 54 | 16 | NT | 78 | 57 | 53 |
| 9h | 63 | 54 | 15 | NT | 65 | 64 | 34 |
| 9m | 73 | 58 | 70 | NT | 68 | 64 | 44 |
| 9r | 59 | 48 | NT | 22 | 59 | 52 | 71 |
| 15c | 88 | 95 | NT | 86 | 53 | 95 | 99 |
| 15h | 91 | 83 | NT | 72 | 96 | 93 | 98 |
| 15m | 100 | 99 | NT | 99 | 60 | 97 | 98 |
| 15r | 96 | 92 | NT | 99 | 70 | 88 | 98 |
| 10b | 66 | 21 | NT | 0 | 5 | 19 | 51 |
| 10h | 31 | 17 | NT | 2 | 6 | 9 | 38 |
| 10m | 7 | 17 | NT | 27 | 0 | 24 | 14 |
| 10r | 41 | 0 | NT | 0 | 1 | 14 | 21 |
| 16c | 58 | 67 | NT | 0 | 24 | 69 | 24 |
| 16h | 59 | 73 | NT | 0 | 67 | 84 | 63 |
| 16m | 100 | 85 | NT | 0 | 2 | 57 | 15 |

-continued

|  | % of growth inhibition at 10 μM concentration | | | | | | |
|---|---|---|---|---|---|---|---|
| Compound | Lung A-549 | Ovarian IGR-OV-1 | Colon Colo-205 | Colon SW-620 | Prostate PC-3 | Breast MCF7 | CNS SF-295 |
| 5-Fluoro uracil (at 10 μM) | 64 | 47 | 55 | 41 | 29 | 66 | 9 |
| Paclitaxel (at 1 μM) | 62 | 44 | 95 | NT | 35 | 59 | 59 |
| Mitomycin (at 1 μM) | 29 | 5 | 0 | NT | 66 | 27 | 11 |
| Adriyamycin (at 1 μM) | 95 | 78 | 77 | 21 | 55 | 69 | 55 |

NT—not tested

Significance of the Work Carried Out

The novel benzothiazole hybrids that have been synthesized exhibited significant cytotoxic activity against different human tumour cell lines.

ADVANTAGES OF THE INVENTION

1. The present invention provides benzothiazole hybrids useful as antitumour agents.
2. It also provides a process for the preparation of benzothiazole hybrids.

We claim:

1. Compounds of general formulae A

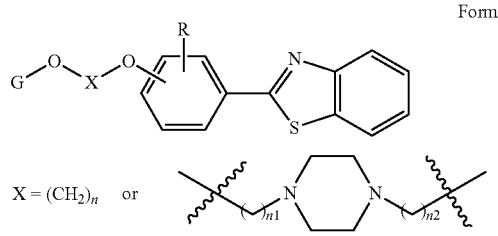

Formula A

X = (CH$_2$)$_n$ or n = 2-6; n1 & n2 = 2-6

Where in R = H or methoxy and
G =

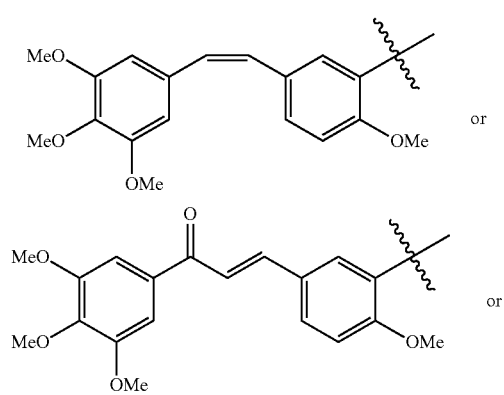

-continued

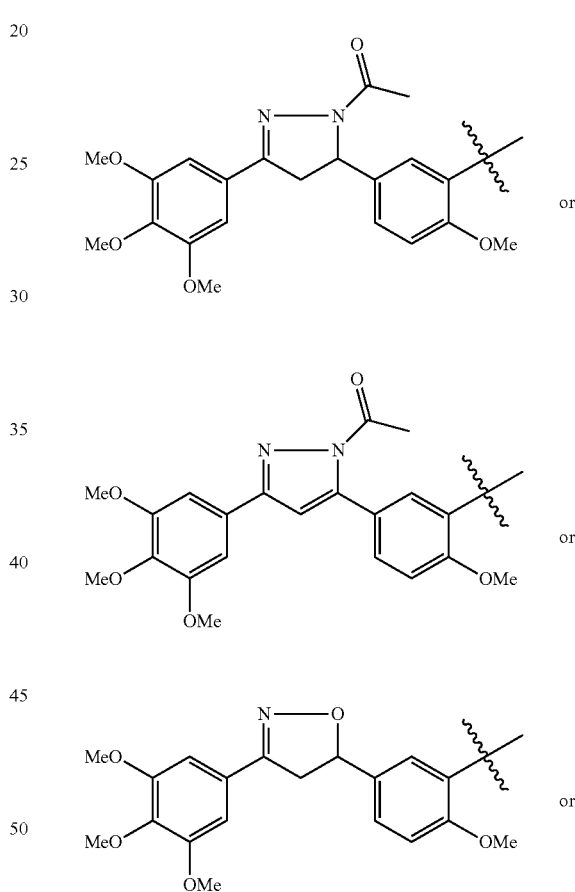

2. The compound of claim 1 as represented by the following compounds of general formulae 9a-t, 10a-t, 11a-t, 12a-t, 13a-t, 14a-t, 15a-t, 16a-t, 17a-t, 18a-t, 19a-t and 20a-t

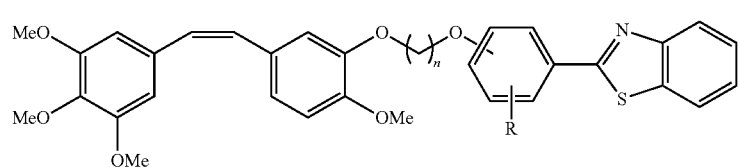
9a-t
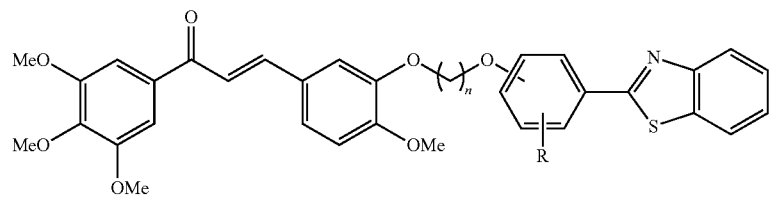
10a-t
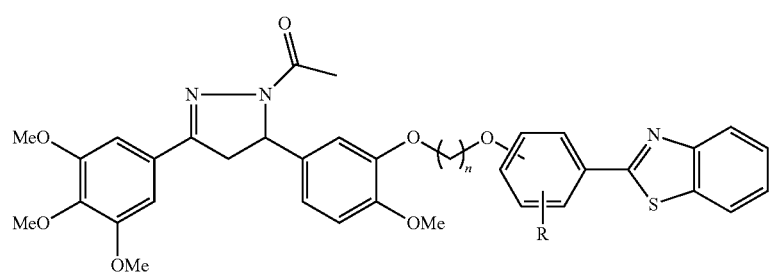
11a-t
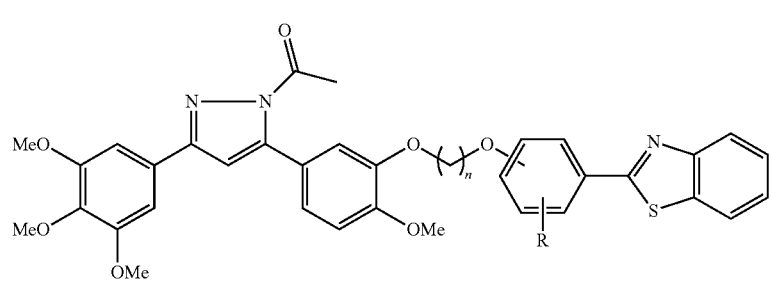
12a-t
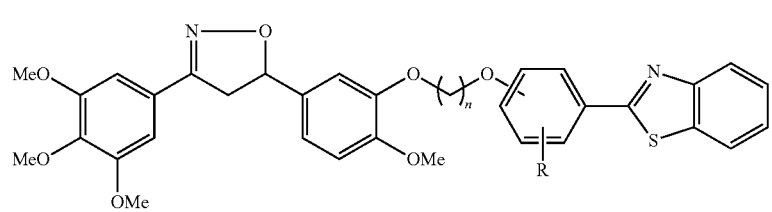
13a-t
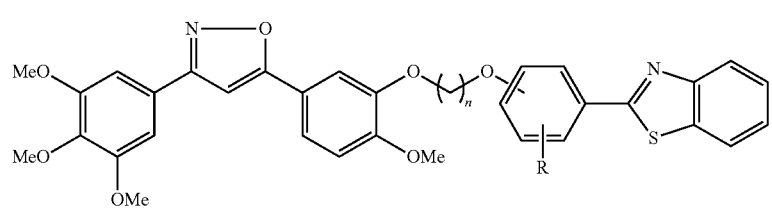
14a-t
where in n = 2-6
R = H, methoxy
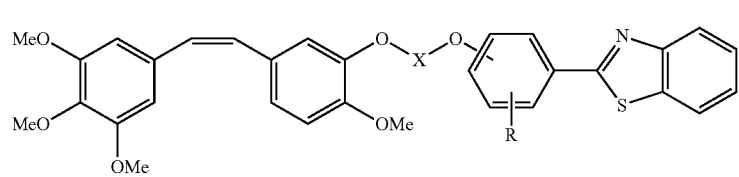
15a-t 16a-t
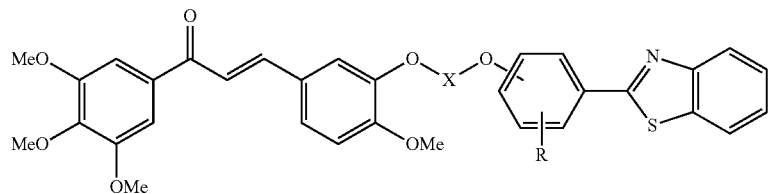
17a-t
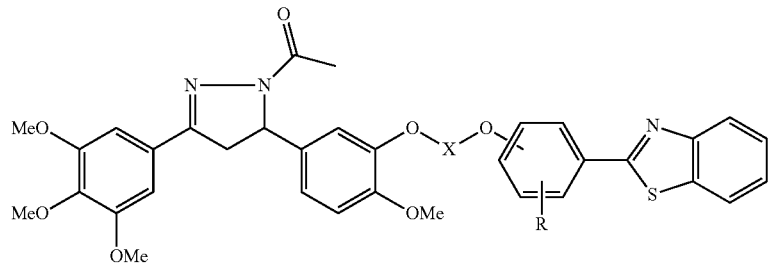
18a-t
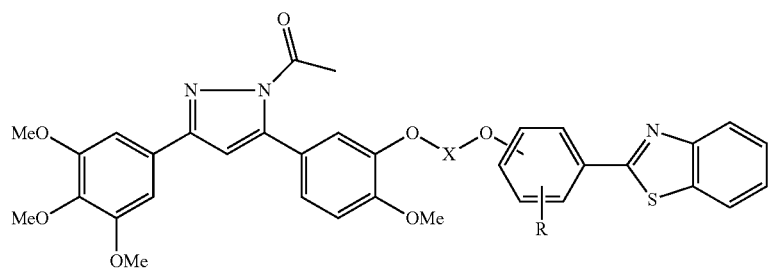
19a-t
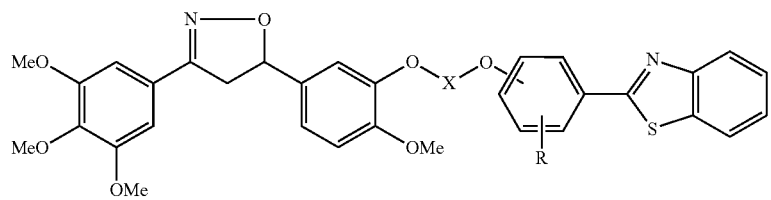
20a-t
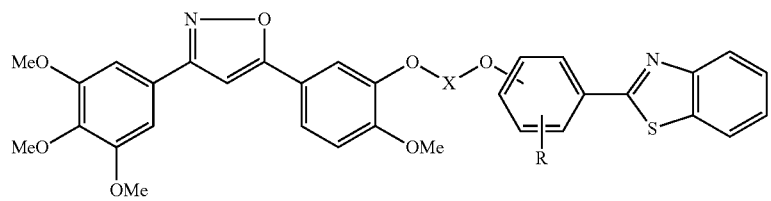
where in
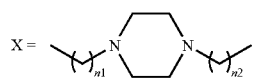
n1 and n2 = 2-6
R = H, methoxy
3. A process for the preparation of benzothiazole hybrids of general formulae A
Formula A
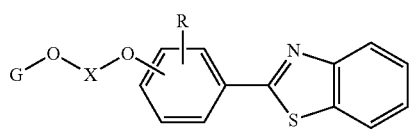
-continued
$X = (CH_2)_n$ or 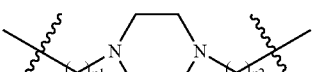
$n$ = 2-6; $n1$ & $n2$ = 2-6

-continued
Where in R = H or methoxy and
G =
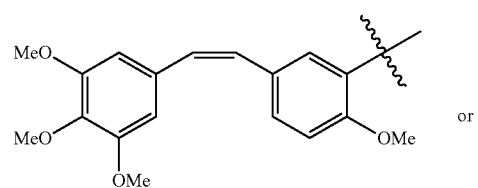
or
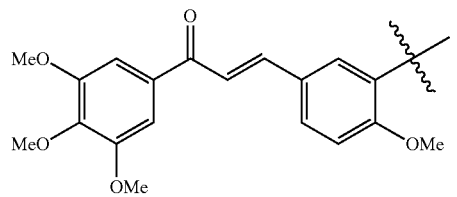 [SMILES: *c1cc(-c2cc(-c3cc(OC)c(OC)c(OC)c3)no2)ccc1OC]
or
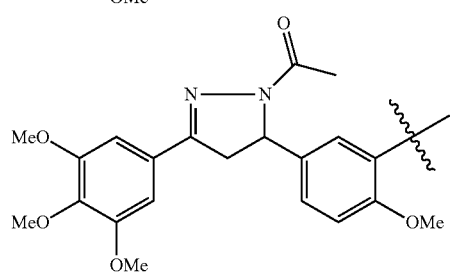
or
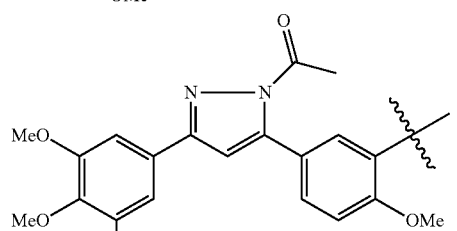
or
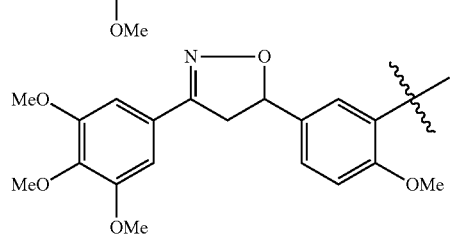
or
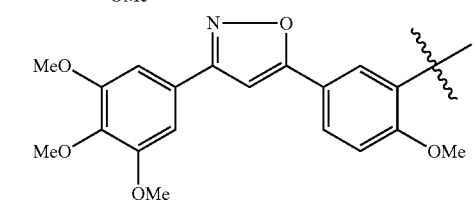
and the said process comprising steps of
(a) reacting benzothiazole a derivative of formula 7 or 8
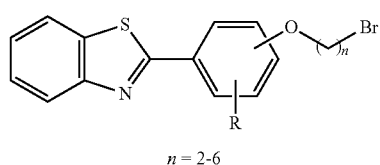
7
$n = 2-6$
-continued
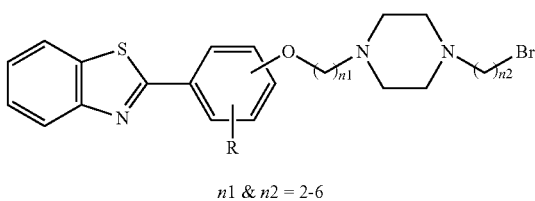
8
$n1$ & $n2$ = 2-6
with a compound of formula 1, 2, 3, 4, 5, or 6
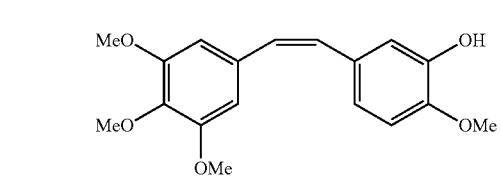
1
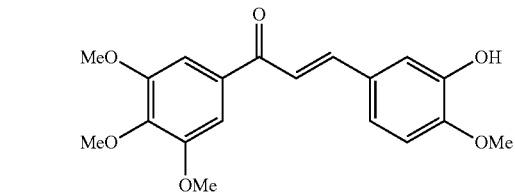
2
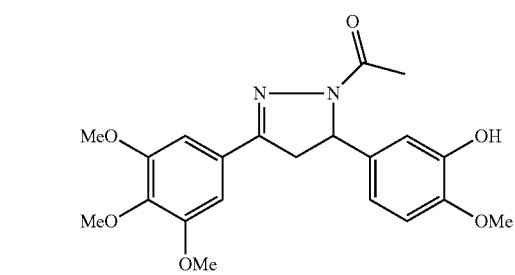
3
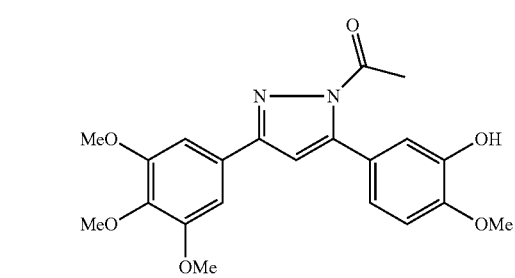
4
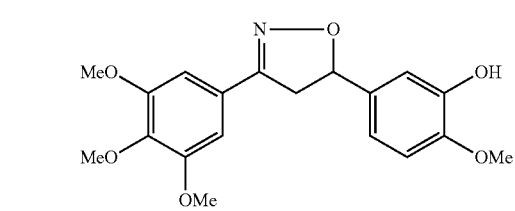
5

-continued

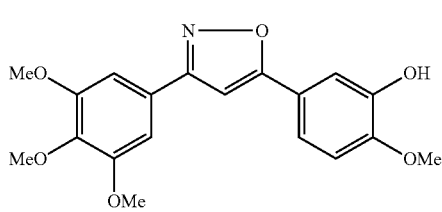

6

(b) in an organic solvent in the presence of inorganic base selected from the group consisting of potassium carbonate or sodium carbonate at temperature range of 25-35° C. for a period of about 22-26 h, (c) followed by adding water, extracting with organic solvent and evaporating the organic solvent to obtain the resultant crude product;

(d) and purifying the crude product by column chromatography to obtain the desired products of formulae A.

4. The process of claim 3, wherein the molar ratios of compound of formula 7 or 8 are 1.0 mmol with the compounds of formula 1, 2, 3, 4, 5 or 6 are 1.0-2.0 mmol and inorganic base is 1.0-6.0 mmol.

5. The process of claim 3, wherein the reaction in step (a) is performed for a period of about 22-26 h.

6. The process of claim 3, wherein the organic solvent is selected from the group consisting of N,N-dimethylformamide, acetone, acetonitrile, dimethylsulfoxide and ethyl acetate.

7. A method for treatment of a human tumor cell line comprising: in vitro administrating the compound of claim 2 to the human tumor cell line, wherein the human tumor cell line is selected from the group consisting of lung cancer, colon cancer, CNS cancer, ovarian cancer, prostate cancer and breast cancer.

8. A method for treatment of a human tumor cell line comprising: in vitro administrating compounds 9b, 9h, 9m, 9r, 15c, 15h, 15m, 15r, 10b, 10h, 10m, 10r, 16c, 16h, 16m of claim 2 to the human tumor cell line, wherein the human tumor cell line is selected from the group consisting of lung cancer, colon cancer, CNS cancer, ovarian cancer, prostate cancer and breast cancer, and wherein the in vitro anticancer activity against the human tumor cell line is in the range of 1-100 at 10 pM concentration at an exposure period of at least 48 hrs.

* * * * *